United States Patent
Kurihara et al.

(10) Patent No.: US 11,469,380 B2
(45) Date of Patent: Oct. 11, 2022

(54) ORGANIC COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Miki Kurihara, Kanagawa (JP); Hideko Yoshizumi, Kanagawa (JP); Hiromitsu Kido, Kanagawa (JP); Satomi Watabe, Kanagawa (JP); Satoshi Seo, Kanagawa (JP)

(73) Assignee: Semiconductor Energy Laboratory Co., Ltd.

( * ) Notice: Subject to any disclaimer, the term of this patent is extended or adjusted under 35 U.S.C. 154(b) by 251 days.

(21) Appl. No.: 16/647,602

(22) PCT Filed: Sep. 6, 2018

(86) PCT No.: PCT/IB2018/056787
§ 371 (c)(1),
(2) Date: Mar. 16, 2020

(87) PCT Pub. No.: WO2019/058200
PCT Pub. Date: Mar. 28, 2019

(65) Prior Publication Data
US 2020/0259099 A1    Aug. 13, 2020

(30) Foreign Application Priority Data
Sep. 20, 2017 (JP) .............................. JP2017-180537

(51) Int. Cl.
*C07D 491/048* (2006.01)
*H01L 51/00* (2006.01)
(Continued)

(52) U.S. Cl.
CPC ...... *H01L 51/0071* (2013.01); *C07D 491/048* (2013.01); *C09K 11/025* (2013.01); *H01L 51/5016* (2013.01)

(58) Field of Classification Search
CPC ............ C07D 491/048; H01L 51/0071; H01L 51/0072; H01L 51/0073; H01L 51/0074
(Continued)

(56) References Cited

U.S. PATENT DOCUMENTS 7,906,226 B2    3/2011  Matsuura et al.
8,952,363 B2 *  2/2015  Lin ..................... H01L 51/5056
                                                    546/89
(Continued)

FOREIGN PATENT DOCUMENTS

CN    102341401 A    2/2012
CN    106573938 A    4/2017
(Continued)

OTHER PUBLICATIONS

International Search Report re Application No. PCT/IB2018/056787, dated Nov. 20, 2018.
(Continued)

*Primary Examiner* — Christopher M Raabe
(74) *Attorney, Agent, or Firm* — Husch Blackwell LLP

(57) ABSTRACT

A benzofuropyrimidine derivative or a benzothienopyrimidine derivative that is a novel organic compound is provided. The organic compound has a benzofuropyrimidine skeleton or a benzothienopyrimidine skeleton and is represented by General Formula (G1) below. In General Formula (G1), Q represents oxygen or sulfur. Each of $A^1$ and $A^2$ independently represents a substituted or unsubstituted polycyclic aromatic hydrocarbon. Furthermore, m represents any one of integers from 0 to 4. Furthermore, n represents any one of integers from 1 to 4. Each of $R^1$ to $R^{12}$ independently (Continued)

represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

22 Claims, 20 Drawing Sheets

(51) Int. Cl.
    *C09K 11/02*    (2006.01)
    *H01L 51/50*    (2006.01)

(58) Field of Classification Search
    USPC ........................................................ 428/690
    See application file for complete search history.

(56) References Cited

U.S. PATENT DOCUMENTS

| | | | |
|---|---|---|---|
| 9,067,947 B2 | 6/2015 | Lin et al. | |
| 9,518,063 B2 | 12/2016 | Lin et al. | |
| 9,831,442 B2 | 11/2017 | Lin et al. | |
| 10,586,931 B2 | 3/2020 | Kanamoto et al. | |
| 2010/0187984 A1 | 7/2010 | Lin et al. | |
| 2013/0240851 A1* | 9/2013 | Seo | H01L 51/5016 257/40 |
| 2015/0207082 A1 | 7/2015 | Dyatkin et al. | |
| 2015/0243893 A1* | 8/2015 | Joseph | C07D 491/04 257/40 |
| 2016/0351826 A1* | 12/2016 | Kim | H01L 51/0052 |
| 2017/0186971 A1 | 6/2017 | Kanamoto et al. | |
| 2017/0200903 A1 | 7/2017 | Park et al. | |
| 2017/0271610 A1 | 9/2017 | Takahashi | |
| 2017/0352447 A1 | 12/2017 | Lee et al. | |
| 2020/0010476 A1* | 1/2020 | Lee | C07D 407/14 |
| 2020/0024282 A1 | 1/2020 | Parham et al. | |
| 2020/0358004 A1* | 11/2020 | Choi | H01L 51/0074 |

FOREIGN PATENT DOCUMENTS

| | | |
|---|---|---|
| CN | 10843101 A | 8/2018 |
| EP | 2 703 405 A2 | 3/2014 |
| JP | 2010-182699 A | 8/2010 |
| JP | 2012-515216 | 7/2012 |
| JP | 2017-119682 A | 7/2017 |
| JP | 2017-175128 A | 9/2017 |
| JP | 2018-127402 A | 8/2018 |
| KR | 2011-0116177 A | 10/2011 |
| KR | 2015-0136942 A | 12/2015 |
| KR | 2018-0022608 A | 3/2018 |
| WO | WO 2010/083359 A1 | 7/2010 |
| WO | WO 2015/037675 A1 | 3/2015 |
| WO | WO 2015/182872 A1 | 12/2015 |
| WO | WO 2017/109637 A1 | 6/2017 |
| WO | WO 2017/158475 A1 | 9/2017 |
| WO | WO 2018/060307 A1 | 4/2018 |
| WO | WO 2018/234926 A1 | 12/2018 |

OTHER PUBLICATIONS

Written Opinion re Application No. PCT/IB2018/056787, dated Nov. 20, 2018.
Chinese Office Action (Application No. 201880055077.5) dated Mar. 23, 2022.

\* cited by examiner

FIG. 4A
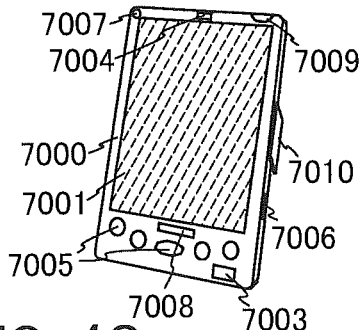
FIG. 4B
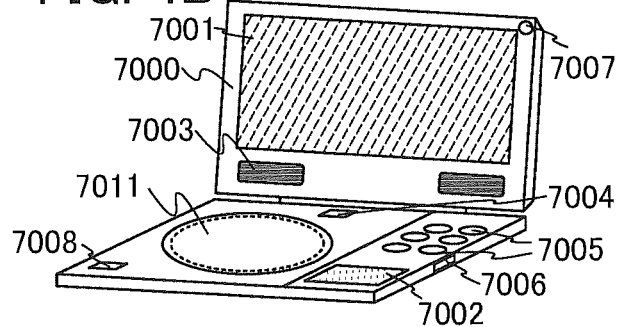
FIG. 4C
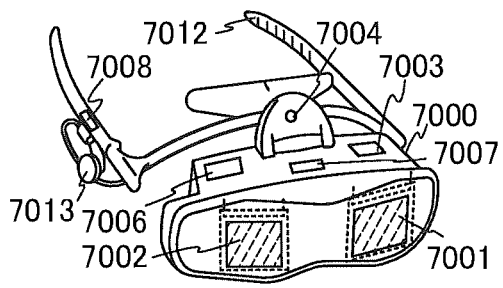
FIG. 4D
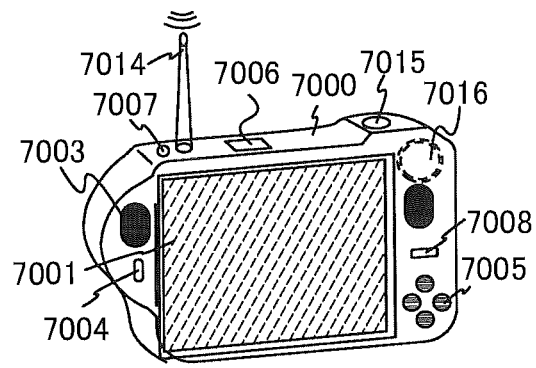
FIG. 4E
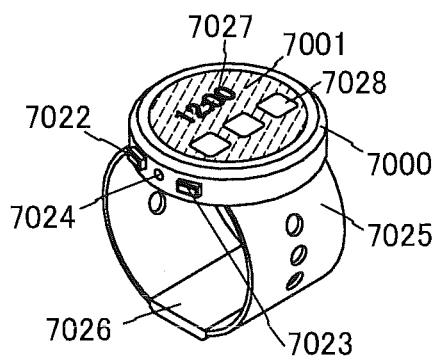
FIG. 4F
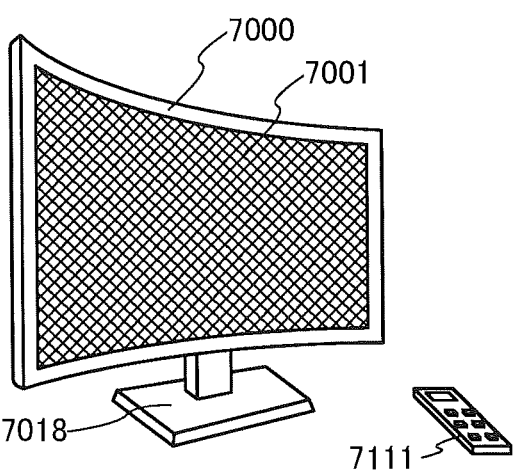
FIG. 4G

ORGANIC COMPOUND, LIGHT-EMITTING ELEMENT, LIGHT-EMITTING DEVICE, ELECTRONIC DEVICE, AND LIGHTING DEVICE

This application is a 371 of international application PCT/IB2018/056787 filed on Sep. 6, 2018 which is incorporated herein by reference.

TECHNICAL FIELD

One embodiment of the present invention relates to an organic compound, a light-emitting element, a light-emitting device, an electronic device, and a lighting device. However, one embodiment of the present invention is not limited to the above technical field. That is, one embodiment of the present invention relates to an object, a method, a manufacturing method, or a driving method. Alternatively, one embodiment of the present invention relates to a process, a machine, manufacture, or a composition of matter. Specific examples include a semiconductor device, a display device, a liquid crystal display device, and the like.

BACKGROUND ART

A light-emitting element including an EL layer between a pair of electrodes (also referred to as an organic EL element) has characteristics such as thinness, light weight, high-speed response to input signals, and low power consumption; thus, a display including such a light-emitting element has attracted attention as a next-generation flat panel display.

In a light-emitting element, voltage application between a pair of electrodes causes, in an EL layer, recombination of electrons and holes injected from the electrodes, which brings a light-emitting substance (organic compound) contained in the EL layer into an excited state. Light is emitted when the light-emitting substance returns to the ground state from the excited state. The excited state can be a singlet excited state (S*) and a triplet excited state (T*). Light emission from a singlet excited state is referred to as fluorescence, and light emission from a triplet excited state is referred to as phosphorescence. The statistical generation ratio thereof in the light-emitting element is considered to be S*:T*=1:3. Since the emission spectrum of a light-emitting substance depends on the light-emitting substance, the use of different types of organic compounds as light-emitting substances makes it possible to obtain light-emitting elements which exhibit various emission colors.

In order to improve element characteristics of such a light-emitting element, improvement of an element structure, development of a material, and the like have been actively carried out (see Patent Document 1, for example).

REFERENCE

Patent Document

[Patent Document 1] Japanese Published Patent Application No. 2010-182699

SUMMARY OF THE INVENTION

Problems to be Solved by the Invention

In view of this, in one embodiment of the present invention, a novel organic compound having a benzofuropyrimidine skeleton or a benzothienopyrimidine skeleton and having a polycyclic aromatic hydrocarbon is provided. In another embodiment of the present invention, a benzofuropyrimidine derivative or a benzothienopyrimidine derivative that is a novel organic compound is provided. In one embodiment of the present invention, a novel organic compound that can be used in a light-emitting element is provided. In one embodiment of the present invention, a novel organic compound that can be used in an EL layer of a light-emitting element is provided. In addition, a highly reliable and novel light-emitting element using a novel organic compound of one embodiment of the present invention is provided. In addition, a novel light-emitting device, a novel electronic device, or a novel lighting device is provided. Note that the description of these objects does not disturb the existence of other objects. Note that in one embodiment of the present invention, there is no need to achieve all the objects. Objects other than these will be apparent from the description of the specification, the drawings, the claims, and the like and objects other than these can be derived from the description of the specification, the drawings, the claims, and the like.

Means for Solving the Problems

One embodiment of the present invention is an organic compound represented by General Formula (G1) below.

[Chemical 1]

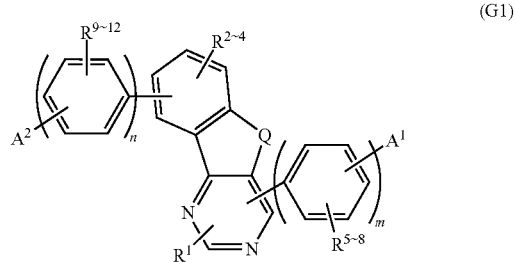

(G1)

In General Formula (G1) above, Q represents oxygen or sulfur. Each of $A^1$ and $A^2$ independently represents a substituted or unsubstituted polycyclic aromatic hydrocarbon. Furthermore, m represents any one of integers from 0 to 4. Furthermore, n represents any one of integers from 1 to 4. Each of $R^1$ to $R^{12}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

Another embodiment of the present invention is an organic compound represented by General Formula (G2) below.

[Chemical 2]

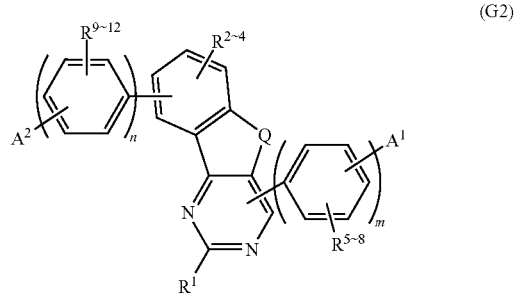

(G2)

In General Formula (G2) above, Q represents oxygen or sulfur. Each of $A^1$ and $A^2$ independently represents a substituted or unsubstituted polycyclic aromatic hydrocarbon. Furthermore, m represents any one of integers from 0 to 4. Furthermore, n represents any one of integers from 1 to 4. Each of $R^1$ to $R^{12}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

Another embodiment of the present invention is an organic compound represented by General Formula (G3) below.

[Chemical 3]

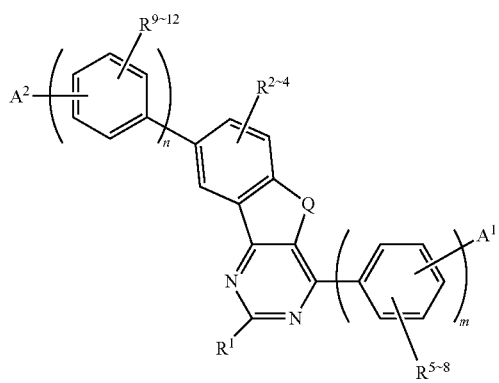

(G3)

In General Formula (G3) above, Q represents oxygen or sulfur. Each of $A^1$ and $A^2$ independently represents a substituted or unsubstituted polycyclic aromatic hydrocarbon. Furthermore, m represents any one of integers from 0 to 4. Furthermore, n represents any one of integers from 1 to 4. Each of $R^1$ to $R^{12}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

Note that each of the above structures is characterized in that each of $A^1$ and $A^2$ in General Formula (G1), General Formula (G2), or General Formula (G3) is independently any one of a substituted or unsubstituted fluorenyl group, a substituted or unsubstituted spirofluorenyl group, a substituted or unsubstituted phenanthrenyl group, and a substituted or unsubstituted triphenylenyl group.

Each of the above structures is characterized in that each of $A^1$ and $A^2$ in General Formula (G1), General Formula (G2), or General Formula (G3) is independently any one of General Formula (A-1) to General Formula (A-14) below.

[Chemical 4]

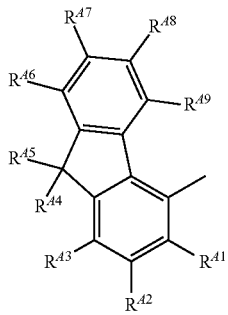

(A-1)

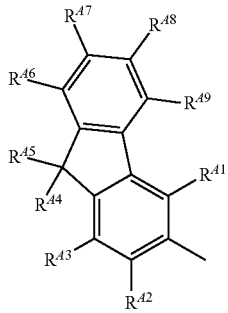

(A-2)

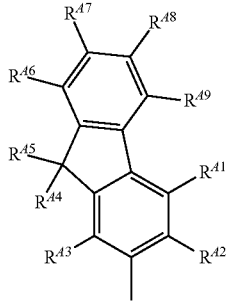

(A-3)

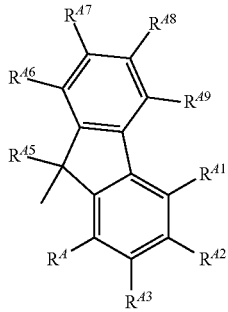

(A-4)

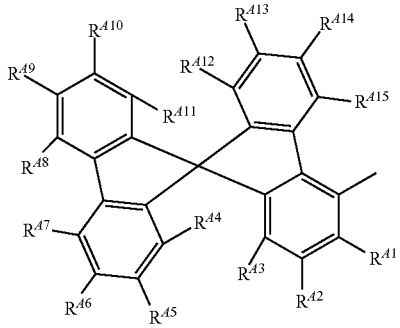

(A-5)

(A-6)
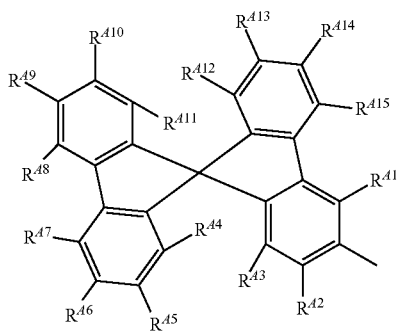

(A-7)
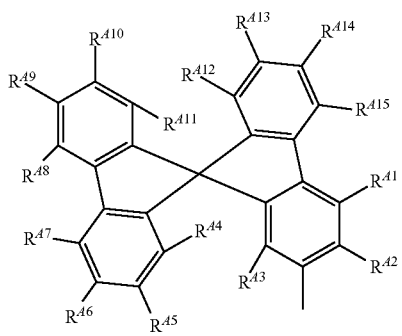

(A-8)
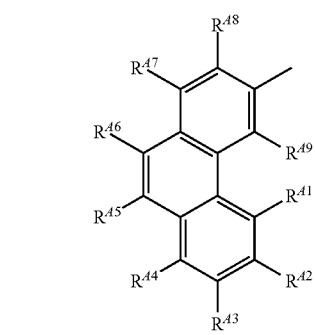

(A-9)
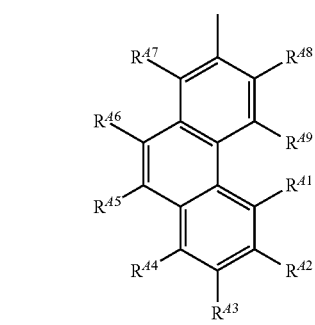

(A-10)
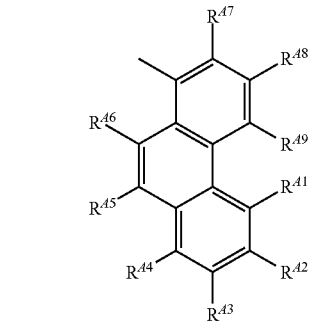

(A-11)
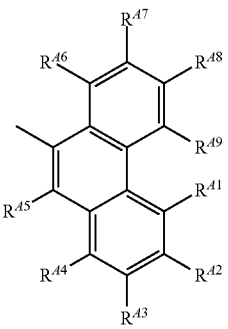

(A-12)
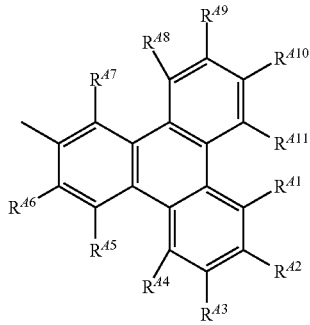

(A-13)
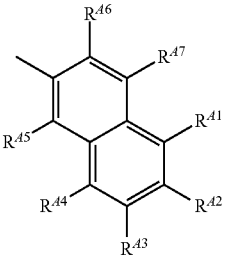

(A-14)
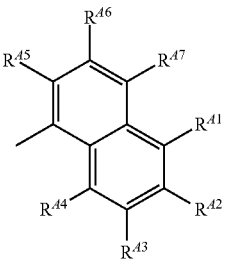

In General Formula (A-1) to General Formula (A-14) above, each of $R^{A1}$ to $R^{A15}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

Another embodiment of the present invention is an organic compound represented by General Formula (G4) below.

[Chemical 5]

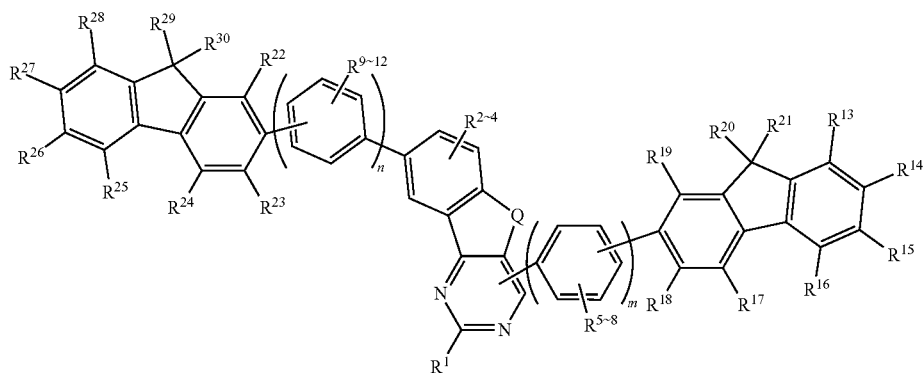

(G4)

In General Formula (G4) above, Q represents oxygen or sulfur. Furthermore, m represents any one of integers from 0 to 4. Furthermore, n represents any one of integers from 1 to 4. Each of $R^1$ to $R^{30}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

Another embodiment of the present invention is an organic compound represented by General Formula (G5) below.

[Chemical 6]

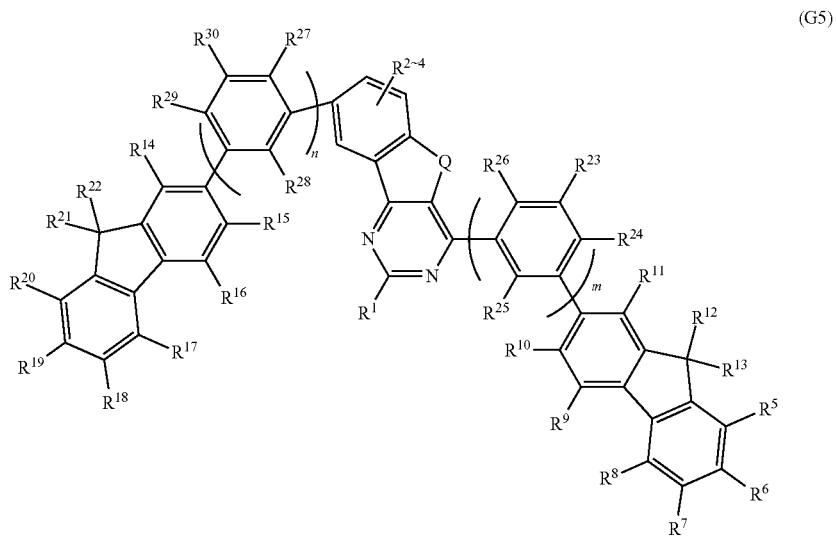

(G5)

In General Formula (G5) above, Q represents oxygen or sulfur. Furthermore, m represents any one of integers from 0 to 4. Furthermore, n represents any one of integers from 1 to 4. Each of $R^1$ to $R^{30}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

Another embodiment of the present invention is an organic compound represented by Structural Formula (100).

[Chemical 7]

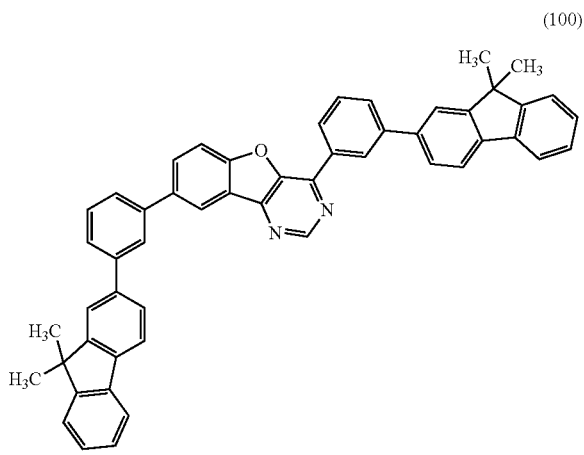

(100)

Another embodiment of the present invention is a light-emitting element in which the above-described organic compound of one embodiment of the present invention is used. Note that the present invention also includes a light-emitting element that is formed using the organic compound of one embodiment of the present invention for an EL layer between a pair of electrodes and a light-emitting layer in the EL layer. In addition to the light-emitting elements, a light-emitting device including a transistor, a substrate, and the like is also included in the scope of the invention. Furthermore, in addition to the light-emitting device, an electronic device and a lighting device that include a microphone, a camera, an operation button, an external connection portion, a housing, a cover, a support, a speaker, or the like are also included in the scope of the invention.

In addition, the scope of one embodiment of the present invention includes a light-emitting device including a light-emitting element, and a lighting device including the light-emitting device. Accordingly, the light-emitting device in this specification refers to an image display device or a light source (including a lighting device). In addition, a light-emitting device includes a module in which a light-emitting device is connected to a connector such as an FPC (Flexible printed circuit) or a TCP (Tape Carrier Package), a module in which a printed wiring board is provided on the tip of a TCP, or a module in which an IC (integrated circuit) is directly mounted on a light-emitting element by a COG (Chip On Glass) method.

Effect of the Invention

In one embodiment of the present invention, a novel organic compound having a benzofuropyrimidine skeleton or a benzothienopyrimidine skeleton and having a polycyclic aromatic hydrocarbon is provided. In another embodiment of the present invention, a benzofuropyrimidine derivative or a benzothienopyrimidine derivative that is a novel organic compound is provided. In one embodiment of the present invention, a novel organic compound that can be used in a light-emitting element is provided. In one embodiment of the present invention, a novel organic compound that can be used in an EL layer of a light-emitting element is provided. In addition, a highly reliable and novel light-emitting element using a novel organic compound of one embodiment of the present invention is provided. In addition, a novel light-emitting device, a novel electronic device, or a novel lighting device is provided. Note that the descriptions of the effects do not disturb the existence of other effects. One embodiment of the present invention does not have to have all of these effects. Effects other than these will be apparent from the description of the specification, the drawings, the claims, and the like and effects other than these can be derived from the description of the specification, the drawings, the claims, and the like.

BRIEF DESCRIPTION OF THE DRAWINGS

FIGS. 4A-4G are drawings illustrating electronic devices.

MODE FOR CARRYING OUT THE INVENTION

Figure 1A:
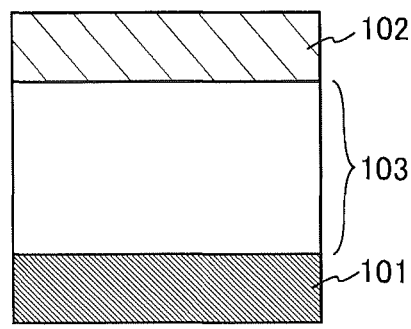
FIGS. 1A-1E are drawings illustrating structures of light-emitting elements.

Embodiments of the present invention will be described below in detail with reference to the drawings. However, the present invention is not limited to the following description, and the modes and details can be various changed without departing from the spirit and scope of the present invention. Thus, the present invention should not be construed as being limited to the description in the following embodiments.

Note that the position, size, range, or the like of each structure illustrated in the drawings and the like do not represent the actual position, size, range, or the like in some cases for easy understanding. Therefore, the disclosed invention is not necessarily limited to the position, size, range, or the like disclosed in the drawings and the like.

Furthermore, when describing the structures of the invention with reference to the drawings in this specification and the like, the reference numerals denoting the same components are commonly used in different drawings.

Embodiment 1

In this embodiment, organic compounds of embodiments of the present invention will be described. Note that an organic compound of one embodiment of the present invention is a benzofuropyrimidine derivative or a benzothienopyrimidine derivative represented by General Formula (G1) below. Note that an organic compound of one embodiment of the present invention has a high T1 level and is thus suitable as a host material for a phosphorescent material.

[Chemical 8]

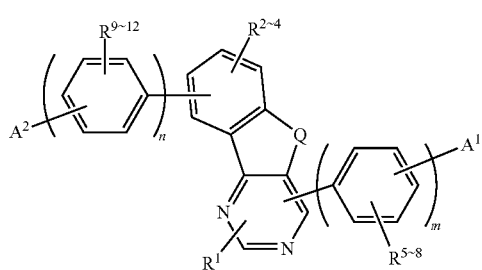

(G1)

In General Formula (G1), Q represents oxygen or sulfur. Each of $A^1$ and $A^2$ independently represents a substituted or unsubstituted polycyclic aromatic hydrocarbon. Furthermore, m represents any one of integers from 0 to 4. Furthermore, n represents any one of integers from 1 to 4. Each of $R^1$ to $R^{12}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

Another embodiment of the present invention is an organic compound represented by General Formula (G2) below.

[Chemical 9]

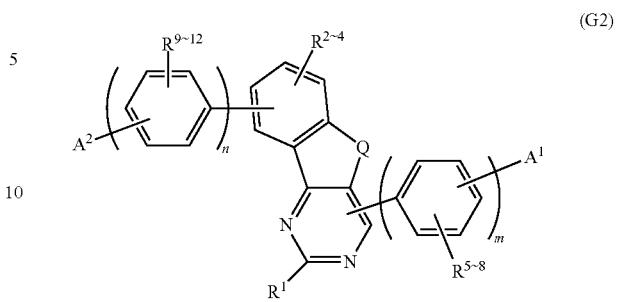

(G2)

In General Formula (G2) above, Q represents oxygen or sulfur. Each of $A^1$ and $A^2$ independently represents a substituted or unsubstituted polycyclic aromatic hydrocarbon. Furthermore, m represents any one of integers from 0 to 4. Furthermore, n represents any one of integers from 1 to 4. Each of $R^1$ to $R^{12}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

Another embodiment of the present invention is an organic compound represented by General Formula (G3) below.

[Chemical 10]

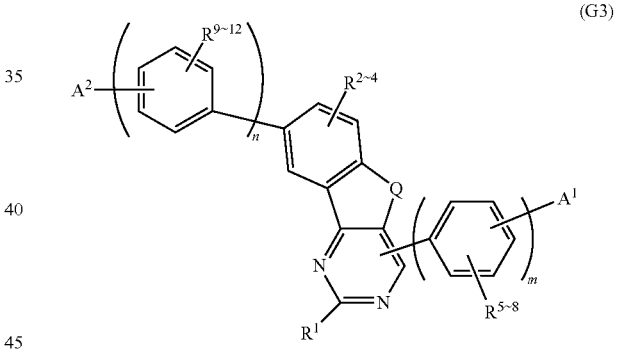

(G3)

In General Formula (G3) above, Q represents oxygen or sulfur. Each of $A^1$ and $A^2$ independently represents a substituted or unsubstituted polycyclic aromatic hydrocarbon. Furthermore, m represents any one of integers from 0 to 4. Furthermore, n represents any one of integers from 1 to 4. Each of $R^1$ to $R^{12}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

Each of $A^1$ and $A^2$ in General Formula (G1), General Formula (G2), or General Formula (G3) above is characterized by being independently any one of a substituted or unsubstituted fluorenyl group, a substituted or unsubstituted spirofluorenyl group, a substituted or unsubstituted phenanthrenyl group, and a substituted or unsubstituted triphenylenyl group.

Each of $A^1$ and $A^2$ in General Formula (G1), General Formula (G2), or General Formula (G3) above is characterized by being independently any one of General Formula (A-1) to General Formula (A-14) below.

[Chemical 11]
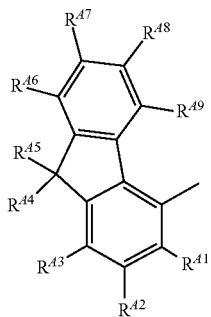
(A-1)
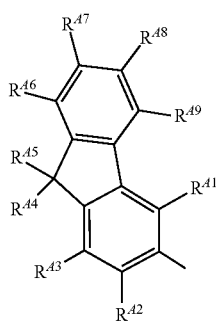
(A-2)
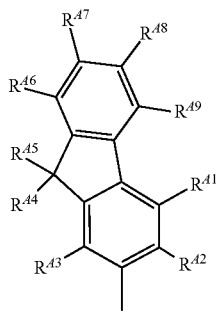
(A-3)
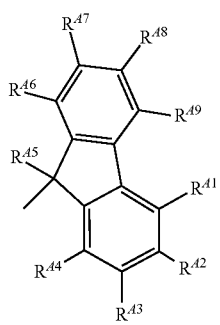
(A-4)
-continued
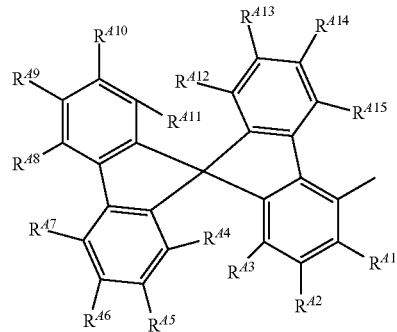
(A-5)
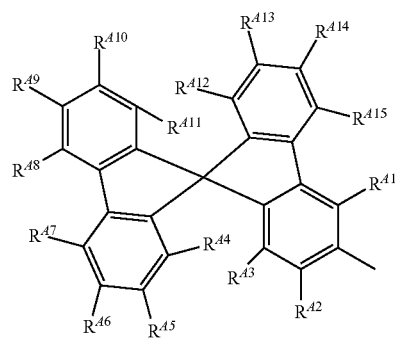
(A-6)
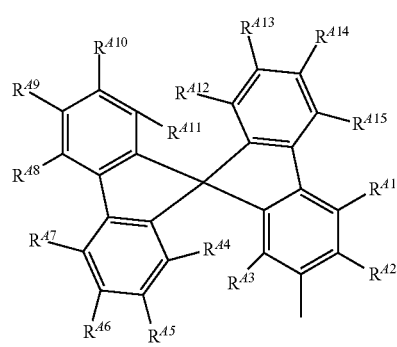
(A-7)
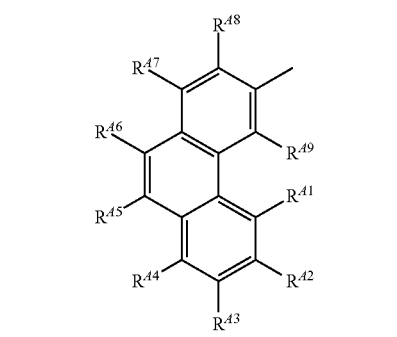
(A-8)

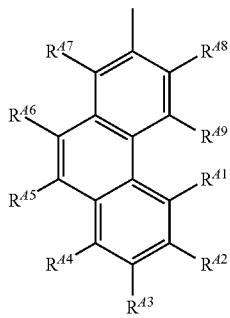 (A-9)

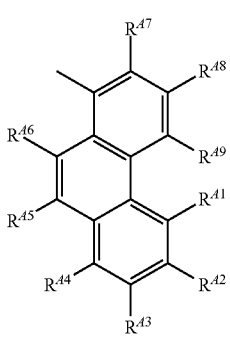 (A-10)

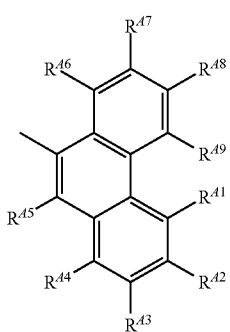 (A-11)

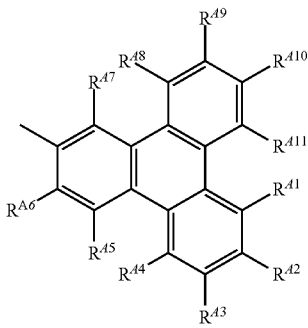 (A-12)

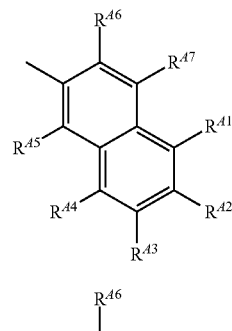 (A-13)

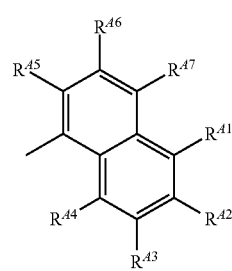 (A-14)

In General Formula (A-1) to General Formula (A-14) above, each of $R^{A1}$ to $R^{A15}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

Another embodiment of the present invention is an organic compound represented by General Formula (G4) below.

[Chemical 12]

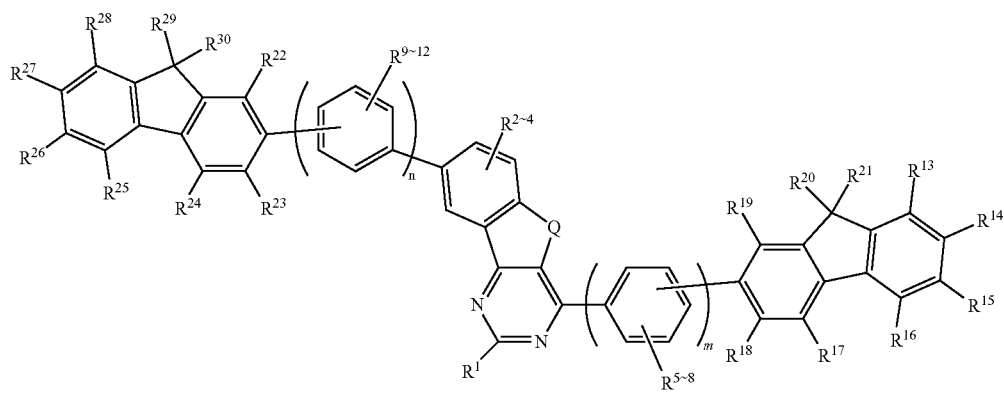 (G4)

In General Formula (G4) above, Q represents oxygen or sulfur. Furthermore, m represents any one of integers from 0 to 4. Furthermore, n represents any one of integers from 1 to 4. Each of $R^1$ to $R^{30}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

Another embodiment of the present invention is an organic compound represented by General Formula (G5) below.

[Chemical 13]

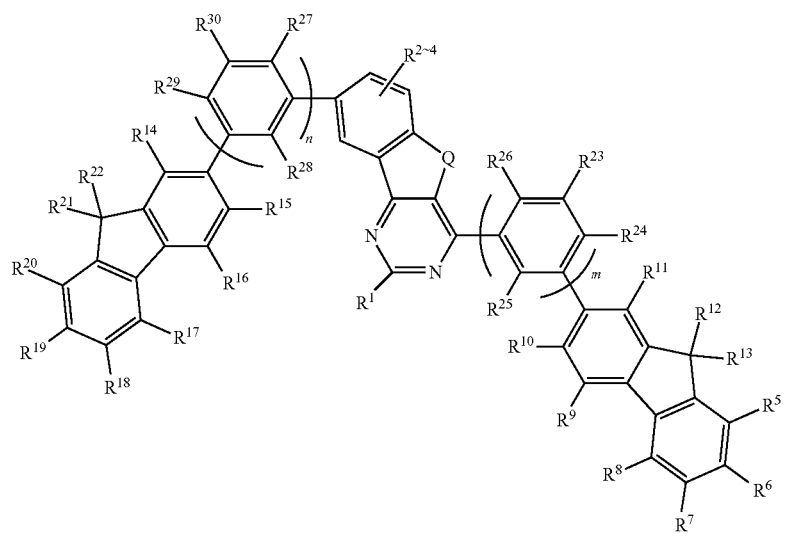

(G5)

Specific examples of the polycyclic aromatic hydrocarbon in General Formula (G1), General Formula (G2), or General Formula (G3) above include a fluorenyl group, a spirofluorenyl group, a phenanthrenyl group, and a triphenylenyl group. As described above, the organic compound of one embodiment of the invention is characterized by including a polycyclic aromatic hydrocarbon with a high T1 level.

Specific examples of the alkyl group having 1 to 6 carbon atoms in General Formula (G1), General Formula (G2), General Formula (G3), General Formula (G4), or General Formula (G5) above include a methyl group, an ethyl group, In General Formula (G5) above, Q represents oxygen or sulfur. Furthermore, m represents any one of integers from 0 to 4. Furthermore, n represents any one of integers from 1 to 4. Each of $R^1$ to $R^{30}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

Note that in the case where the substituted or unsubstituted polycyclic aromatic hydrocarbon, the substituted or unsubstituted cycloalkyl group having 3 to 7 carbon atoms, the substituted or unsubstituted aryl group having 6 to 13 carbon atoms, the substituted or unsubstituted fluorenyl group, the substituted or unsubstituted spirofluorenyl group, the substituted or unsubstituted phenanthrenyl group, or the substituted or unsubstituted triphenylenyl group in General Formula (G1), General Formula (G2), General Formula (G3), General Formula (G4), or General Formula (G5) above has a substituent, examples of the substituent include an alkyl group having 1 to 7 carbon atoms such as a methyl group, an ethyl group, a propyl group, an isopropyl group, a butyl group, an isobutyl group, a sec-butyl group, a tert-butyl group, a pentyl group, or a hexyl group, a cycloalkyl group having 5 to 7 carbon atoms such as a cyclopentyl group, a cyclohexyl group, a cycloheptyl group, or a 8,9,10-trinorbornanyl group, and an aryl group having 6 to 12 carbon atoms such as a phenyl group, a naphthyl group, or a biphenyl group.

a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a 3-methylpentyl group, a 2-methylpentyl group, a 2-ethylbutyl group, a 1,2-dimethylbutyl group, and a 2,3-dimethylbutyl group.

Specific examples of the cycloalkyl group having 3 to 7 carbon atoms in General Formula (G1), General Formula (G2), General Formula (G3), General Formula (G4), or General Formula (G5) above include a cyclopropyl group, a cyclobutyl group, a cyclopentyl group, a cyclohexyl group, a 1-methylcyclohexyl group, a cycloheptyl group, and a norbornanyl group.

Specific examples of the aryl group having 6 to 13 carbon atoms in General Formula (G1), General Formula (G2), General Formula (G3), General Formula (G4), or General Formula (G5) above include a phenyl group, an o-tolyl group, a m-tolyl group, a p-tolyl group, a mesityl group, an o-biphenyl group, a m-biphenyl group, a p-biphenyl group, a 1-naphthyl group, a 2-naphthyl group, and a fluorenyl group.

Next, specific structural formulae of the above-described organic compounds of embodiments of the present invention are shown below. Note that the present invention is not limited to these formulae.

[Chemical 14]
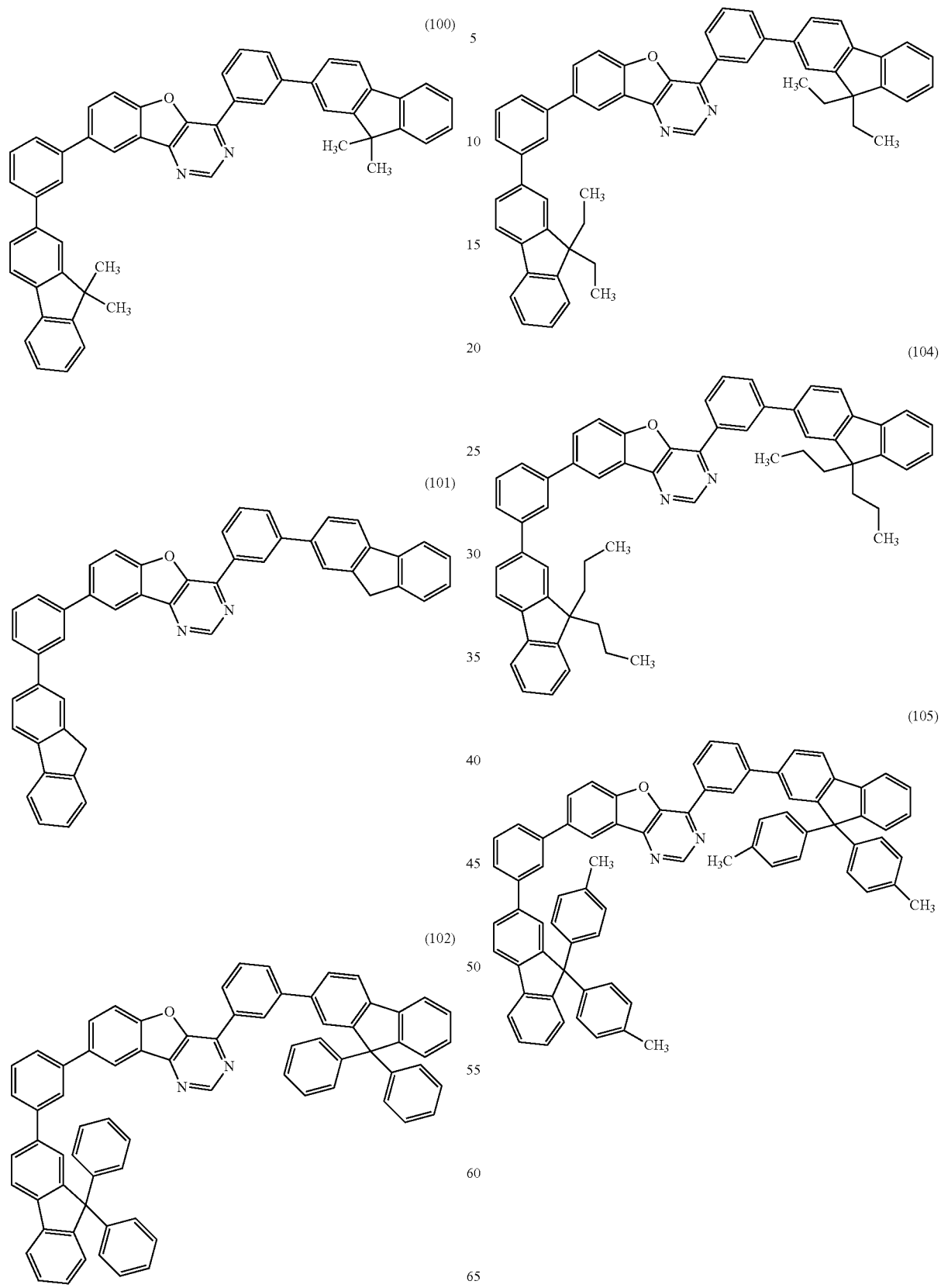

(106)
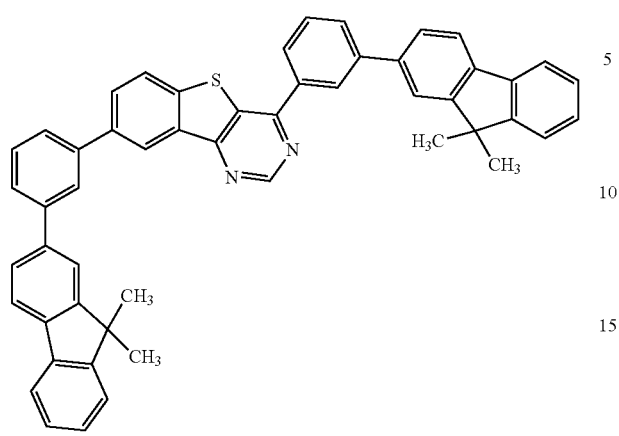
(107)
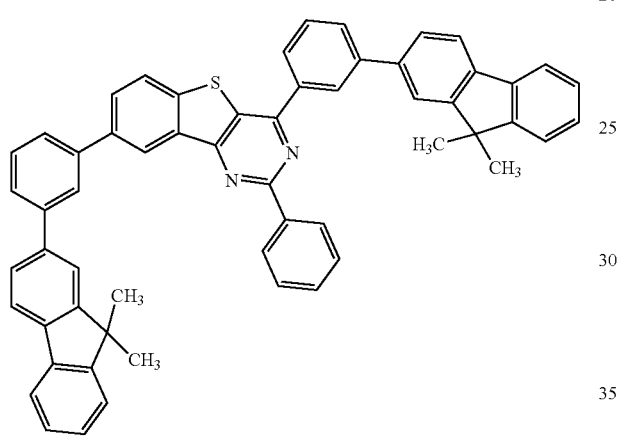
[Chemical 15]
(108)
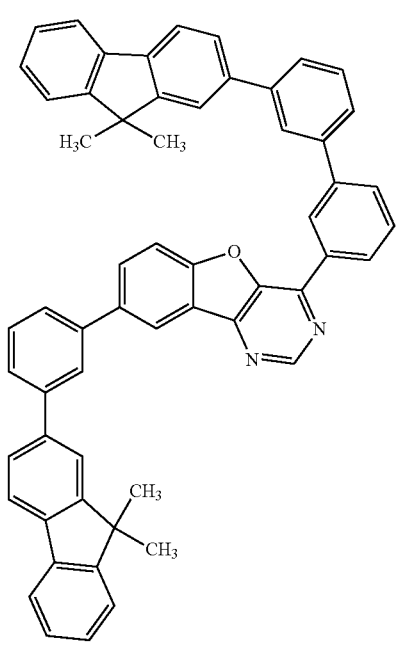
(109)
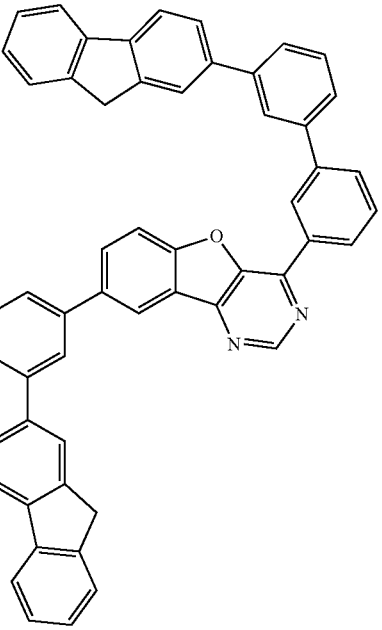
(110)
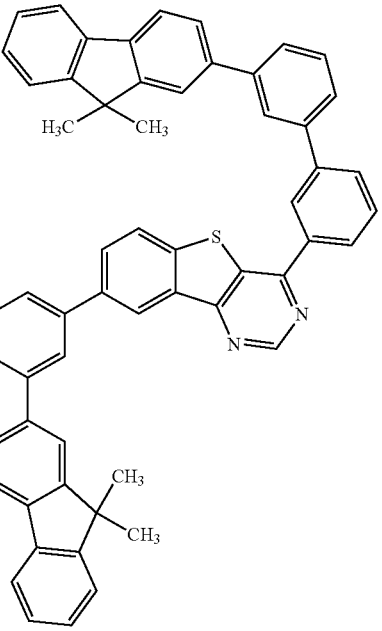

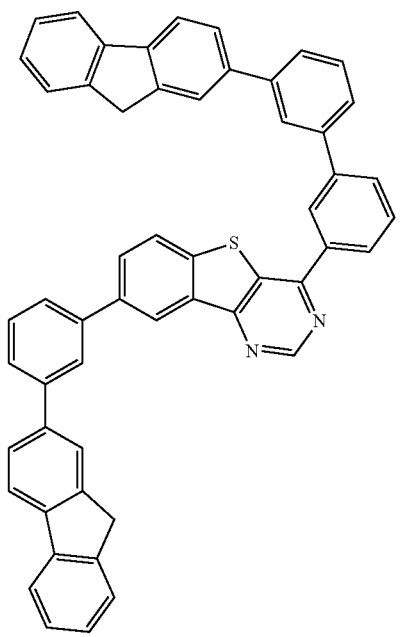
(111)
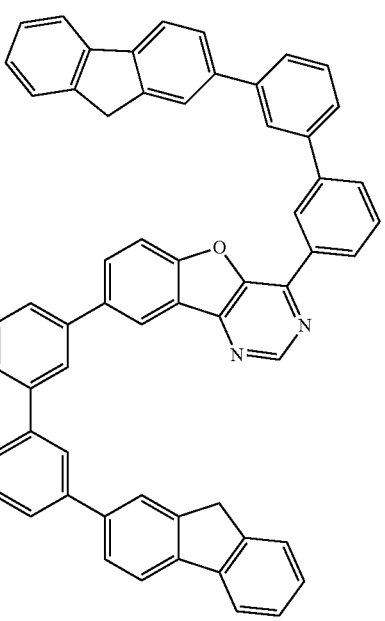
(113)
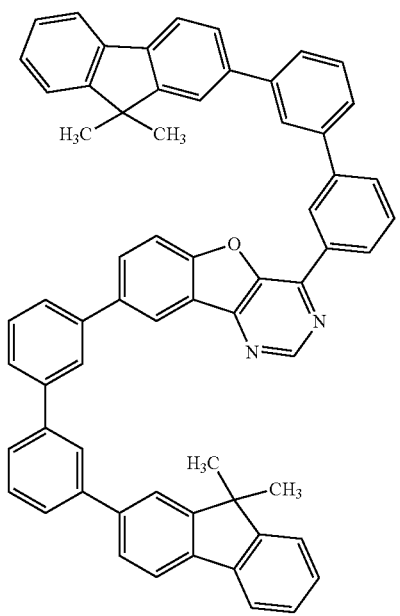
(112)
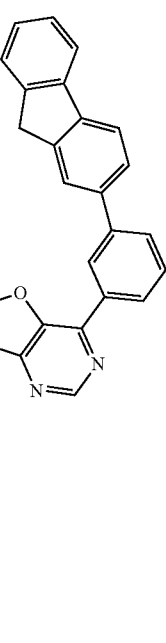
(114)

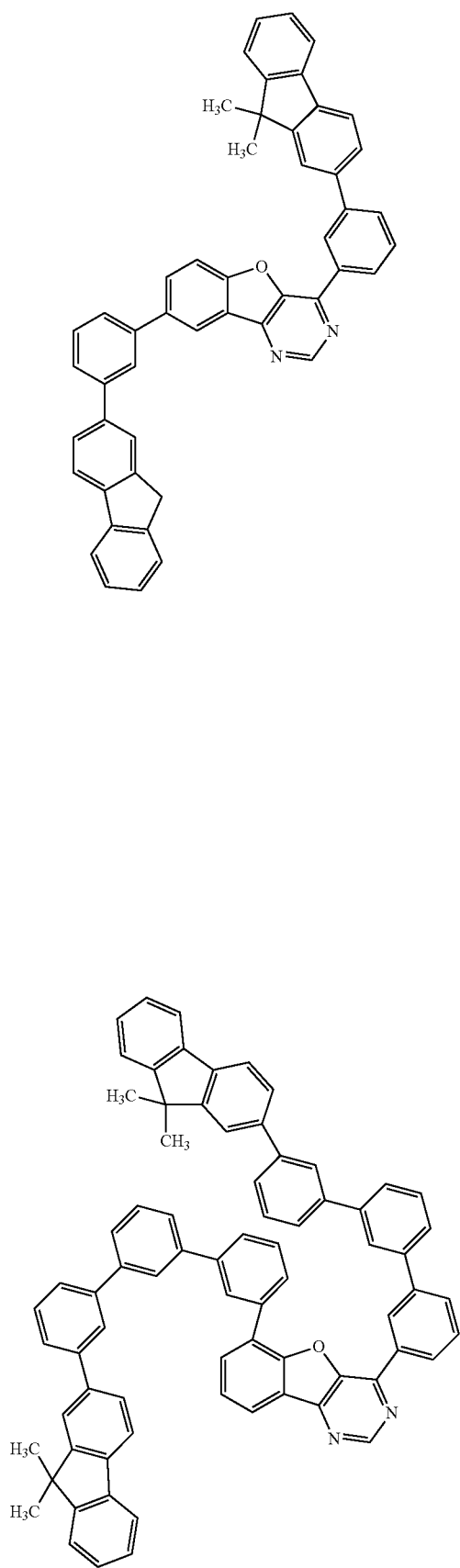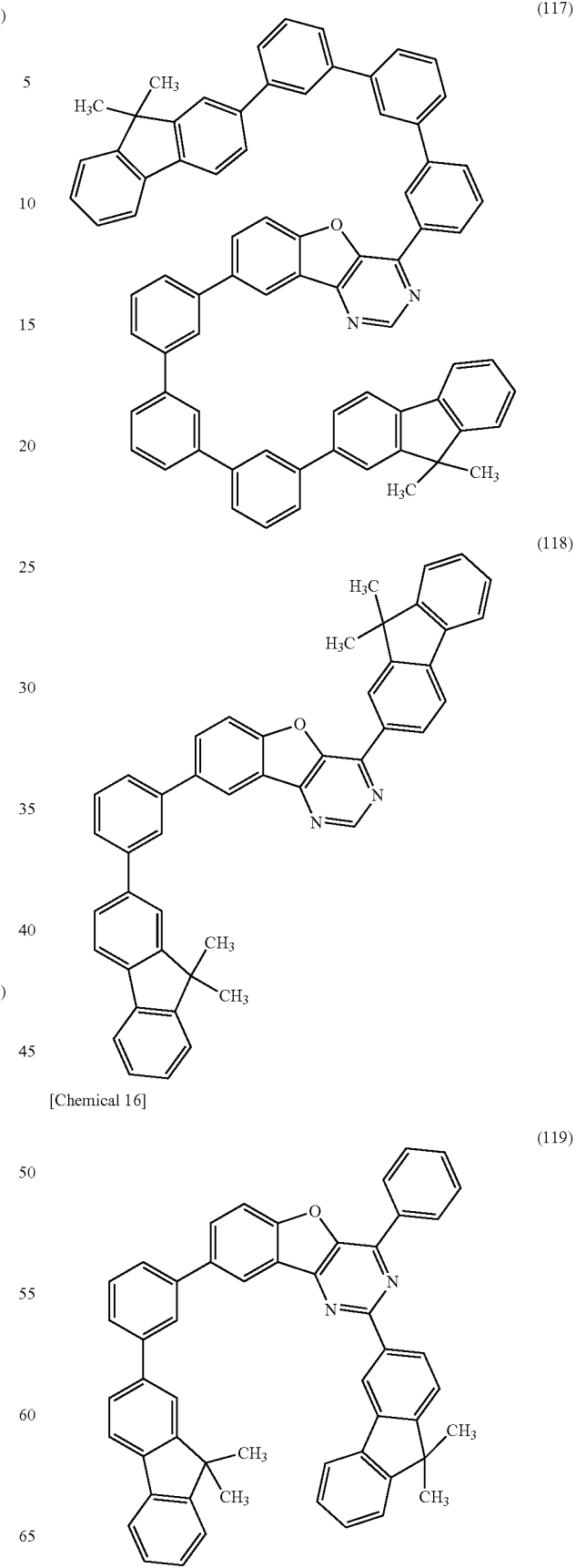

(120)
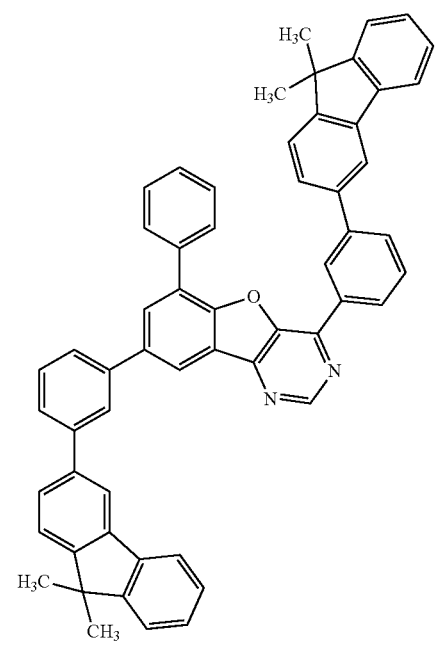
(121)
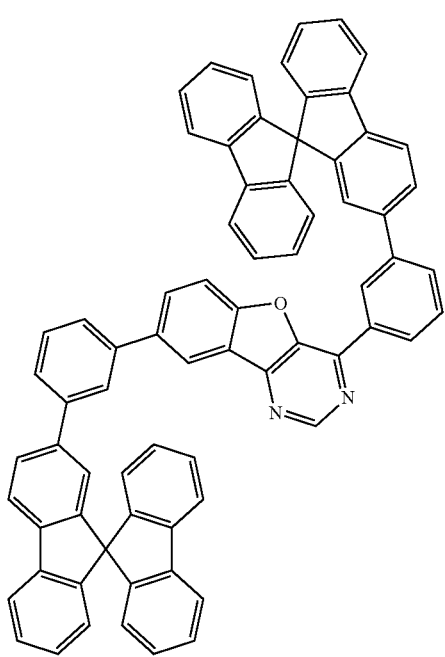
(122)
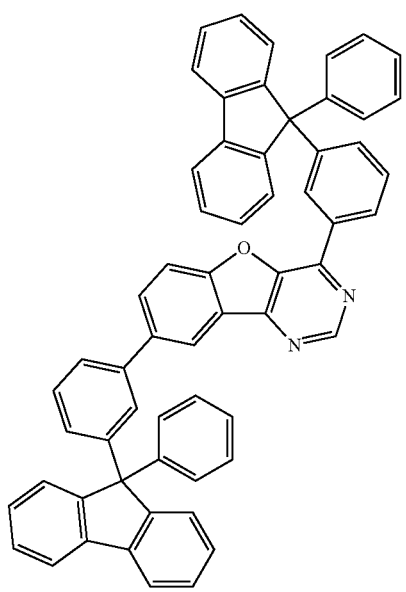
(123)
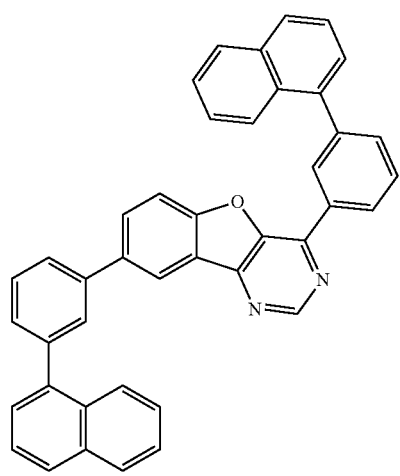
(124)
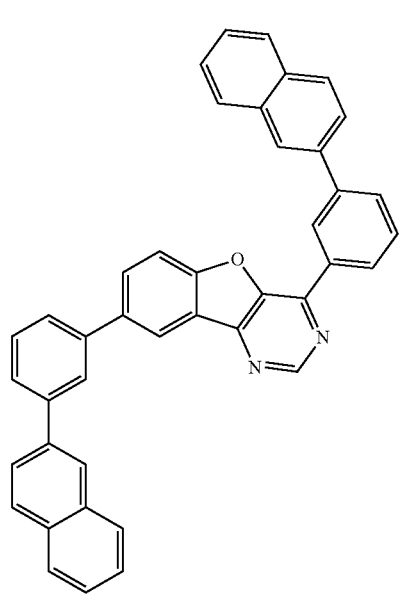

(125)
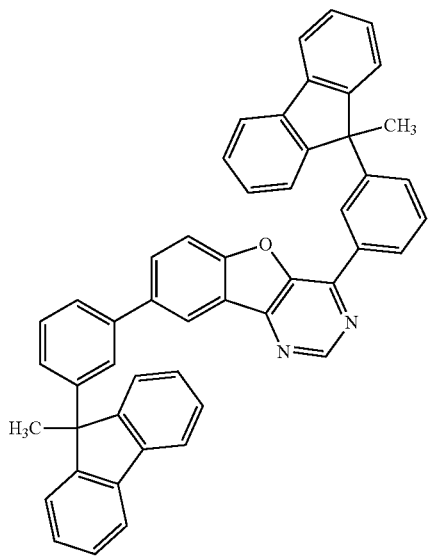
(126)
(127)
(128)
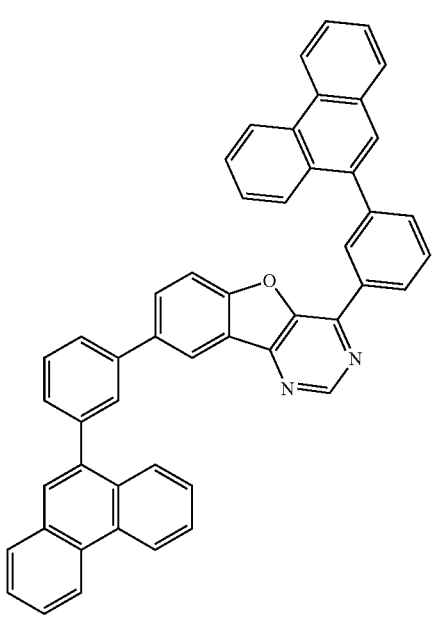
(129)
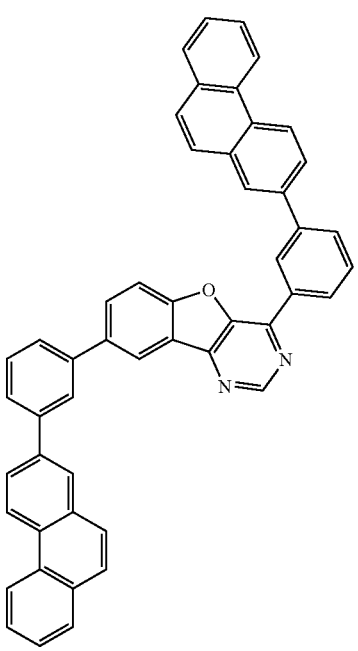

-continued (130)

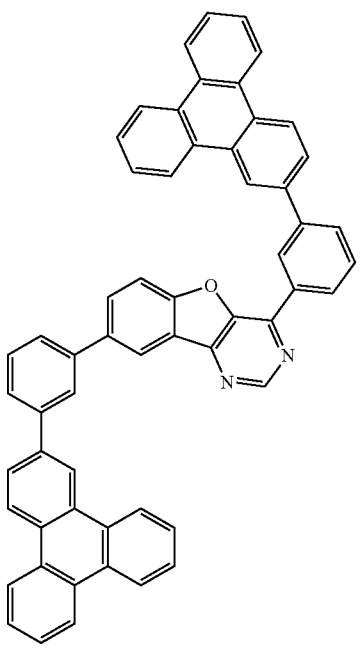

Note that although the organic compounds represented by Structural Formulae (100) to (130) above are examples of the organic compound represented by General Formula (G1), General Formula (G2), General Formula (G3), General Formula (G4), or General Formula (G5) above, the organic compound of one embodiment of the present invention is not limited to these examples.

Next, a method for synthesizing the organic compound which is one embodiment of the present invention and is represented by General Formula (G1) below will be described.

[Chemical 17]

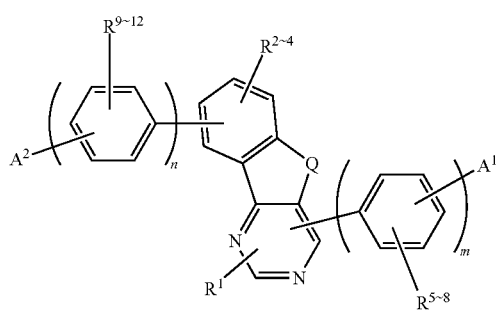

(G1)

In General Formula (G1), Q represents oxygen or sulfur. Each of $A^1$ and $A^2$ independently represents a substituted or unsubstituted polycyclic aromatic hydrocarbon. Furthermore, m represents any one of integers from 0 to 4. Furthermore, n represents any one of integers from 1 to 4. Each of $R^1$ to $R^{12}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

<<Method for Synthesizing Organic Compound Represented by General Formula (G)>>

A variety of reactions can be used for the synthesis of the organic compound represented by General Formula (G1) above; for example, the organic compound represented by General Formula (G1) can be synthesized by a simple method shown by synthesis schemes below.

First, as shown in Scheme (A) below, a dihalogen compound (a1) and boronic acid compounds (a2) and (a3) are made to react with each other, whereby the organic compound represented by General Formula (G1) can be obtained. Note that the dihalogen compound (a1) has a substituted or unsubstituted benzofuropyrimidine skeleton or benzothienopyrimidine skeleton. The boronic acid compounds (a2) and (a3) each have a substituted or unsubstituted polycyclic aromatic hydrocarbon.

[Chemical 18]

(A)

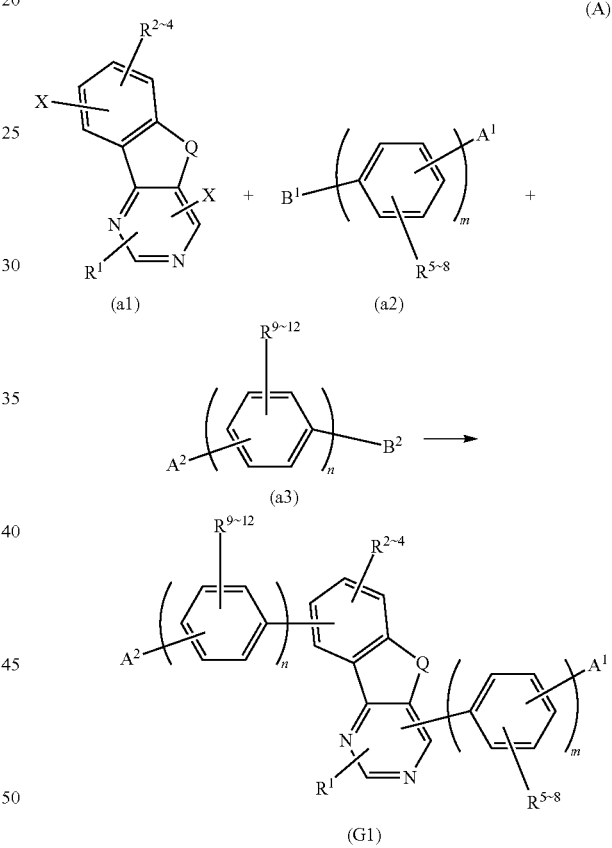

Note that in Synthesis Scheme (A) above, X represents a halogen and Q represents oxygen or sulfur. Furthermore, each of $A^1$ and $A^2$ independently represents a substituted or unsubstituted polycyclic aromatic hydrocarbon. In addition, $B^1$ and $B^2$ each represent a boronic acid, a boronic ester, a cyclic-triolborate salt, or the like. As the cyclic-triolborate salt, a lithium salt, a potassium salt, or a sodium salt may be used. Furthermore, m represents any one of integers from 0 to 4. Furthermore, n represents any one of integers from 1 to 4. Each of $R^1$ to $R^{12}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

The organic compound represented by General Formula (G1) can also be obtained in such a manner that as shown in Scheme (B) below, an intermediate (d1) is obtained through reaction between the dihalogen compound (a1) and boronic acid compounds (b1) and (b2) and then, boronic acid compounds (b3) and (b4) are made to react with each other. Note that the dihalogen compound (a1) has a substituted or unsubstituted benzofuropyrimidine skeleton or benzothienopyrimidine skeleton. The boronic acid compounds (b1) and (b2) have a substituted or unsubstituted phenyl group. The boronic acid compounds (b3) and (b4) each have a substituted or unsubstituted polycyclic aromatic hydrocarbon group.

substituted or unsubstituted cycloalkyl group having 3 to 7 carbon atoms, and a substituted or unsubstituted aryl group having 6 to 13 carbon atoms.

As shown in Scheme (C) below, the organic compound represented by General Formula (G1) can also be obtained by causing reaction between a halogen compound (c1) and the boronic acid compound (a2). Note that the halogen compound (c1) has a benzofuropyrimidine skeleton or a benzothienopyrimidine skeleton that includes a substituted or unsubstituted polycyclic aromatic hydrocarbon. The boronic acid compound (a2) has a phenyl group that includes a substituted or unsubstituted polycyclic aromatic hydrocarbon.

[Chemical 19]

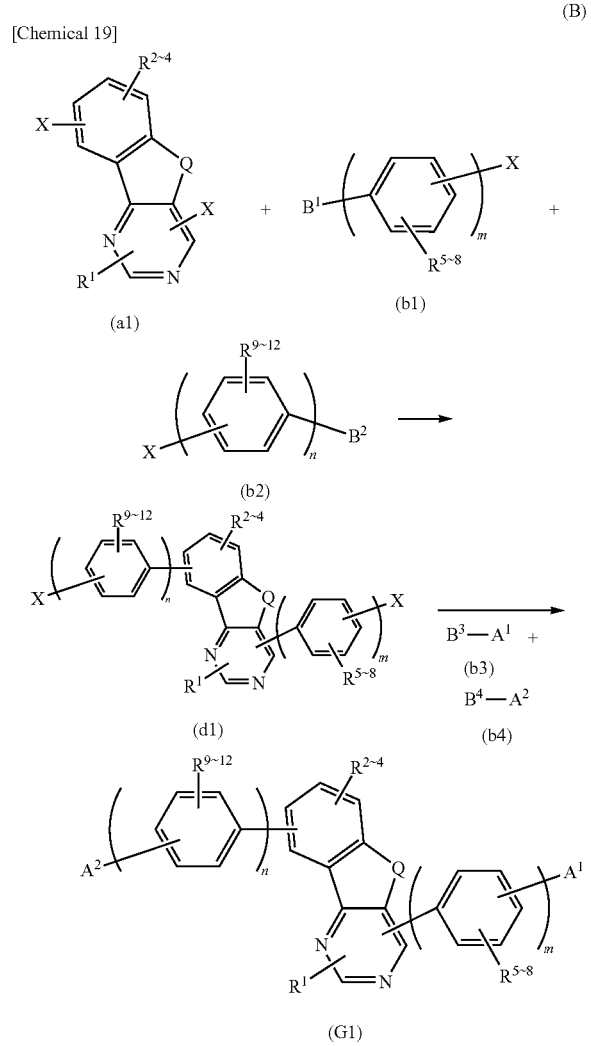

[Chemical 20]

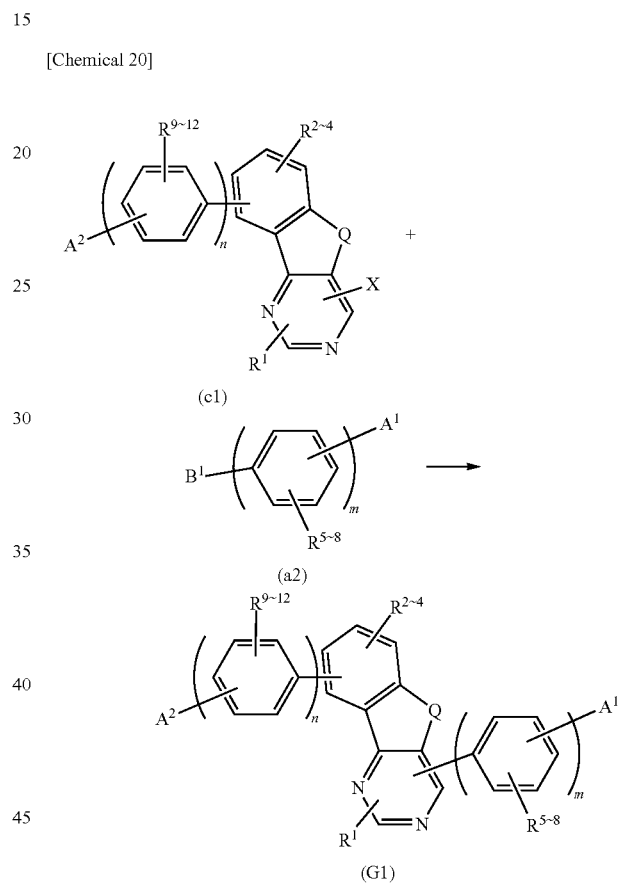

Note that in Synthesis Scheme (B) above, X represents a halogen and Q represents oxygen or sulfur. Furthermore, each of $A^1$ and $A^2$ independently represents a substituted or unsubstituted polycyclic aromatic hydrocarbon. In addition, $B^1$ to $B^4$ each represent a boronic acid, a boronic ester, a cyclic-triolborate salt, or the like. As the cyclic-triolborate salt, a lithium salt, a potassium salt, or a sodium salt may be used. Furthermore, m represents any one of integers from 0 to 4. Furthermore, n represents any one of integers from 1 to 4. Each of $R^1$ to $R^{12}$ independently represents any one of hydrogen, an alkyl group having 1 to 6 carbon atoms, a Note that in Synthesis Scheme (C) above, X represents a halogen and Q represents oxygen or sulfur. Furthermore, each of $A^1$ and $A^2$ independently represents a substituted or unsubstituted polycyclic aromatic hydrocarbon. In addition, $B^1$ represents a boronic acid, a boronic ester, a cyclic-triolborate salt, or the like. As the cyclic-triolborate salt, a lithium salt, a potassium salt, or a sodium salt may be used. Furthermore, m represents any one of integers from 0 to 4. Furthermore, n represents any one of integers from 1 to 4. Each of $R^1$ to $R^{12}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

Note that various kinds of the dihalogen compound (a1), the boronic acid compounds (a2) and (a3), the boronic acid compounds (b1) and (b2), the boronic acid compounds (b3) and (b4), and the halogen compound (c1) used in Synthesis Schemes (A), (B), and (C) above are commercially available or can be synthesized; accordingly, many kinds of the benzofuropyrimidine derivatives or benzothienopyrimidine derivatives represented by General Formula (G1) can be synthesized. Thus, the compound of one embodiment of the present invention is characterized by having numerous variations.

Described above are the organic compounds of embodiments of the present invention and examples of their synthesis method; however, the present invention is not limited thereto and the organic compounds may be synthesized by another synthesis method.

The structures described in this embodiment can be used in an appropriate combination with the structures described in the other embodiments.

Embodiment 2

In this embodiment, a light-emitting element in which the organic compound described in Embodiment 1 is used will be described with reference to FIG. 1.

<<Basic Structure of Light-Emitting Element>>

First, a basic structure of a light-emitting element will be described. FIG. 1(A) illustrates an example of a light-emitting element including, between a pair of electrodes, an EL layer having a light-emitting layer. Specifically, the light-emitting element has a structure in which an EL layer 103 is sandwiched between a first electrode 101 and a second electrode 102.

Figure 1B:
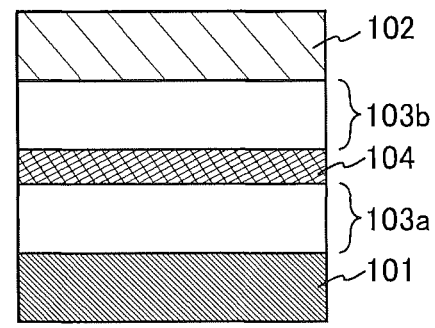

FIG. 1(B) illustrates an example of a light-emitting element with a stacked-layer structure (tandem structure) in which a plurality of (two layers, in FIG. 1(B)) EL layers (103a and 103b) are provided between a pair of electrodes and a charge-generation layer 104 is provided between the EL layers. With a tandem light-emitting element, a light-emitting device that can be driven at low voltage with low power consumption can be obtained.

The charge-generation layer 104 has a function of injecting electrons into one of the EL layers (103a or 103b) and injecting holes into the other of the EL layers (103b or 103a) when voltage is applied to the first electrode 101 and the second electrode 102. Thus, when voltage is applied in FIG. 1(B) such that the potential of the first electrode 101 is higher than that of the second electrode 102, the charge-generation layer 104 injects electrons into the EL layer 103a and injects holes into the EL layer 103b.

Note that in terms of light extraction efficiency, the charge-generation layer 104 preferably has a light-transmitting property with respect to visible light (specifically, the visible light transmittance with respect to the charge-generation layer 104 is 40% or higher). Furthermore, the charge-generation layer 104 functions even when having lower conductivity than the first electrode 101 or the second electrode 102.

Figure 1C:
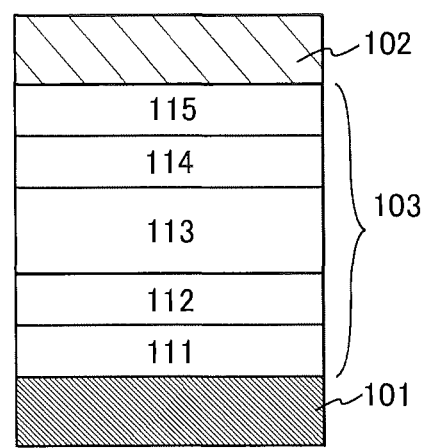
Figure 1D:
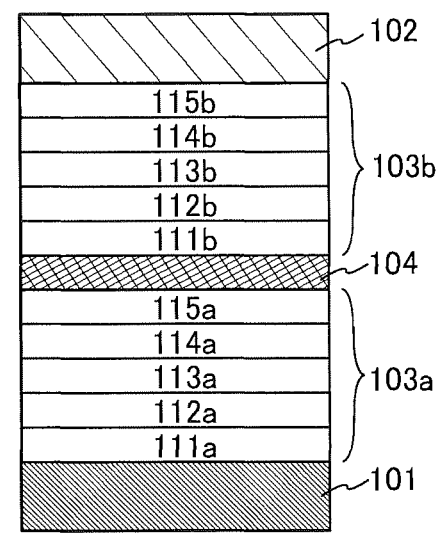

FIG. 1(C) illustrates an example of the case where the EL layer 103 illustrated in FIG. 1(A) has a stacked-layer structure (which also applies to the case where the EL layers (103a and 103b) in FIG. 1(B) have stacked-layer structures). Note that in this case, the first electrode 101 is regarded as functioning as an anode. The EL layer 103 has a structure in which a hole-injection layer 111, a hole-transport layer 112, a light-emitting layer 113, an electron-transport layer 114, and an electron-injection layer 115 are stacked sequentially over the first electrode 101. Note that when a plurality of EL layers are provided as in FIG. 1(B), each EL layer has a structure in which the layers are sequentially stacked from the anode side. When the first electrode 101 is a cathode and the second electrode 102 is an anode, the stacking order in the EL layer is reversed.

The light-emitting layers 113 included in the EL layers (103, 103a, and 103b) each contain an appropriate combination of a light-emitting substance and a plurality of substances, so that fluorescence or phosphorescence with a desired emission color can be obtained. Furthermore, the light-emitting layer 113 may have a stacked-layer structure having different emission colors. In that case, different materials may be used for the light-emitting substance and other substances used in each of the light-emitting layers that are stacked. Furthermore, a structure in which different emission colors can be obtained from the plurality of EL layers (103a and 103b) shown in FIG. 1(B) may be employed. Also in that case, different materials may be used for the light-emitting substance and other substances used in each of the light-emitting layers.

In addition, the light-emitting element of one embodiment of the present invention can have a micro optical resonator (microcavity) structure with the first electrode 101 being a reflective electrode and the second electrode 102 being a semi-transmissive semi-reflective electrode in FIG. 1(C), for example, and light emission obtained from the light-emitting layer 113 in the EL layer 103 can be resonated between the electrodes and light emission obtained through the second electrode 102 can be intensified.

Note that when the first electrode 101 of the light-emitting element is a reflective electrode having a stacked structure of a reflective conductive material and a light-transmitting conductive material (transparent conductive film), optical adjustment can be performed by adjusting the thickness of the transparent conductive film. Specifically, when the wavelength of light obtained from the light-emitting layer 113 is X, the distance between the first electrode 101 and the second electrode 102 is preferably adjusted to around $m\lambda/2$ (m is a natural number).

To amplify desired light (wavelength: $\lambda$) obtained from the light-emitting layer 113, the optical path length from the first electrode 101 to a region where the desired light is obtained in the light-emitting layer 113 (light-emitting region) and the optical path length from the second electrode 102 to the region where the desired light is obtained in the light-emitting layer 113 (light-emitting region) are preferably adjusted to around $(2m'+1)\lambda/4$ (m' is a natural number). Here, the light-emitting region refers to a region where holes and electrons are recombined in the light-emitting layer 113.

By performing such optical adjustment, the spectrum of specific monochromatic light obtained from the light-emitting layer 113 can be narrowed and light emission with high color purity can be obtained.

However, in the above case, the optical path length between the first electrode 101 and the second electrode 102 is, to be exact, the total thickness from a reflective region in the first electrode 101 to a reflective region in the second electrode 102. However, it is difficult to precisely determine the reflective regions in the first electrode 101 and the second electrode 102; thus, it is assumed that the above effect can be sufficiently obtained with given positions in the first electrode 101 and the second electrode 102 being supposed to be reflective regions. Furthermore, the optical path length between the first electrode 101 and the light-emitting layer from which the desired light is obtained is, to be exact, the optical path length between the reflective region in the first electrode 101 and the light-emitting region in the light-emitting layer from which the desired light is obtained. However, it is difficult to precisely determine the reflective region in the first electrode 101 and the light-emitting region in the light-emitting layer from which the desired light is obtained; thus, it is assumed that the above effect can be sufficiently obtained with a given position in the first electrode 101 being supposed to be the reflective region and a given position in the light-emitting layer from which the desired light is obtained being supposed to be the light-emitting region.

In the case where the light-emitting element in FIG. 1(C) has a microcavity structure, light (monochromatic light) with different wavelengths can be extracted even if the same EL layer is included. Thus, separate coloring for obtaining different emission colors (e.g., R, G, and B) is not necessary. Furthermore, high resolution can be easily achieved. A combination with coloring layers (color filters) is also possible. Furthermore, emission intensity of light with a specific wavelength in the front direction can be increased, whereby power consumption can be reduced.

Figure 1E:
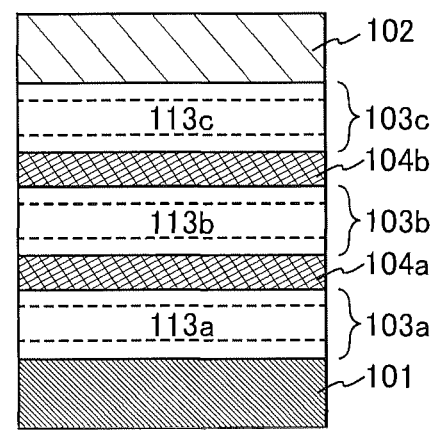

A light-emitting element illustrated in FIG. 1(E) is an example of the light-emitting element with the tandem structure illustrated in FIG. 1(B), and includes three EL layers (103a, 103b, and 103c) stacked with charge-generation layers (104a and 104b) sandwiched therebetween, as illustrated in the drawing. Note that the three EL layers (103a, 103b, and 103c) include respective light-emitting layers (113a, 113b, and 113c) and the emission colors of the respective light-emitting layers can be combined freely. For example, the light-emitting layer 113a can be blue, the light-emitting layer 113b can be red, green, or yellow, and the light-emitting layer 113c can be blue; for another example, the light-emitting layer 113a can be red, the light-emitting layer 113b can be blue, green, or yellow, and the light-emitting layer 113c can be red.

In the above light-emitting element of one embodiment of the present invention, at least one of the first electrode 101 and the second electrode 102 is a light-transmitting electrode (a transparent electrode, a semi-transmissive semi-reflective electrode, or the like). In the case where the light-transmitting electrode is a transparent electrode, the visible light transmittance of the transparent electrode is 40% or higher. In the case where the light-transmitting electrode is a semi-transmissive semi-reflective electrode, the visible light reflectance of the semi-transmissive semi-reflective electrode is higher than or equal to 20% and lower than or equal to 80%, preferably higher than or equal to 40% and lower than or equal to 70%. The resistivity of these electrodes is preferably $1\times10^{-2}$ Ωcm or lower.

Furthermore, when one of the first electrode 101 and the second electrode 102 is a reflective electrode in the above light-emitting element of one embodiment of the present invention, the visible light reflectance of the reflective electrode is higher than or equal to 40% and lower than or equal to 100%, preferably higher than or equal to 70% and lower than or equal to 100%. The resistivity of this electrode is preferably $1\times10^{-2}$ Ωcm or lower.

<<Specific Structure and Fabrication Method of Light-Emitting Element>>

Next, specific structures and fabrication methods of the light-emitting elements of embodiments of the present invention illustrated in FIG. 1 will be described. Note that here, collective description is made on a light-emitting element with a tandem structure illustrated in FIG. 1(B), FIG. 1(D), and FIG. 1(E) in addition to the light-emitting element whose EL layer 103 has a single-layer structure as illustrated in FIG. 1(A) and FIG. 1(C). In the case where the light-emitting element shown in FIG. 1 has a microcavity structure, the first electrode 101 is formed as a reflective electrode and the second electrode 102 is formed as a semi-transmissive semi-reflective electrode, for example. The electrode can be formed, using one or more kinds of desired electrode materials, as a single layer or a stacked layer. The second electrode 102 is formed after formation of the EL layer (103 or 103b), with the use of a material selected as described above. For fabrication of these electrodes, a sputtering method or a vacuum evaporation method can be used.

<First Electrode and Second Electrode>

As materials for forming the first electrode 101 and the second electrode 102, any of the following materials can be used in an appropriate combination as long as the functions of the electrodes described above can be fulfilled. For example, a metal, an alloy, an electrically conductive compound, a mixture of these, and the like can be used as appropriate. Specifically, an In—Sn oxide (also referred to as ITO), an In—Si—Sn oxide (also referred to as ITSO), an In—Zn oxide, and an In—W—Zn oxide can be given as examples. In addition, it is also possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use an element belonging to Group 1 or Group 2 in the periodic table, which is not listed above (for example, lithium (Li), cesium (Cs), calcium (Ca), or strontium (Sr)), a rare earth metal such as europium (Eu) or ytterbium (Yb), an alloy containing an appropriate combination of any of these elements, graphene, or the like.

When the first electrode 101 is an anode, a hole-injection layer (111 or 111a) and a hole-transport layer (112 or 112a) of the EL layer (103 or 103a) are sequentially formed and stacked over the first electrode 101 by a vacuum evaporation method. In the case of the light-emitting element with the tandem structure illustrated in FIG. 1(D), after the EL layer 103a and the charge-generation layer 104 are sequentially formed, a hole-injection layer 111b and a hole-transport layer 112b of the EL layer 103b are sequentially formed and stacked over the charge-generation layer 104 in a similar manner.

<Hole-Injection Layer and Hole-Transport Layer>

The hole-injection layers (111, 111a, and 111b) are each a layer that injects holes from the first electrode 101 which is an anode and the charge-generation layer (104) to the EL layers (103, 103a, and 103b) and contains a material with a high hole-injection property.

As examples of the material with a high hole-injection property, transition metal oxides such as a molybdenum oxide, a vanadium oxide, a ruthenium oxide, a tungsten oxide, and a manganese oxide can be given. Other than the above, it is possible to use phthalocyanine-based compounds such as phthalocyanine (abbreviation: $H_2Pc$) and copper phthalocyanine (abbreviation: CuPC); aromatic amine compounds such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD); macromolecules such as poly(3,4-ethylenedioxythiophene)/poly(styrenesulfonic acid) (abbreviation: PEDOT/PSS); or the like.

Alternatively, as the material with a high hole-injection property, a composite material containing a hole-transport material and an acceptor material (an electron-accepting material) can be used. In that case, the acceptor material extracts electrons from the hole-transport material, so that holes are generated in the hole-injection layers (111, 111a, and 111b) and the holes are injected into the light-emitting layers (113, 113a, and 113b) through the hole-transport layers (112, 112a, and 112b). Note that each of the hole-injection layers (111, 111a, and 111b) may be formed as a single layer formed of a composite material containing a hole-transport material and an acceptor material (electron-accepting material), or may be formed by stacking a layer including a hole-transport material and a layer including an acceptor material (electron-accepting material).

The hole-transport layers (112, 112a, and 112b) are each a layer that transports the holes, which are injected from the first electrode 101 or the charge-generation layer 104 by the hole-injection layers (111, 111a, and 111b), to the light-emitting layers (113, 113a, and 113b). Note that the hole-transport layers (112, 112a, and 112b) are each a layer containing a hole-transport material. It is particularly preferable that the HOMO level of the hole-transport material used in the hole-transport layers (112, 112a, and 112b) be the same as or close to the HOMO level of the hole-injection layers (111, 111a, and 111b).

As the acceptor material used in the hole-injection layers (111, 111a, and 111b), an oxide of a metal belonging to any of Groups 4 to 8 of the periodic table can be used. Specific examples include molybdenum oxide, vanadium oxide, niobium oxide, tantalum oxide, chromium oxide, tungsten oxide, manganese oxide, and rhenium oxide. Among these, molybdenum oxide is especially preferable since it is stable in the air, has a low hygroscopic property, and is easy to handle. Alternatively, organic acceptors such as a quinodimethane derivative, a chloranil derivative, and a hexaazatriphenylene derivative can be used. As examples of ones having an electron-withdrawing group (a halogen group or a cyano group), 7,7,8,8-tetracyano-2,3,5,6-tetrafluoroquinodimethane (abbreviation: $F_4$-TCNQ), chloranil, 2,3,6,7,10,11-hexacyano-1,4,5,8,9,12-hexaazatriphenylene (abbreviation: HAT-CN), 1,3,4,5,7,8-hexafluorotetracyanonaphthoquinodimethane (abbreviation: $F_6$-TCNNQ), and the like can be given. A compound in which electron-withdrawing groups are bonded to a condensed aromatic ring having a plurality of hetero atoms, such as HAT-CN, is particularly preferable because it is thermally stable. A [3]radialene derivative including an electron-withdrawing group (in particular, a cyano group or a halogen group such as a fluoro group) has a very high electron-accepting property and thus is preferred; specific examples include α,α',α"-1,2,3-cyclopropanetriylidenetris[4-cyano-2,3,5,6-tetrafluorobenzeneacetonitrile], α,α',α"-1,2,3-cyclopropanetriylidenetris[2,6-dichloro-3,5-difluoro-4-(trifluoromethyl)benzeneacetonitrile], and α,α',α"-1,2,3-cyclopropanetriylidenetris[2,3,4,5,6-pentafluorobenzeneacetonitrile].

The hole-transport materials used in the hole-injection layers (111, 111a, and 111b) and the hole-transport layers (112, 112a, and 112b) are preferably substances with a hole mobility of higher than or equal to $10^{-6}$ cm$^2$/Vs. Note that other substances can be used as long as the substances have a hole-transport property higher than an electron-transport property.

Preferred hole-transport materials are π-electron rich heteroaromatic compounds (e.g., carbazole derivatives and indole derivatives) and aromatic amine compounds, specific examples of which include compounds having an aromatic amine skeleton, such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 3-[4-(9-phenanthryl)-phenyl]-9-phenyl-9H-carbazole (abbreviation: PCPPn), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 4,4',4"-tris(carbazol-9-yl)triphenylamine (abbreviation: TCTA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); compounds having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 3,3'-bis(9-phenyl-9H-carbazole) (abbreviation: PCCP), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA); compounds having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton, such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II).

Furthermore, a high molecular compound such as poly (N-vinylcarbazole) (abbreviation: PVK), poly(4-vinyltriphenylamine) (abbreviation: PVTPA), poly[N-(4-{N-[4-(4-diphenylamino)phenyl]phenyl-N-phenylamino}phenyl) methacrylamide] (abbreviation: PTPDMA), or poly[N,N'-bis(4-butylphenyl)-N,N'-bis(phenyl)benzidine] (abbreviation: Poly-TPD) can also be used.

Note that the hole-transport material is not limited to the above examples and one of or a combination of various known materials can be used as the hole-transport material for the hole-injection layers (111, 111a, and 111b) and the hole-transport layers (112, 112a, and 112b). Note that the hole-transport layers (112, 112a, and 112b) may each be formed of a plurality of layers. That is, a first hole-transport layer and a second hole-transport layer may be stacked.

In the light-emitting element illustrated in FIG. 1, the light-emitting layer (113 or 113a) is formed over the hole-transport layer (112 or 112a) of the EL layer (103 or 103a) by a vacuum evaporation method. Note that in the case of the light-emitting element with the tandem structure illustrated in FIG. 1(D), after the EL layer 103a and the charge-generation layer 104 are formed, the light-emitting layer 113b is also formed over the hole-transport layer 112b of the EL layer 103b by a vacuum evaporation method.

<Light-Emitting Layer>

The light-emitting layers (113, 113a, 113b, and 113c) each contain a light-emitting substance. Note that as the light-emitting substance, a substance that exhibits emission color of blue, purple, bluish purple, green, yellowish green, yellow, orange, red, or the like is appropriately used. When the light-emitting layers (113a, 113b, and 113c) are formed using different light-emitting substances, different emission colors can be exhibited (for example, complementary emission colors are combined to obtain white light emission). Furthermore, a stacked-layer structure in which one light-emitting layer contains different light-emitting substances may be employed.

The light-emitting layers (113, 113a, 113b, and 113c) may each contain one or more kinds of organic compounds (a host material and an assist material) in addition to a light-emitting substance (guest material). As the one or more kinds of organic compounds, one or both of the hole-transport material and the electron-transport material described in this embodiment can be used.

As the light-emitting substance that can be used in the light-emitting layers (113, 113a, 113b, and 113c), a light-emitting substance that converts singlet excitation energy into light emission in the visible light range or a light-emitting substance that converts triplet excitation energy into light emission in the visible light range can be used.

Examples of other light-emitting substances are given below.

As an example of the light-emitting substance that converts singlet excitation energy into light emission, a substance that emits fluorescence (fluorescent material) can be given; examples of the substance that emits fluorescence include a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of the pyrene derivative include N,N'-bis(3-methylphenyl)-N,N'-bis[3-(9-phenyl-9H-fluoren-9-yl)phenyl]pyrene-1,6-diamine (abbreviation: 1,6mMemFLPAPrn), (N,N'-diphenyl-N,N'-bis[4-(9-phenyl-9H-fluoren-9-yl)phenyl]pyrene-1,6-diamine) (abbreviation: 1,6FLPAPrn), N,N'-bis(dibenzofuran-2-yl)-N,N'-diphenylpyrene-1,6-diamine (abbreviation: 1,6FrAPrn), N,N'-bis(dibenzothiophen-2-yl)-N,N'-diphenylpyrene-1,6-diamine (abbreviation: 1,6ThAPrn), N,N'-(pyrene-1,6-diyl)bis[(N-phenylbenzo[b]naphtho[1,2-d]furan)-6-amine](abbreviation: 1,6BnfAPrn), N,N'-(pyrene-1,6-diyl)bis[(N-phenylbenzo[b]naphtho[1,2-d]furan)-8-amine] (abbreviation: 1,6BnfAPrn-02), and N,N'-(pyrene-1,6-diyl)bis[(6,N-diphenylbenzo[b]naphtho[1,2-d]furan)-8-amine] (abbreviation: 1,6BnfAPrn-03).

In addition, it is possible to use 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl)triphenylamine (abbreviation: PCBAPBA), perylene, 2,5,8,11-tetra(tert-butyl)perylene (abbreviation: TBP), N,N'''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), or the like.

As examples of the light-emitting substance that converts triplet excitation energy into light emission, a substance that emits phosphorescence (phosphorescent material) and a thermally activated delayed fluorescence (TADF) material that exhibits thermally activated delayed fluorescence can be given.

Examples of a phosphorescent material include an organometallic complex, a metal complex (platinum complex), and a rare earth metal complex. These substances exhibit different emission colors (emission peaks) and thus, any of them is selected and used appropriately according to need.

As a phosphorescent material that exhibits blue or green and whose emission spectrum has a peak wavelength at greater than or equal to 450 nm and less than or equal to 570 nm, the following substances can be given.

For example, organometallic complexes having a 4H-triazole skeleton, such as tris{2-[5-(2-methylphenyl)-4-(2,6-dimethylphenyl)-4H-1,2,4-triazol-3-yl-κ$N^2$]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: [Ir(iPr5btz)$_3$]); organometallic complexes having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); organometallic complexes having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); organometallic complexes in which a phenylpyridine derivative having an electron-withdrawing group is a ligand, such as bis[2-(4',6'-difluorophenyl)pyridinato-N,$C^{2'}$]iridium(III) tetrakis(1-pyrazolyl)borate (abbreviation: FIr6), bis[2-(4',6'-difluorophenyl)pyridinato-N,$C^{2'}$]iridium(III) picolinate (abbreviation: FIrpic), bis{2-[3',5'-bis(trifluoromethyl)phenyl]pyridinato-N,$C^{2'}$}iridium(III) picolinate (abbreviation: [Ir(CF$_3$ppy)$_2$(pic)]), and bis[2-(4',6'-difluorophenyl)pyridinato-N,$C^{2'}$]iridium(III) acetylacetonate (abbreviation: FIr(acac)); and the like can be given.

As a phosphorescent material that exhibits green or yellow and whose emission spectrum has a peak wavelength at greater than or equal to 495 nm and less than or equal to 590 nm, the following substances can be given.

For example, organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(t-

Buppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), (acetylacetonato) bis{4,6-dimethyl-2-[6-(2,6-dimethylphenyl)-4-pyrimidinyl-κN$^3$]phenyl-C}iridium(III) (abbreviation: [Ir(dmppm-dmp)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium (III) acetylacetonate (abbreviation: [Ir(ppy)$_2$acac]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), bis(2-phenylquinolinato-N,C$^{2'}$)iridium(III) acetylacetonate (abbreviation: [Ir(pq)$_2$(acac)]), [2-(4-phenyl-2-pyridinyl-κN)phenyl-κC]bis[2-(2-pyridinyl-κN)phenyl-κC]iridium(III) (abbreviation: [Ir(ppy)$_2$(4dppy)]), and bis[2-(2-pyridinyl-N)phenyl-κC][2-(4-methyl-5-phenyl-2-pyridinyl-κN)phenyl-κC]; organometallic complexes such as bis(2,4-diphenyl-1,3-oxazolato-N,C$^{2'}$)iridium(III) acetylacetonate (abbreviation: [Ir(dpo)$_2$(acac)]), bis{2-[4'-(perfluorophenyl)phenyl]pyridinato-N,C$^{2'}$}iridium(III) acetylacetonate (abbreviation: [Ir(p-PF-ph)$_2$(acac)]), and bis(2-phenylbenzothiazolato-N,C$^{2'}$)iridium(III) acetylacetonate (abbreviation: [Ir(bt)$_2$(acac)]); and rare earth metal complexes such as tris(acetylacetonato)(monophenanthroline)terbium(III) (abbreviation: [Tb(acac)$_3$(Phen)]) can be given.

As a phosphorescent material that exhibits yellow or red and whose emission spectrum has a peak wavelength at greater than or equal to 570 nm and less than or equal to 750 nm, the following substances can be given.

For example, organometallic complexes having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and (dipivaloylmethanato)bis[4,6-di(naphthalen-1-yl)pyrimidinato]iridium(III) (abbreviation: [Ir(dnpm)$_2$(dpm)]); organometallic complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinatoXdipivaloylmethanato)iridium(III) (abbreviation: [Ir(tppr)$_2$(dpm)]), bis{4,6-dimethyl-2-[3-(3,5-dimethylphenyl)-5-phenyl-2-pyrazinyl-κN]phenyl-κC}(2,6-dimethyl-3,5-heptanedionato-κ$^2$O,O')iridium(III) (abbreviation: [Ir(dmdppr-P)$_2$(dibm)]), bis {4,6-dimethyl-2-[5-(4-cyano-2,6-dimethylphenyl)-3-(3,5-dimethylphenyl)-2-pyrazinyl-κN]phenyl-κC}(2,2,6,6-tetramethyl-3,5-heptanedionato-κ$^2$O,O')iridium(III) (abbreviation: [Ir(dmdppr-dmCP)$_2$(dpm)]), (acetylacetonato)bis[2-methyl-3-phenylquinoxalinato-N, C$^{2'}$]iridium(III) (abbreviation: [Ir(mpq)$_2$(acac)]), (acetylacetonato)bis(2,3-diphenylquinoxalinato-N,C$^{2'}$)iridium(III) (abbreviation: [Ir(dpq)$_2$(acac)]), and (acetylacetonato)bis[2,3-bis(4-fluorophenyl)quinoxalinato]iridium(III) (abbreviation: [Ir(Fdpq)$_2$(acac)]); organometallic complexes having a pyridine skeleton, such as tris(1-phenylisoquinolinato-N, C$^{2'}$)iridium(III) (abbreviation: [Ir(piq)$_3$]), bis(1-phenylisoquinolinato-N,C$^{2'}$)iridium(III) acetylacetonate (abbreviation: [Ir(piq)$_2$acac]), and bis[4,6-dimethyl-2-(2-quinolinyl-κN)phenyl-κC](2,4-pentanedionato-κ$^2$O,O')iridium(III); platinum complexes such as 2,3,7,8,12,13,17,18-octaethyl-21H,23H-porphyrinplatinum(II) (abbreviation: [PtOEP]); and rare earth metal complexes such as tris(1,3-diphenyl-1,3-propanedionatoXmonophenanthroline)europium(II) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]) can be given.

As the organic compounds (the host material and the assist material) used in the light-emitting layers (113, 113$a$, 113$b$, and 113$c$), one or more kinds of substances having a larger energy gap than the light-emitting substance (the guest material) are selected to be used. In the case where a plurality of organic compounds are used in the light-emitting layers (113, 113$a$, 113$b$, and 113$c$), it is preferable to use a mixture of compounds that form an exciplex and a phosphorescent light-emitting substance. Such a structure makes it possible to obtain light emission utilizing ExTET (Exciplex-Triplet Energy Transfer), which is energy transfer from an exciplex to a light-emitting substance. In that case, although any of various organic compounds can be used in an appropriate combination, in order to form an exciplex efficiently, it is particularly preferable to combine a compound that easily accepts holes (hole-transport material) and a compound that easily accepts electrons (electron-transport material). The organic compound of one embodiment of the present invention has a low LUMO level and thus is suitable for the compound that easily accepts electrons.

In the case where the light-emitting substance is a fluorescent material, it is preferable to use, as the host material, an organic compound that has a high energy level in a singlet excited state and has a low energy level in a triplet excited state. For example, an anthracene derivative or a tetracene derivative is preferably used. Specifically, 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), 5,12-diphenyltetracene, and 5,12-bis(biphenyl-2-yl)tetracene, and the like can be given.

In the case where the light-emitting substance is a phosphorescent material, an organic compound having triplet excitation energy (energy difference between a ground state and a triplet excited state) which is higher than the triplet excitation energy of the light-emitting substance may be selected as the host material. In that case, it is possible to use a zinc- or aluminum-based metal complex, an oxadiazole derivative, a triazole derivative, a benzimidazole derivative, a quinoxaline derivative, a dibenzoquinoxaline derivative, a dibenzothiophene derivative, a dibenzofuran derivative, a pyrimidine derivative, a triazine derivative, a pyridine derivative, a bipyridine derivative, a phenanthroline derivative, an aromatic amine, a carbazole derivative, and the like.

More specifically, any of the following hole-transport materials and electron-transport materials can be used as the host material, for example.

Examples of these host materials having a high hole-transport property include aromatic amine compounds such as N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B).

Carbazole derivatives such as 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1) can be given as examples. As the carbazole derivative other than the above examples, 4,4'-di(N-carbazolyl)biphenyl (abbreviation: CBP), 1,3,5-tris[4-(N-carbazolyl)phenyl]benzene (abbreviation: TCPB), 1,4-bis[4-(N-carbazolyl)phenyl]-2,3,5,6-tetraphenylbenzene, or the like can also be used.

As the host material having a high hole-transport property, for example, it is possible to use aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4"-tris(carbazol-9-yl)triphenylamine (abbreviation: TCTA), 4,4',4"-tris[N-(1-naphthyl)-N-phenylamino]triphenylamine (abbreviation: 1-TNATA), 4,4',4"-tris(N,N'-diphenylamino)triphenylamine (abbreviation: TDATA), 4,4',4"-tris[N-(3-methylphenyl)-N-phenylamino]triphenylamine (abbreviation: m-MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N',N"-triphenyl-N,N',N"-tris(9-phenylcarbazol-3-yl)benzene-1,3,5-triamine (abbreviation: PCA3B), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 2-[N-(9-phenylcarbazol-3-yl)-N-phenylamino]spiro-9,9'-bifluorene (abbreviation: PCASF), 2,7-bis[N-(4-diphenylaminophenyl)-N-phenylamino]spiro-9,9'-bifluorene (abbreviation: DPA2SF), N-[4-(9H-carbazol-9-yl)phenyl]-N-(4-phenyl)phenylaniline (abbreviation: YGA1BP), and N,N'-bis[4-(carbazol-9-yl)phenyl]-N,N'-diphenyl-9,9-dimethylfluorene-2,7-diamine (abbreviation: YGA2F). Furthermore, carbazole compounds, thiophene compounds, furan compounds, fluorene compounds, triphenylene compounds, phenanthrene compounds, and the like such as 3-[4-(1-naphthyl)-phenyl]-9-phenyl-9H-carbazole (abbreviation: PCPN), 3-[4-(9-phenanthryl)-phenyl]-9-phenyl-9H-carbazole (abbreviation: PCPPn), 3,3'-bis(9-phenyl-9H-carbazole) (abbreviation: PCCP), 1,3-bis(N-carbazolyl)benzene (abbreviation: mCP), 3,6-bis(3,5-diphenylphenyl)-9-phenylcarbazole (abbreviation: CzTP), 4-{3-[3-(9-phenyl-9H-fluoren-9-yl)phenyl]phenyl}dibenzofuran (abbreviation: mmDBFFLBi-II), 4,4',4"-(benzene-1,3,5-triyl)tri(dibenzofuran) (abbreviation: DBF3P-II), 1,3,5-tri(dibenzothiophen-4-yl)benzene (abbreviation: DBT3P-II), 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), and 4-[3-(triphenylen-2-yl)phenyl]dibenzothiophene (abbreviation: mDBTPTp-II) can be used.

Examples of the host material having a high electron-transport property include a metal complex having a quinoline skeleton or a benzoquinoline skeleton, such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinoato)(4-phenylphenolato)aluminum(III) (abbreviation: BAlq), or bis(8-quinolinolato)zinc(II) (abbreviation: Znq). Alternatively, a metal complex having an oxazole-based or thiazole-based ligand, such as bis[2-(2-benzoxazolyl)phenolato]zinc(II) (abbreviation: ZnPBO) or bis[2-(2-benzothiazolyl)phenolato]zinc(II) (abbreviation: ZnBTZ), or the like can also be used. Other than metal complexes, any of the following can also be used: oxadiazole derivatives such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), and 9-[4-(5-phenyl-1,3,4-oxadiazol-2-yl)phenyl]-9H-carbazole (abbreviation: CO11); a triazole derivative such as 3-(4-biphenylyl)-4-phenyl-5-(4-tert-butylphenyl)-1,2,4-triazole (abbreviation: TAZ); a compound having an imidazole skeleton (in particular, a benzimidazole derivative) such as 2,2',2"-(1,3,5-benzenetriyl)tris(1-phenyl-1H-benzimidazole) (abbreviation: TPBI) or 2-[3-(dibenzothiophen-4-yl)phenyl]-1-phenyl-1H-benzimidazole (abbreviation: mDBTBIm-II); a compound having an oxazole skeleton (in particular, a benzoxazole derivative) such as 4,4'-bis(5-methylbenzoxazol-2-yl)stilbene (abbreviation: BzOS); a phenanthroline derivative such as bathophenanthroline (abbreviation: Bphen), bathocuproine (abbreviation: BCP), and 2,9-bis(naphthalen-2-yl)-4,7-diphenyl-1,10-phenanthroline (abbreviation: NBphen); heterocyclic compounds having a diazine skeleton such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)phenyl]pyrimidine (abbreviation: 4,6mCzP2Pm); a heterocyclic compound having a triazine skeleton such as 2-{4-[3-(N-phenyl-9H-carbazol-3-yl)-9H-carbazol-9-yl]phenyl}-4,6-diphenyl-1,3,5-triazine (abbreviation: PCCzPTzn); and heterocyclic compounds having a pyridine skeleton such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Furthermore, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can also be used.

Examples of the host material include condensed polycyclic aromatic compounds such as anthracene derivatives, phenanthrene derivatives, pyrene derivatives, chrysene derivatives, and dibenzo[g,p]chrysene derivatives; specifically, 9,10-diphenylanthracene (abbreviation: DPAnth), N,N-diphenyl-9-[4-(10-phenyl-9-anthryl)phenyl]-9H-carbazol-3-amine (abbreviation: CzA 1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), 6,12-dimethoxy-5,11-diphenylchrysene, N,N',N',N'',N''',N''',N''''-octaphenyldibenzo[g,p]chrysene-2,7,10,15-tetraamine (abbreviation: DBC 1), 9-[4-(10-phenyl-9-anthracenyl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 1,3,5-tri(1-pyrenyl)benzene (abbreviation: TPB3), and the like can be used.

In the case where a plurality of organic compounds are used in the light-emitting layers (113, 113a, 113b, and 113c), two kinds of compounds that form an exciplex (a first compound and a second compound) and an organometallic complex may be mixed and used. In that case, various organic compounds can be combined appropriately to be used; to form an exciplex efficiently, it is particularly preferable to combine a compound that easily accepts holes (hole-transport material) and a compound that easily accepts electrons (electron-transport material). Note that, as specific examples of the hole-transport material and the electron-transport material, the materials described in this embodiment can be used.

The TADF material refers to a material that can up-convert a triplet excited state into a singlet excited state (i.e., reverse intersystem crossing) using a little thermal energy and efficiently exhibits light emission (fluorescence) from the singlet excited state. As the condition under which the thermally activated delayed fluorescence is efficiently obtained, energy difference between the triplet excited level and the singlet excited level being greater than or equal to 0 eV and less than or equal to 0.2 eV, preferably greater than or equal to 0 eV and less than or equal to 0.1 eV can be given. Note that delayed fluorescence exhibited by the TADF material refers to light emission having a spectrum similar to that of normal fluorescence and an extremely long lifetime. The lifetime is $10^{-6}$ seconds or longer, preferably $10^{-3}$ seconds or longer.

Examples of the TADF material include fullerene, a derivative thereof, an acridine derivative such as proflavine, and eosin. In addition, a metal-containing porphyrin containing magnesium (Mg), zinc (Zn), cadmium (Cd), tin (Sn), platinum (Pt), indium (In), palladium (Pd), or the like can be given as examples. Examples of the metal-containing porphyrin include a protoporphyrin-tin fluoride complex (abbreviation: $SnF_2$(Proto IX)), a mesoporphyrin-tin fluoride complex (abbreviation: $SnF_2$(Meso IX)), a hematoporphyrin-tin fluoride complex (abbreviation: $SnF_2$(Hemato IX)), a coproporphyrin tetramethyl ester-tin fluoride complex (abbreviation: $SnF_2$(Copro III-4Me)), an octaethylporphyrin-tin fluoride complex (abbreviation: $SnF_2$(OEP)), an etioporphyrin-tin fluoride complex (abbreviation: $SnF_2$(Etio I)), and an octaethylporphyrin-platinum chloride complex (abbreviation: $PtCl_2$OEP).

Other than these, a heterocyclic compound having a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(1 OH-phenoxazin-1-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. Note that a substance in which the n-electron rich heteroaromatic ring is directly bonded to the n-electron deficient heteroaromatic ring is particularly preferable because both the donor property of the n-electron rich heteroaromatic ring and the acceptor property of the n-electron deficient heteroaromatic ring are increased and the energy difference between the singlet excited state and the triplet excited state becomes small.

Note that in the case where a TADF material is used, the TADF material can also be used in combination with another organic compound.

In the light-emitting element illustrated in FIG. 1, an electron-transport layer (114 or 114a) is formed over the light-emitting layer (113 or 113a) of the EL layer (103 or 103a) by a vacuum evaporation method. Note that in the case of the light-emitting element with the tandem structure illustrated in FIG. 1(D), after the EL layer 103a and the charge-generation layer 104 are formed, an electron-transport layer 114b is also formed over the light-emitting layer 113b of the EL layer 103b by a vacuum evaporation method.

<Electron-Transport Layer>

The electron-transport layers (114, 114a, and 114b) are each a layer that transports the electrons, which are injected from the second electrode 102 by the electron-injection layers (115, 115a, and 115b), to the light-emitting layers (113, 113a, and 113b). Note that the electron-transport layers (114, 114a, and 114b) are each a layer containing an electron-transport material. It is preferable that the electron-transport materials used in the electron-transport layers (114, 114a, and 114b) be substances with an electron mobility of higher than or equal to $1 \times 10^{-6}$ $cm^2$/Vs. Note that other substances can be used as long as the substances have an electron-transport property higher than a hole-transport property.

Examples of the electron-transport material include a metal complex having a quinoline ligand, a benzoquinoline ligand, an oxazole ligand, or a thiazole ligand; an oxadiazole derivative; a triazole derivative; a phenanthroline derivative; a pyridine derivative; and a bipyridine derivative. In addition, a π-electron deficient heteroaromatic compound such as a nitrogen-containing heteroaromatic compound can also be used.

Specifically, it is possible to use metal complexes such as $Alq_3$, tris(4-methyl-8-quinolinolato)aluminum (abbreviation: $Almq_3$), bis(10-hydroxybenzo[h]quinolinato)beryllium (abbreviation: $BeBq_2$), BAlq, bis[2-(2-hydroxyphenyl)benzoxazolato]zinc(II) (abbreviation: $Zn(BOX)_2$), and bis[2-(2-hydroxyphenyl)benzothiazolato]zinc (abbreviation: $Zn(BTZ)_2$), heteroaromatic compounds such as 2-(4-biphenylyl)-5-(4-tert-butylphenyl)-1,3,4-oxadiazole (abbreviation: PBD), OXD-7, 3-(4'-tert-butylphenyl)-4-phenyl-5-(4''-biphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), and 4,4'-bis(5-methylbenzoxazol-2-yl)stilbene (abbreviation: BzOS), and quinoxaline or dibenzoquinoxaline derivatives such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

Furthermore, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can also be used.

Each of the electron-transport layers (114, 114a, and 114b) is not limited to a single layer, and may be a stack of two or more layers each made of any of the above substances.

In the light-emitting element illustrated in FIG. 1, the electron-injection layer (115 or 115a) is formed over the electron-transport layer (114 or 114a) of the EL layer (103 or 103a) by a vacuum evaporation method. Note that in the case of the light-emitting element with the tandem structure illustrated in FIG. 1(D), after the EL layer 103a and the charge-generation layer 104 are formed, the electron-injection layer 115b is also formed over the electron-transport layer 114b of the EL layer 103b by a vacuum evaporation method.

<Electron-Injection Layer>

The electron-injection layers (115, 115a, and 115b) are each a layer containing a substance having a high electron-injection property. The electron-injection layers (115, 115a, and 115b) can each be formed using an alkali metal, an alkaline earth metal, or a compound thereof, such as lithium fluoride (LiF), cesium fluoride (CsF), calcium fluoride ($CaF_2$), or lithium oxide (LiOx). A rare earth metal compound such as erbium fluoride ($ErF_3$) can be used. Electride may also be used for the electron-injection layers (115, 115a, and 115b). Examples of the electride include a substance in which electrons are added at high concentration to a mixed oxide of calcium and aluminum. Note that any of the substances used in the electron-transport layers (114, 114a, and 114b), which are given above, can also be used.

A composite material in which an organic compound and an electron donor (donor) are mixed may also be used in the electron-injection layers (115, 115a, and 115b). Such a composite material is excellent in an electron-injection property and an electron-transport property because electrons are generated in the organic compound by the electron donor. In this case, the organic compound is preferably a material excellent in transporting the generated electrons; specifically, for example, the above-mentioned electron-transport materials (metal complexes, heteroaromatic compounds, and the like) used in the electron-transport layers (114, 114a, and 114b) can be used. Any substance showing an electron-donating property with respect to the organic compound can serve as an electron donor. Specifically, an alkali metal, an alkaline earth metal, and a rare earth metal are preferable, and lithium, cesium, magnesium, calcium, erbium, ytterbium, and the like are given as examples. In addition, an alkali metal oxide and an alkaline earth metal oxide are preferable, and lithium oxide, calcium oxide, barium oxide, and the like are given as examples. A Lewis base such as magnesium oxide can also be used. An organic compound such as tetrathiafulvalene (abbreviation: TTF) can also be used.

Note that in the case where light obtained from the light-emitting layer 113b is amplified, for example, formation is preferably performed such that the optical path length between the second electrode 102 and the light-emitting layer 113b is less than one fourth of the wavelength X of light emitted from the light-emitting layer 113b. In that case, the optical path length can be adjusted by changing the thickness of the electron-transport layer 114b or the electron-injection layer 115b.

<Charge-Generation Layer>

The charge-generation layer 104 has a function of injecting electrons into the EL layer 103a and injecting holes into the EL layer 103b when voltage is applied between the first electrode (anode) 101 and the second electrode (cathode) 102. Note that the charge-generation layer 104 may have either a structure in which an electron acceptor (acceptor) is added to a hole-transport material or a structure in which an electron donor (donor) is added to an electron-transport material. Alternatively, both of these structures may be stacked. Note that forming the charge-generation layer 104 with the use of any of the above materials can suppress an increase in drive voltage in the case where the EL layers are stacked.

In the case where the charge-generation layer 104 has a structure in which an electron acceptor is added to a hole-transport material, any of the materials described in this embodiment can be used as the hole-transport material. As the electron acceptor, 7,7,8,8-tetracyano-2,3,5,6-tetrafluoroquinodimethane (abbreviation: F4TCNQ), chloranil, and the like can be given. In addition, oxides of metals that belong to Group 4 to Group 8 of the periodic table can be given as examples. Specifically, vanadium oxide, niobium oxide, tantalum oxide, chromium oxide, molybdenum oxide, tungsten oxide, manganese oxide, rhenium oxide, and the like can be given as examples.

In the case where the charge-generation layer 104 has a structure in which an electron donor is added to an electron-transport material, any of the materials described in this embodiment can be used as the electron-transport material. As the electron donor, it is possible to use an alkali metal, an alkaline earth metal, a rare earth metal, metals that belong to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that the EL layer 103c in FIG. 1(E) has a structure similar to those of the above-described EL layers (103, 103a, and 103b). In addition, the charge-generation layers 104a and 104b each have a structure similar to that of the above-described charge-generation layer 104.

<Substrate>

The light-emitting element described in this embodiment can be formed over any of a variety of substrates. Note that the type of the substrate is not limited to a certain type. Examples of the substrate include semiconductor substrates (e.g., a single crystal substrate and a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, a laminate film, paper including a fibrous material, and a base material film.

Note that examples of the glass substrate include barium borosilicate glass, aluminoborosilicate glass, and soda lime glass. Examples of the flexible substrate, the laminate film, and the base material film include plastics typified by polyethylene terephthalate (PET), polyethylene naphthalate (PEN), and polyether sulfone (PES); a synthetic resin such as an acrylic resin; polypropylene; polyester; polyvinyl fluoride; polyvinyl chloride; polyamide; polyimide; aramid; epoxy; an inorganic vapor deposition film; and paper.

Note that for fabrication of the light-emitting element described in this embodiment, a vacuum process such as an evaporation method or a solution process such as a spin coating method or an ink-jet method can be used. In the case where an evaporation method is used, a physical vapor deposition method (PVD method) such as a sputtering method, an ion plating method, an ion beam evaporation method, a molecular beam evaporation method, or a vacuum evaporation method; a chemical vapor deposition method (CVD method); or the like can be used. Specifically, the functional layers (the hole-injection layers (111, 111a, and 111b), the hole-transport layers (112, 112a, and 112b), the light-emitting layers (113, 113a, 113b, and 113c), the electron-transport layers (114, 114a, and 114b), the electron-injection layers (115, 115a, and 115b) included in the EL layers and the charge-generation layers (104, 104a, and 104b)) of the light-emitting element can be formed by an evaporation method (e.g., a vacuum evaporation method), a coating method (e.g., a dip coating method, a die coating method, a bar coating method, a spin coating method, or a spray coating method), a printing method (e.g., an ink-jet method, screen printing (stencil), offset printing (planography), flexography (relief printing), gravure printing, or micro-contact printing), or the like.

Note that materials that can be used for the functional layers (the hole-injection layers (111, 111a, and 111b), the hole-transport layers (112, 112a, and 112b), the light-emitting layers (113, 113a, 113b, and 113c), the electron-transport layers (114, 114a, and 114b), and the electron-injection layers (115, 115a, and 115b)) that are included in the EL layers (103, 103a, and 103b) and the charge-generation layers (104, 104a, and 104b)) of the light-emitting element described in this embodiment are not limited to the above materials, and other materials can also be used in combination as long as the functions of the layers are fulfilled. For example, a high molecular compound (e.g., an oligomer, a dendrimer, and a polymer), a middle molecular compound (a compound between a low molecular compound and a high molecular compound with a molecular weight of 400 to 4000), or an inorganic compound (e.g., a quantum dot material) can be used. Note that as the quantum dot material, a colloidal quantum dot material, an alloyed quantum dot material, a core-shell quantum dot material, a core quantum dot material, or the like can be used.

The structure described in this embodiment can be used in an appropriate combination with any of the structures described in the other embodiments.

Embodiment 3

Figure 2A:
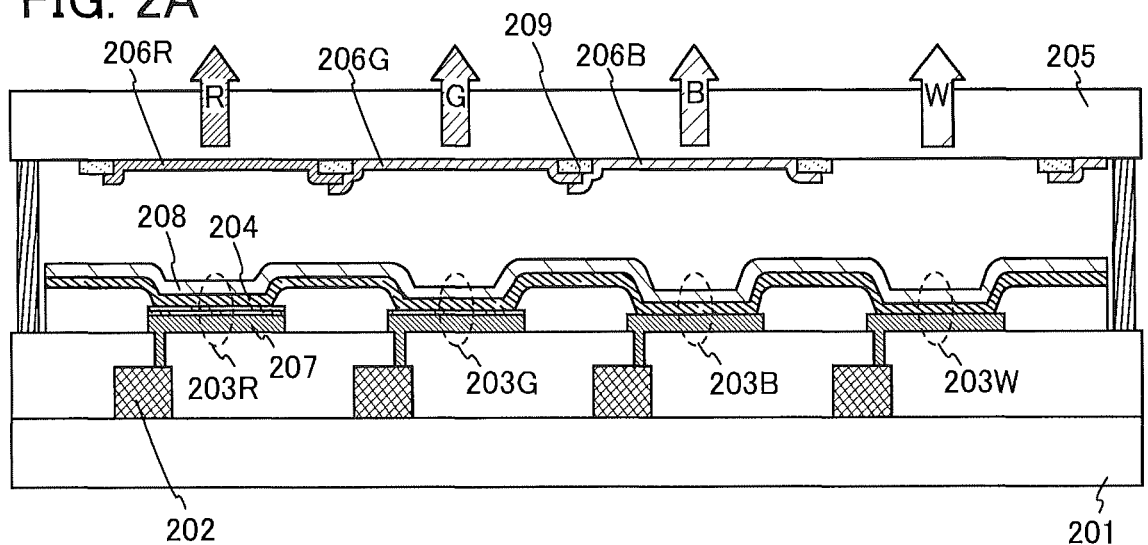
FIGS. 2A-2C are drawings illustrating light-emitting devices.

In this embodiment, a light-emitting device of one embodiment of the present invention will be described. Note that a light-emitting device illustrated in FIG. 2(A) is an active-matrix light-emitting device in which transistors (FETs) 202 over a first substrate 201 are electrically connected to light-emitting elements (203R, 203G, 203B, and 203W); the light-emitting elements (203R, 203G, 203B, and 203W) include a common EL layer 204 and each have a microcavity structure in which the optical path length between electrodes of each light-emitting element is adjusted according to the emission color of the light-emitting element. In addition, the light-emitting device is a top-emission light-emitting device in which light is emitted from the EL layer 204 through color filters (206R, 206G, and 206B) formed on a second substrate 205.

In the light-emitting device illustrated in FIG. 2(A), the first electrode 207 is formed so as to function as a reflective electrode. The second electrode 208 is formed so as to function as a semi-transmissive and semi-reflective electrode. Note that description in any of the other embodiments can be referred to for electrode materials forming the first electrode 207 and the second electrode 208 and appropriate materials can be used.

Figure 2B:
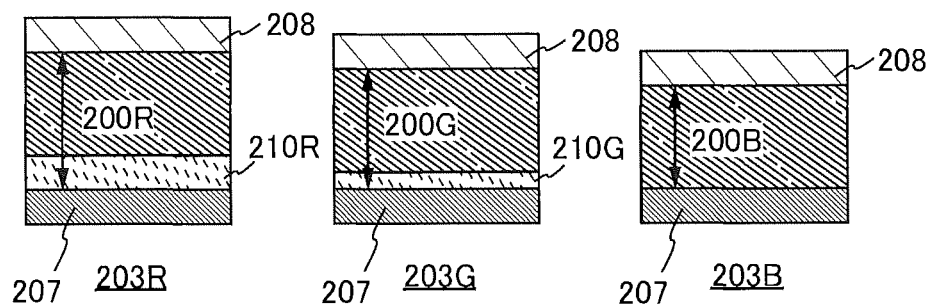

In the case where the light-emitting element 203R is a red-light-emitting element, the light-emitting element 203G is a green-light-emitting element, the light-emitting element 203B is a blue-light-emitting element, and the light-emitting element 203W is a white-light-emitting element in FIG. 2(A), for example, a gap between the first electrode 207 and the second electrode 208 in the light-emitting element 203R is adjusted to have an optical path length 200R, a gap between the first electrode 207 and the second electrode 208 in the light-emitting element 203G is adjusted to have an optical path length 200G, and a gap between the first electrode 207 and the second electrode 208 in the light-emitting element 203B is adjusted to have an optical path length 200B as illustrated in FIG. 2(B). Note that optical adjustment can be performed in such a manner that a conductive layer 210R is stacked over the first electrode 207 in the light-emitting element 203R and a conductive layer 210G is stacked over the first electrode 207 in the light-emitting element 203G as illustrated in FIG. 2(B).

The color filters (206R, 206G, and 206B) are formed on the second substrate 205. Note that the color filters each transmit visible light in a specific wavelength range and blocks visible light in a specific wavelength range. Thus, as illustrated in FIG. 2(A), the color filter 206R that transmits only light in the red wavelength range is provided in a position overlapping with the light-emitting element 203R, whereby red light emission can be obtained from the light-emitting element 203R. The color filter 206G that transmits only light in the green wavelength range is provided in a position overlapping with the light-emitting element 203G, whereby green light emission can be obtained from the light-emitting element 203G. The color filter 206B that transmits only light in the blue wavelength range is provided in a position overlapping with the light-emitting element 203B, whereby blue light emission can be obtained from the light-emitting element 203B. Note that the light-emitting element 203W can emit white light without a color filter. Note that a black layer (black matrix) 209 may be provided at an end portion of one type of color filter. The color filters (206R, 206G, and 206B) and the black layer 209 may be covered with an overcoat layer using a transparent material.

Figure 2C:
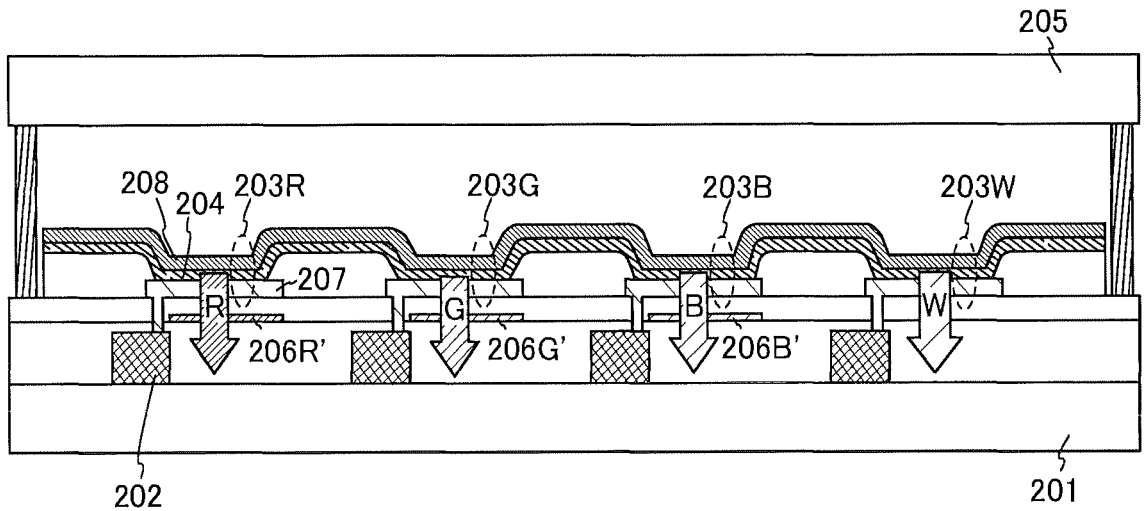

Although the light-emitting device illustrated in FIG. 2(A) has a structure in which light is extracted from the second substrate 205 side (top emission structure), the light-emitting device may have a structure in which light is extracted from the first substrate 201 side where the FETs 202 are formed (bottom emission structure) as illustrated in FIG. 2(C). For a bottom-emission light-emitting device, the first electrode 207 is formed so as to function as a semi-transmissive and semi-reflective electrode and the second electrode 208 is formed so as to function as a reflective electrode. As the first substrate 201, a substrate having at least a light-transmitting property is used. As illustrated in FIG. 2(C), color filters (206R', 206G', and 206B') are provided closer to the first substrate 201 than the light-emitting elements (203R, 203G, and 203B) are.

FIG. 2(A) illustrates the case where the light-emitting elements are the red-light-emitting element, the green-light-emitting element, the blue-light-emitting element, and the white-light-emitting element; however, the light-emitting elements of embodiments of the present invention are not limited to the above structures, and a yellow-light-emitting element or an orange-light-emitting element may be included. Note that description in any of the other embodiments can be referred to for materials that are used for the EL layers (a light-emitting layer, a hole-injection layer, a hole-transport layer, an electron-transport layer, an electron-injection layer, a charge-generation layer, and the like) to fabricate each of the light-emitting elements and appropriate materials can be used. In that case, a color filter needs to be appropriately selected according to the emission color of the light-emitting element.

With the above structure, a light-emitting device including light-emitting elements that exhibit a plurality of emission colors can be obtained.

Note that the structures described in this embodiment can be used in an appropriate combination with any of the structures described in the other embodiments.

Embodiment 4

In this embodiment, a light-emitting device of one embodiment of the present invention will be described.

The use of the element structure of the light-emitting element of one embodiment of the present invention allows fabrication of an active-matrix light-emitting device or a passive-matrix light-emitting device. Note that an active-matrix light-emitting device has a structure including a combination of a light-emitting element and a transistor (FET). Thus, each of a passive-matrix light-emitting device and an active-matrix light-emitting device is included in one embodiment of the present invention. Note that any of the light-emitting elements described in the other embodiments can be used in the light-emitting device described in this embodiment.

In this embodiment, an active-matrix light-emitting device will be described with reference to FIG. 3.

Figure 3A:
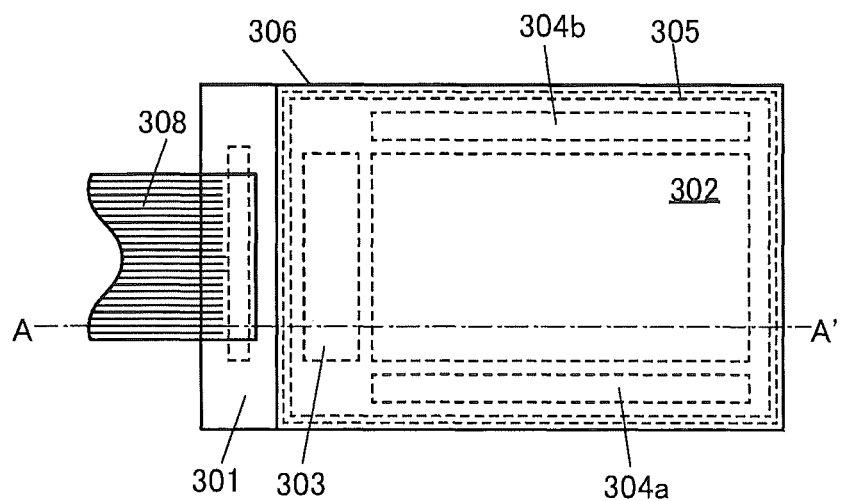
FIGS. 3A-3B are drawings illustrating a light-emitting device.
Figure 3B:
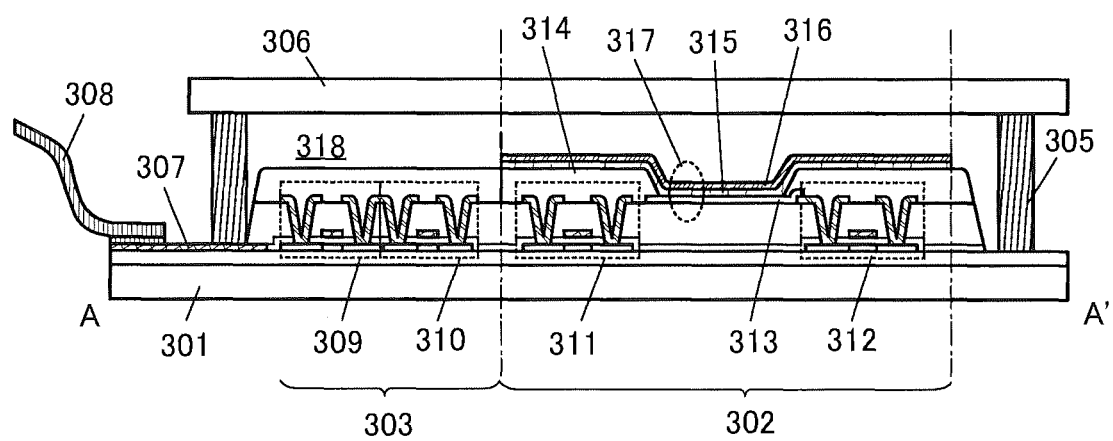

FIG. 3(A) is a top view illustrating a light-emitting device 21, and FIG. 3(B) is a cross-sectional view taken along a chain line A-A' in FIG. 3(A). The active-matrix light-emitting device includes a pixel portion 302, a driver circuit portion (source line driver circuit) 303, and driver circuit portions (gate line driver circuits) (304a and 304b) that are provided over a first substrate 301. The pixel portion 302 and the driver circuit portions (303, 304a, and 304b) are sealed between the first substrate 301 and a second substrate 306 with a sealant 305.

A lead wiring 307 is provided over the first substrate 301. The lead wiring 307 is electrically connected to an FPC 308 which is an external input terminal. Note that the FPC 308 transmits a signal (e.g., a video signal, a clock signal, a start signal, or a reset signal) or a potential from the outside to the driver circuit portions (303, 304a, and 304b). The FPC 308 may be provided with a printed wiring board (PWB). Note that the light-emitting device provided with an FPC or a PWB is included in the category of a light-emitting device.

Next, FIG. 3(B) illustrates the cross-sectional structure.

The pixel portion 302 is made up of a plurality of pixels each of which includes an FET (switching FET) 311, an FET (current control FET) 312, and a first electrode 313 electrically connected to the FET 312. Note that the number of FETs included in each pixel is not particularly limited and can be set appropriately as needed.

As FETs 309, 310, 311, and 312, for example, a staggered transistor or an inverted staggered transistor can be used without particular limitation. A top-gate transistor, a bottom-gate transistor, or the like may be used.

Note that there is no particular limitation on the crystallinity of a semiconductor that can be used for the FETs 309, 310, 311, and 312, and an amorphous semiconductor or a semiconductor having crystallinity (a microcrystalline semiconductor, a polycrystalline semiconductor, a single crystal semiconductor, or a semiconductor partly including crystal regions) may be used. The use of a semiconductor having crystallinity can suppress deterioration of the transistor characteristics, which is preferable.

For these semiconductors, a Group 14 element, a compound semiconductor, an oxide semiconductor, an organic semiconductor, or the like can be used, for example. Typically, a semiconductor containing silicon, a semiconductor containing gallium arsenide, an oxide semiconductor containing indium, or the like can be used.

The driver circuit portion 303 includes the FET 309 and the FET 310. The driver circuit portion 303 may be formed with a circuit including transistors having the same conductivity type (either n-channel transistors or p-channel transistors) or a CMOS circuit including an n-channel transistor and a p-channel transistor. Furthermore, a structure including a driver circuit outside may be employed.

An end portion of the first electrode 313 is covered with an insulator 314. For the insulator 314, an organic compound such as a negative photosensitive resin or a positive photosensitive resin (acrylic resin), or an inorganic compound such as silicon oxide, silicon oxynitride, or silicon nitride can be used. An upper end portion or a lower end portion of the insulator 314 preferably has a curved surface with curvature. In that case, favorable coverage with a film formed over the insulator 314 can be obtained.

An EL layer 315 and a second electrode 316 are stacked over the first electrode 313. The EL layer 315 includes a light-emitting layer, a hole-injection layer, a hole-transport layer, an electron-transport layer, an electron-injection layer, a charge-generation layer, and the like.

The structure and materials described in any of the other embodiments can be used for the structure of a light-emitting element 317 described in this embodiment. Although not illustrated here, the second electrode 316 is electrically connected to the FPC 308 which is an external input terminal.

Although the cross-sectional view in FIG. 3(B) illustrates only one light-emitting element 317, a plurality of light-emitting elements are arranged in a matrix in the pixel portion 302. Light-emitting elements from which light of three kinds of colors (R, G, and B) are obtained are selectively formed in the pixel portion 302, whereby a light-emitting device capable of full-color display can be formed. In addition to the light-emitting elements from which light of three kinds of colors (R, G, and B) are obtained, for example, light-emitting elements from which light of white (W), yellow (Y), magenta (M), cyan (C), and the like are obtained may be formed. For example, the light-emitting elements from which light of some of the above colors are obtained are added to the light-emitting elements from which light of three kinds of colors (R, G, and B) are obtained, whereby effects such as an improvement in color purity and a reduction in power consumption can be obtained. Alternatively, a light-emitting device that is capable of full-color display may be fabricated by a combination with color filters. As the kinds of color filters, red (R), green (G), blue (B), cyan (C), magenta (M), and yellow (Y) color filters and the like can be used.

When the second substrate 306 and the first substrate 301 are bonded to each other with the sealant 305, the FETs (309, 310, 311, and 312) and the light-emitting element 317 over the first substrate 301 are provided in a space 318 surrounded by the first substrate 301, the second substrate 306, and the sealant 305. Note that the space 318 may be filled with an inert gas (e.g., nitrogen or argon) or an organic substance (including the sealant 305).

An epoxy-based resin or glass frit can be used for the sealant 305. It is preferable to use a material that is permeable to as little moisture and oxygen as possible for the sealant 305. As the second substrate 306, a material that can be used as the first substrate 301 can be similarly used. Thus, any of the various substrates described in the other embodiments can be appropriately used. As the substrate, a glass substrate, a quartz substrate, or a plastic substrate made of FRP (Fiber-Reinforced Plastics), PVF (polyvinyl fluoride), polyester, an acrylic resin, or the like can be used. In the case where glass frit is used for the sealant, the first substrate 301 and the second substrate 306 are preferably glass substrates in terms of adhesion.

In the above manner, the active-matrix light-emitting device can be obtained.

In the case where the active-matrix light-emitting device is formed over a flexible substrate, the FETs and the light-emitting element may be directly formed over the flexible substrate; alternatively, the FETs and the light-emitting element may be formed over a substrate provided with a separation layer and then separated at the separation layer by application of heat, force, laser irradiation, or the like to be transferred to a flexible substrate. For the separation layer, a stack including inorganic films such as a tungsten film and a silicon oxide film, or an organic resin film of polyimide or the like can be used, for example. Examples of the flexible substrate include, in addition to a substrate over which a transistor can be formed, a paper substrate, a cellophane substrate, an aramid film substrate, a polyimide film substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, and a rubber substrate. With the use of any of these substrates, high durability, high heat resistance, a reduction in weight, and a reduction in thickness can be achieved.

Note that the structures described in this embodiment can be used in an appropriate combination with any of the structures described in the other embodiments.

Embodiment 5

In this embodiment, examples of a variety of electronic devices and an automobile completed using the light-emitting device of one embodiment of the present invention or a display device including the light-emitting element of one embodiment of the present invention are described.

Electronic devices illustrated in FIG. 4(A) to FIG. 4(F) can include a housing 7000, a display portion 7001, a speaker 7003, an LED lamp 7004, operation keys 7005 (including a power switch or an operation switch), a connection terminal 7006, a sensor 7007 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 7008, and the like.

FIG. 4(A) is a mobile computer which can include a switch 7009, an infrared port 7010, and the like in addition to the above components.

FIG. 4(B) is a portable image reproducing device (e.g., a DVD player) which is provided with a recording medium and can include a second display portion 7002, a recording medium reading portion 7011, and the like in addition to the above components.

FIG. 4(C) is a goggle-type display which can include the second display portion 7002, a support portion 7012, an earphone 7013, and the like in addition to the above components.

FIG. 4(D) is a digital camera with a television reception function, which can include an antenna 7014, a shutter button 7015, an image receiving portion 7016, and the like in addition to the above components.

FIG. 4(E) is a cellular phone (including a smartphone) which can include the display portion 7001, a microphone 7019, the speaker 7003, a camera 7020, an external connection portion 7021, an operation button 7022, and the like in the housing 7000.

FIG. 4(F) is a large-size television set (also referred to as TV or a television receiver), which can include the housing 7000, the display portion 7001, and the like. In addition, shown here is a structure where the housing 7000 is supported by a stand 7018. The television set can be operated with a separate remote controller 7111 or the like. Note that the display portion 7001 may include a touch sensor, in which case the television set may be operated by touch on the display portion 7001 with a finger or the like. The remote controller 7111 may be provided with a display portion for displaying data output from the remote controller 7111. With operation keys or a touch panel provided in the remote controller 7111, channels and volume can be operated and images displayed on the display portion 7001 can be operated.

The electronic devices illustrated in FIG. 4(A) to FIG. 4(F) can have a variety of functions. For example, they can have a function of displaying a variety of data (e.g., a still image, a moving image, and a text image) on the display portion, a touch panel function, a function of displaying a calendar, date, time, or the like, a function of controlling processing with a variety of software (programs), a wireless communication function, a function of being connected to a variety of computer networks with a wireless communication function, a function of transmitting and receiving a variety of data with a wireless communication function, and a function of reading out a program or data stored in a recording medium and displaying it on the display portion. Furthermore, the electronic device including a plurality of display portions can have a function of displaying image data mainly on one display portion while displaying text data mainly on the other display portion, a function of displaying a three-dimensional image by displaying images on a plurality of display portions with a parallax taken into account, or the like. Furthermore, the electronic device including an image receiving portion can have a function of taking a still image, a function of taking a moving image, a function of automatically or manually correcting a taken image, a function of storing a taken image in a recording medium (an external recording medium or a recording medium incorporated in the camera), a function of displaying a taken image on the display portion, or the like. Note that functions that the electronic devices illustrated in FIG. 4(A) to FIG. 4(F) can have are not limited to those described above, and the electronic devices can have a variety of functions.

FIG. 4(G) is a smart watch, which includes the housing 7000, the display portion 7001, operation buttons 7022 and 7023, a connection terminal 7024, a band 7025, a clasp 7026, and the like.

The display portion 7001 mounted in the housing 7000 also serving as a bezel includes a non-rectangular display region. The display portion 7001 can display an icon 7027 indicating time, another icon 7028, and the like. The display portion 7001 may be a touch panel (input/output device) including a touch sensor (input device).

Note that the smart watch illustrated in FIG. 4(G) can have a variety of functions. For example, the smart watch can have a function of displaying a variety of data (e.g., a still image, a moving image, and a text image) on the display portion, a touch panel function, a function of displaying a calendar, date, time, or the like, a function of controlling processing with a variety of software (programs), a wireless communication function, a function of being connected to a variety of computer networks with a wireless communication function, a function of transmitting and receiving a variety of data with a wireless communication function, and a function of reading out a program or data stored in a recording medium and displaying it on the display portion.

Moreover, a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like can be included inside the housing 7000.

Note that the light-emitting device of one embodiment of the present invention and the display device including the light-emitting element of one embodiment of the present invention can be used in the display portions of the electronic devices described in this embodiment, enabling the electronic devices to have a long lifetime.

Figure 5A:
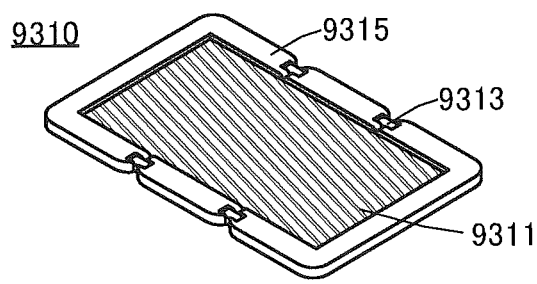
FIGS. 5A-5C are drawings illustrating an electronic device.
Figure 5B:
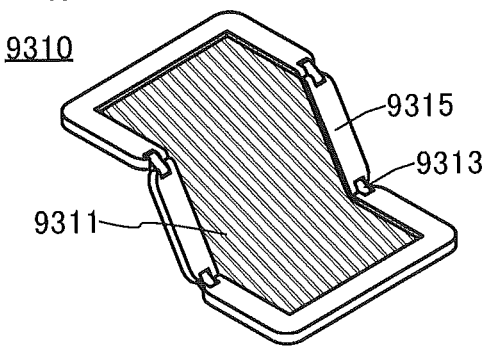
Figure 5C:
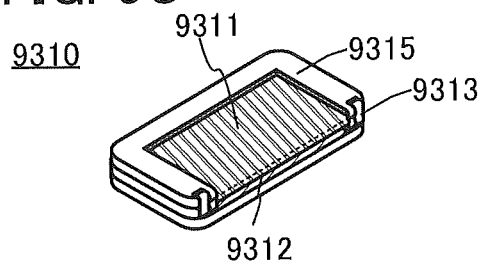

Another electronic device including the light-emitting device is a foldable portable information terminal illustrated in FIG. 5(A) to FIG. 5(C). FIG. 5(A) illustrates a portable information terminal 9310 which is opened. FIG. 5(B) illustrates the portable information terminal 9310 in a state in the middle of change from one of an opened state and a folded state to the other. FIG. 5(C) illustrates the portable information terminal 9310 which is folded. The portable information terminal 9310 is highly portable when folded, and is highly browsable when opened because of the seamless large display region.

A display portion 9311 is supported by three housings 9315 joined together by hinges 9313. Note that the display portion 9311 may be a touch panel (input/output device) including a touch sensor (input device). By bending the display portion 9311 at a portion between two housings 9315 with the use of the hinges 9313, the portable information terminal 9310 can be reversibly changed in shape from an opened state to a folded state. The light-emitting device of one embodiment of the present invention can be used for the display portion 9311. In addition, an electronic device having a long lifetime can be provided. A display region 9312 in the display portion 9311 is a display region that is positioned at a side surface of the portable information terminal 9310 which is folded. On the display region 9312, information icons, file shortcuts of frequently used applications or programs, and the like can be displayed, and confirmation of information and the starting of application and the like can be smoothly performed.

Figure 6A:
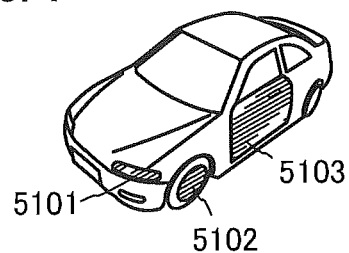
FIGS. 6A-6B are drawings illustrating an automobile.
Figure 6B:
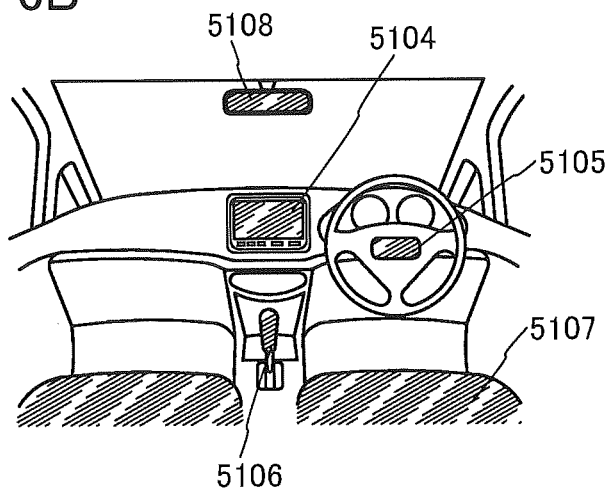

FIGS. 6(A) and 6(B) illustrate an automobile including the light-emitting device. In other words, the light-emitting device can be integrated into an automobile. Specifically, the light-emitting device can be applied to lights 5101 (including lights of the rear part of the car), a wheel 5102, a part or the whole of a door 5103, or the like on the outer side of the automobile which is illustrated in FIG. 6(A). The light-emitting device can also be applied to a display portion 5104, a steering wheel 5105, a shifter 5106, a seat 5107, an inner rearview mirror 5108, or the like on the inner side of the automobile which is illustrated in FIG. 6(B). Apart from that, the light-emitting device may be used for a part of the glass window.

In the above manner, the electronic devices and automobiles in which the light-emitting device or the display device of one embodiment of the present invention is used can be obtained. In that case, a long-lifetime electronic device can be obtained. Note that the light-emitting device or the display device can be used for electronic devices and automobiles in a variety of fields without being limited to those described in this embodiment.

Note that the structures described in this embodiment can be used in an appropriate combination with any of the structures described in the other embodiments.

Embodiment 6

In this embodiment, the structure of a lighting device fabricated using the light-emitting device of one embodiment of the present invention or the light-emitting element which is part of the light-emitting device will be described with reference to FIG. 7.

Figure 7A:
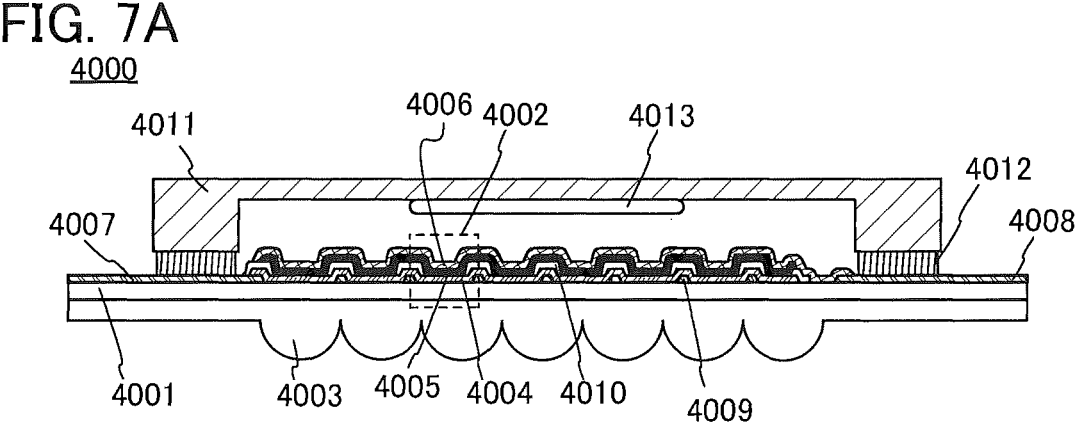
FIGS. 7A-7B are drawings illustrating lighting devices.
Figure 7B:
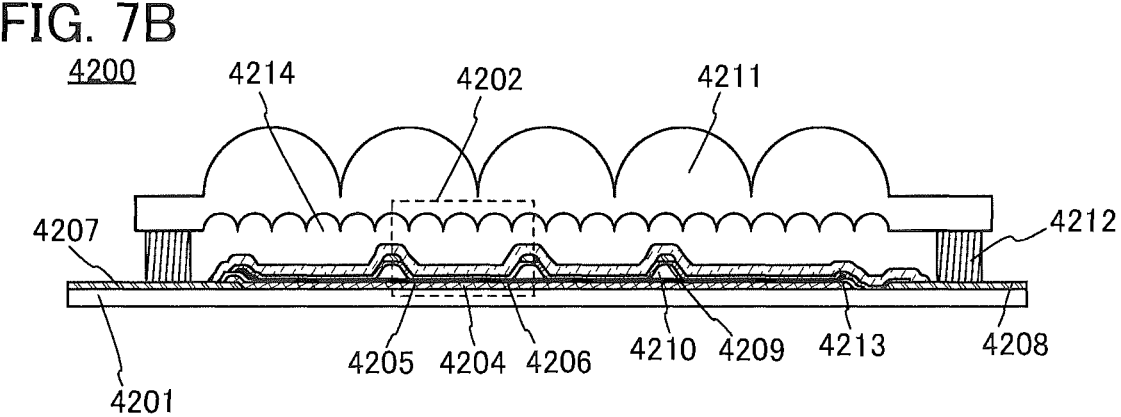

FIGS. 7(A) and 7(B) shows examples of cross-sectional views of lighting devices, FIG. 7(A) is a bottom-emission lighting device in which light is extracted from the substrate side, and FIG. 7(B) is a top-emission lighting device in which light is extracted from the sealing substrate side.

A lighting device 4000 illustrated in FIG. 7(A) includes a light-emitting element 4002 over a substrate 4001. In addition, the lighting device 4000 includes a substrate 4003 with unevenness on the outside of the substrate 4001. The light-emitting element 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other with a sealant 4012. A desiccant 4013 is preferably provided between the sealing substrate 4011 and the light-emitting element 4002. The substrate 4003 has the unevenness illustrated in FIG. 7(A), whereby the extraction efficiency of light generated in the light-emitting element 4002 can be increased.

A lighting device 4200 illustrated in FIG. 7(B) includes a light-emitting element 4202 over a substrate 4201. The light-emitting element 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may also be provided. In addition, an insulating layer 4210 may be provided under the auxiliary wiring 4209.

The substrate 4201 and a sealing substrate 4211 with unevenness are bonded to each other with a sealant 4212. A barrier film 4213 and a planarization film 4214 may be provided between the sealing substrate 4211 and the light-emitting element 4202. The sealing substrate 4211 has the unevenness illustrated in FIG. 7(B), whereby the extraction efficiency of light generated in the light-emitting element 4202 can be increased.

Application examples of such lighting devices include a ceiling light for indoor lighting. Examples of the ceiling light include a ceiling direct mount light and a ceiling embedded light. Such a lighting device is fabricated using the light-emitting device and a housing or a cover in combination.

For another example, such lighting devices can be used for a foot light that illuminates a floor so that safety on the floor can be improved. For example, the foot light can be effectively used in a bedroom, on a staircase, or on a passage. In that case, the size or shape of the foot light can be changed depending on the area or structure of a room. The foot light can be a stationary lighting device fabricated using the light-emitting device and a support base in combination.

Such lighting devices can also be used for a sheet-like lighting device (sheet-like lighting). The sheet-like lighting, which is attached to a wall when used, is space-saving and thus can be used for a wide variety of uses. Furthermore, the area of the sheet-like lighting can be increased. The sheet-like lighting can also be used on a wall or housing having a curved surface.

Besides the above examples, the light-emitting device which is one embodiment of the present invention or the light-emitting element which is a part of the light-emitting device can be used as part of furniture in a room, so that a lighting device which has a function of the furniture can be obtained.

As described above, a variety of lighting devices that include the light-emitting device can be obtained. Note that these lighting devices are also embodiments of the present invention.

The structure described in this embodiment can be combined with any of the structures described in the other embodiments as appropriate.

Example 1

Synthesis Example 1

Described in this synthesis example is a method for synthesizing 4,8-bis[3-(9,9-dimethylfluoren-2-yl)phenyl]-[1]benzofuro[3,2-d]pyrimidine (abbreviation: 4,8mFP2Bfpm), which is the organic compound of one embodiment of the present invention represented by Structural Formula (100) in Embodiment 1. Note that the structure of 4,8mFP2Bfpm is shown below.

[Chemical 21]

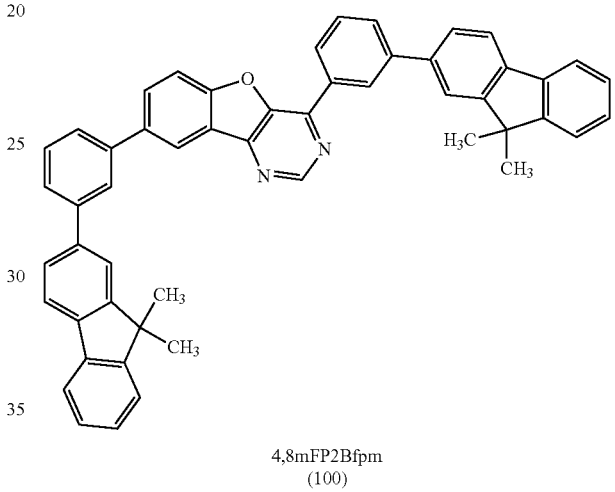

4,8mFP2Bfpm
(100)

<Synthesis of 4,8mFP2Bfpm>

First, 1.0 g of 4,8-dichloro[1]benzofuro[3,2-d]pyrimidine, 3.8 g of 3-(dimethylfluoren-2-yl)phenyl pinacol boron, 6.1 g of potassium phosphate, 100 mL of Diglyme, and 2.1 g of t-butanol were put into a flask, the atmosphere in the flask was replaced with nitrogen, 37 mg of palladium(II) acetate, 0.20 mg of di(1-adamantyl)-n-butylphosphine were added, and heating was performed under a nitrogen stream at 120° C. for 13 hours. Water and toluene were added to the obtained reactant and filtration was performed. The organic layer separated from the filtrate was washed with saturated brine, magnesium sulfate was added, and filtration was performed. The obtained filtrate was dried and solidified, and was then recrystallized with toluene to give 1.6 g of a pale yellow solid, which was the objective substance, in a yield of 55%. The synthesis scheme is shown in the following formula (a-1).

[Chemical 22]

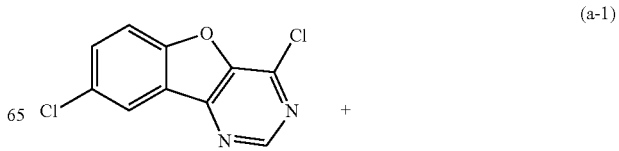

(a-1)

-continued

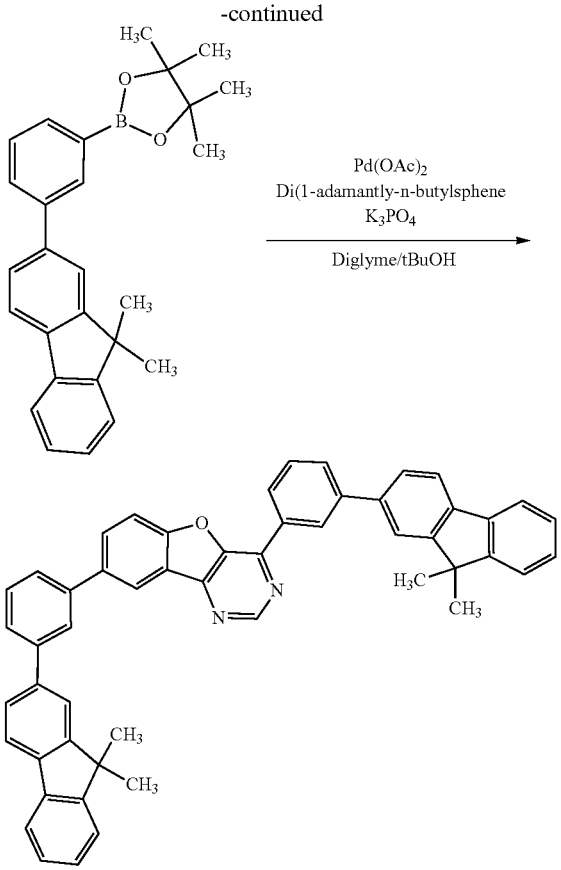

By the train sublimation method, 1.6 g of the pale yellow solid was sublimated and purified. The conditions of the sublimation purification were such that the solid was heated under a pressure of 2.6 Pa at 310° C. while the argon gas flowed at a flow rate of 5 mL/min. After the sublimation purification, 1.5 g of a yellow solid, which was the objective substance, was obtained at a yield of 94%.

Figure 8:
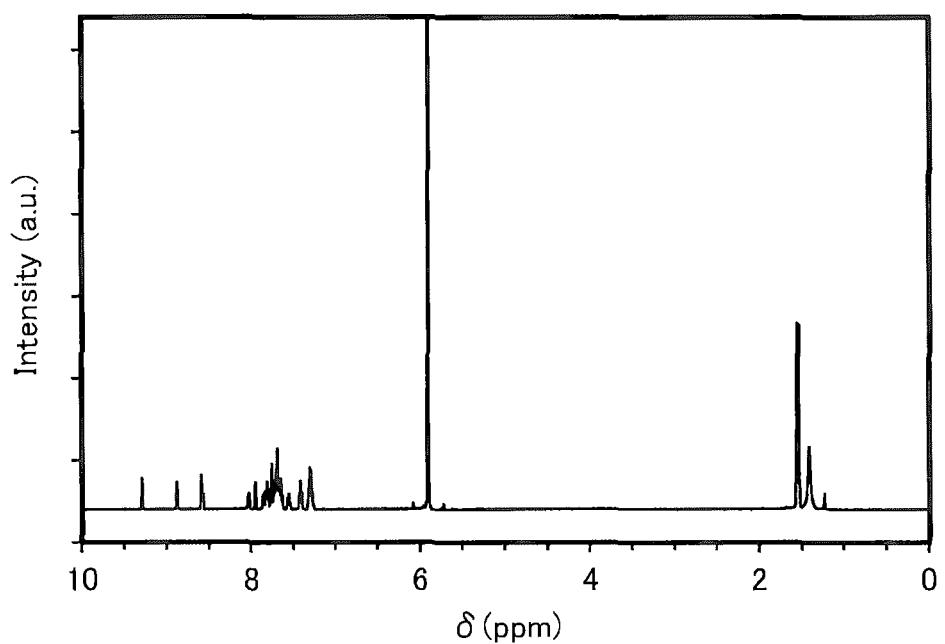
FIG. 8 is a $^1$H-NMR chart of an organic compound represented by Structural Formula (100).

The results of nuclear magnetic resonance ($^1$H-NMR) spectroscopy analysis of the obtained yellow solid are shown below. FIG. 8 shows a $^1$H-NMR chart. The results revealed that 4,8mFP2Bfpm, the organic compound represented by Structural Formula (100) above, was obtained in this example.

$^1$H-NMR. δ (TCE-d$_2$): 1.61 (d, 12H), 7.33-7.38 (m, 4H), 7.46-7.49 (t, 2H), 7.60-7.63 (t, 1H), 7.69-7.83 (m, 10), 7.86-7.89 (t, 2H), 7.90-7.92 (d, 1H), 8.01 (s, 1H), 8.09 (d, 1H), 8.64 (d, 2H), 8.94 (s, 1H), 9.35 (s, 1H).

Figure 9A:
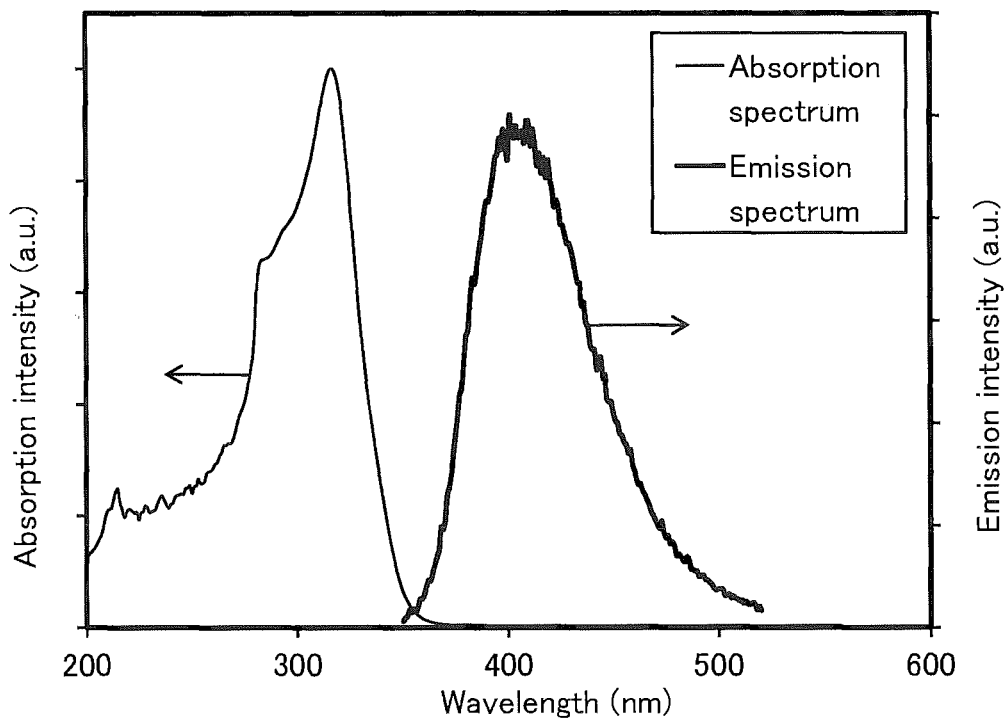
FIGS. 9A-9B are ultraviolet-visible absorption spectra and emission spectra of the organic compound represented by Structural Formula (100).

Next, FIG. 9(A) shows an ultraviolet-visible absorption spectrum (hereinafter, simply referred to as "absorption spectrum") and an emission spectrum of 4,8mFP2Bfpm in a toluene solution. The horizontal axis represents wavelength and the vertical axes represent absorption intensity and emission intensity.

The absorption spectrum was measured using an ultraviolet-visible spectrophotometer (V550, produced by JASCO Corporation). The absorption spectrum of 4,8mFP2Bfpm in the toluene solution was obtained by subtracting the measured absorption spectrum of toluene put in a quartz cell from the measured absorption spectrum of the toluene solution of 4,8mFP2Bfpm put in a quartz cell. The emission spectrum was measured using a fluorescence spectrophotometer (FS920 manufactured by Hamamatsu Photonics K.K.). The emission spectrum of 4,8mFP2Bfpm in the toluene solution was measured with the toluene solution of 4,8mFP2Bfpm put in a quartz cell.

As shown in FIG. 9(A), the toluene solution of 4,8mFP2Bfpm exhibited absorption peaks at around 283 nm and 315 nm and an emission wavelength peak at around 401 nm (excitation wavelength: 327 nm).

Figure 9B:
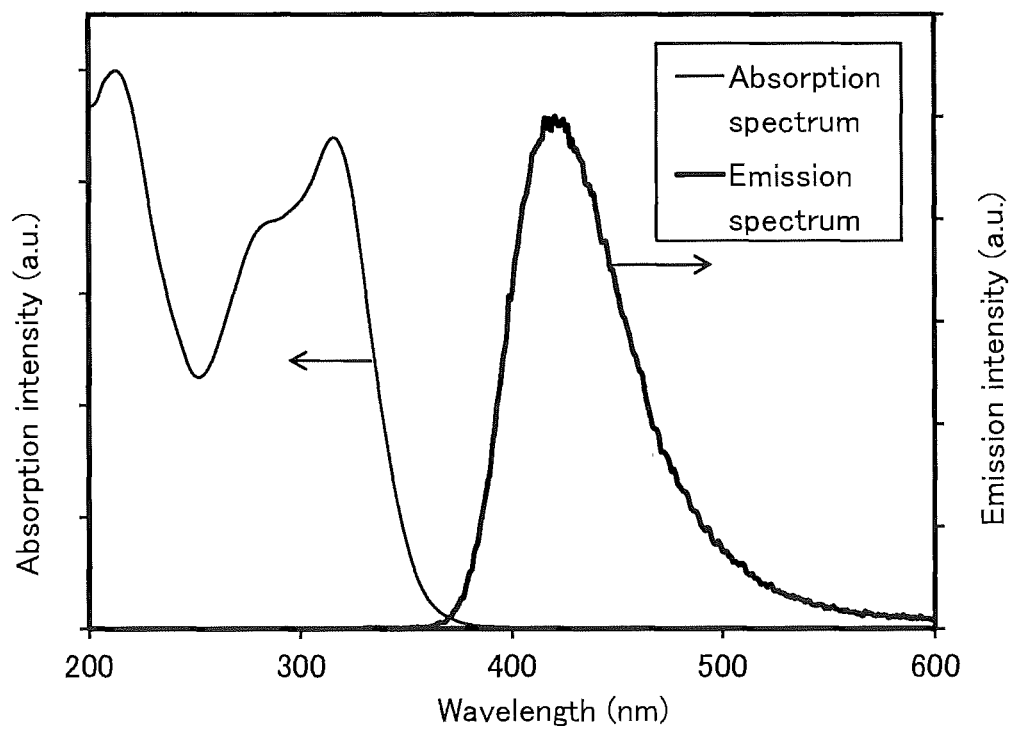

Next, an absorption spectrum and an emission spectrum of a solid thin film of 4,8mFP2Bfpm were measured. The solid thin film was formed over a quartz substrate by a vacuum evaporation method. The absorption spectrum of the thin film was calculated using an absorbance ($-\log_{10}$ [% T/(100−% R)]) obtained from a transmittance and a reflectance of the substrate and the thin film. Note that % T represents transmittance and % R represents reflectance. The absorption spectrum was measured using an ultraviolet-visible spectrophotometer (U-4100, manufactured by Hitachi High-Technologies Corporation). The emission spectra were measured using a fluorescence spectrophotometer (FS920 manufactured by Hamamatsu Photonics K.K.). FIG. 9(B) shows the measurement results of the obtained absorption spectrum and emission spectrum of the solid thin film. The horizontal axis represents wavelength and the vertical axes represent absorption intensity and emission intensity.

As shown by the results in FIG. 9(B), the solid thin film of 4,8mFP2Bfpm exhibited absorption peaks at around 213 nm, 282 nm, and 316 nm and an emission wavelength peak at around 422 nm (excitation wavelength: 322 nm).

Example 2

Figure 10:
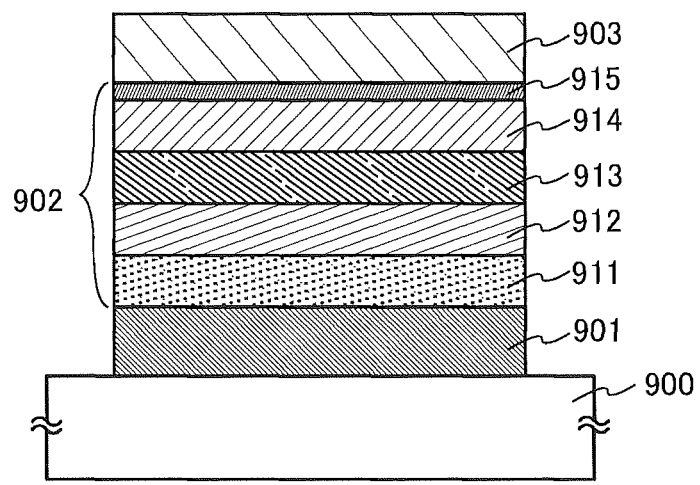
FIG. 10 is a drawing illustrating a light-emitting element.

In this example, the element structures, manufacturing methods, and characteristics of the light-emitting elements that are embodiments of the present invention, i.e., Light-emitting Element 1 whose light-emitting layer used 4,8-bis [3-(9,9-dimethylfluoren-2-yl)phenyl]-[1]benzofuro[3,2-d] pyrimidine (abbreviation: 4,8mFP2Bfpm) (Structural Formula (100)) described in Example 1 and Comparative Light-emitting Element 2 as a reference whose light-emitting layer used 4,6-bis[3-(9,9-dimethylfluoren-2-yl)phenyl] pyrimidine (abbreviation: 4,6mFP2Pm), are described. Note that FIG. 10 illustrates the element structure of the light-emitting elements used in this example, and Table 1 shows specific structures. Chemical formulae of materials used in this example are shown below.

TABLE 1

| | First electrode | Hole-injection layer | Hole-transport layer | Light-emitting layer | Electron-transport layer | Electron-injection layer | Second electrode |
|---|---|---|---|---|---|---|---|
| Light-emitting Element 1 | ITSO (70 nm) | DBT3P-II:MoOx (2:1 50 nm) | PCBBi1BP (20 nm) | * | 4,8mFP2Bfpm (20 nm) | Bphen (15 nm) | LiF (1 nm) | Al (200 nm) |

TABLE 1-continued

| | First electrode | Hole-injection layer | Hole-transport layer | Light-emitting layer | Electron-transport layer | | Electron-injection layer | Second electrode |
|---|---|---|---|---|---|---|---|---|
| Comparative Light-emitting Element 2 | ITSO (70 nm) | DBT3P-II:MoOx (2:1 50 nm) | PCBBi1BP (20 nm) | ** | 4,6mFP2Pm (20 nm) | Bphen (15 nm) | LiF (1 nm) | Al (200 nm) |

*4,8mFP2Bfpm:PCCP:[Ir(ppy)$_2$(4dppy)] (0.6:0.4:0.1 40 nm)
**4,6mFP2Pm:PCCP:[Ir(ppy)$_2$(4dppy)] (0.6:0.4:0.1 40 nm)

[Chemical 23]

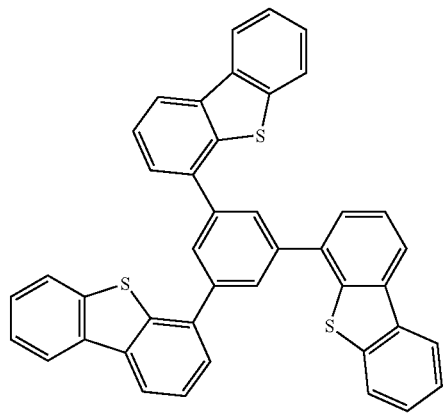

DBT3P-II

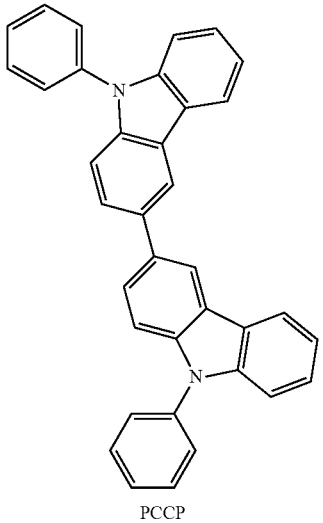

PCCP

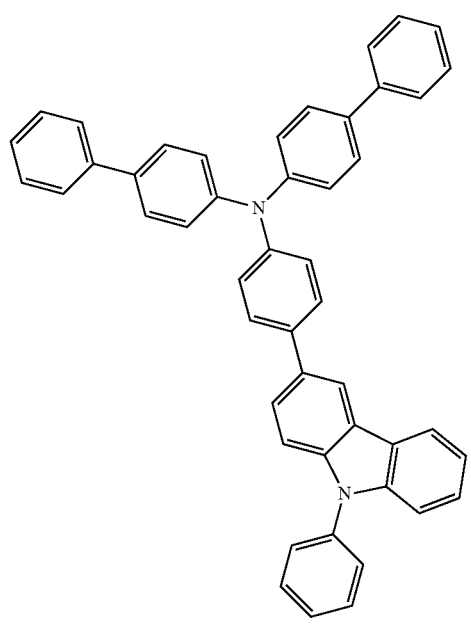

PCBBi1BP 4,8mFP2Bfpm
(100)

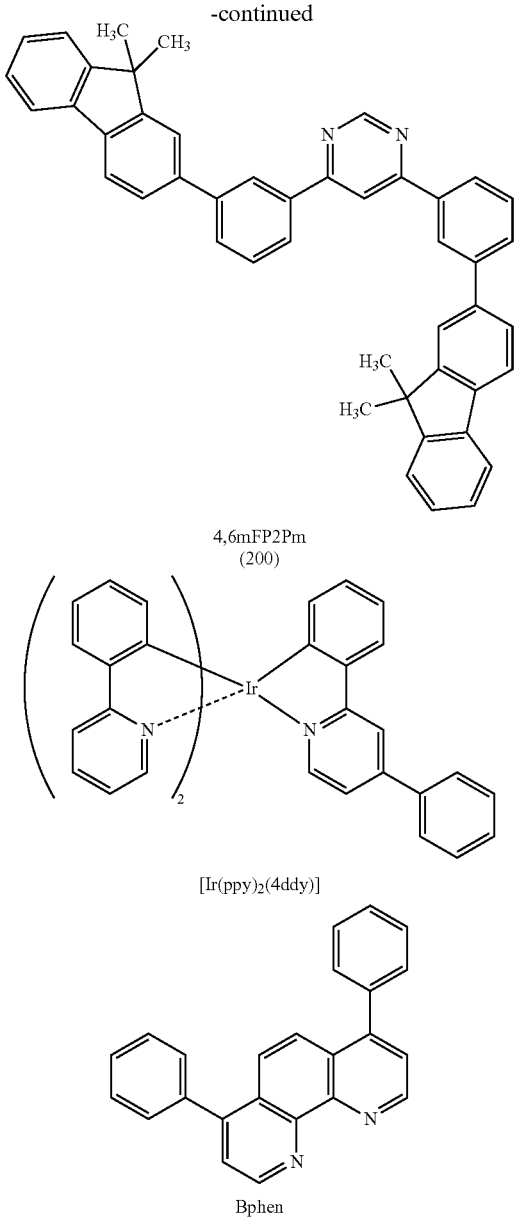

4,6mFP2Pm
(200)

[Ir(ppy)₂(4ddy)]

Bphen

<<Fabrication of Light-Emitting Elements>>

The light-emitting elements described in this example have a structure as illustrated in FIG. 10, in which a hole-injection layer 911, a hole-transport layer 912, a light-emitting layer 913, an electron-transport layer 914, and an electron-injection layer 915 are stacked in this order over a first electrode 901 formed over a substrate 900, and a second electrode 903 is stacked over the electron-injection layer 915.

First, the first electrode 901 was formed over the substrate 900. The electrode area was set to 4 mm² (2 mm×2 mm). A glass substrate was used as the substrate 900. The first electrode 901 was formed to a thickness of 70 nm using indium tin oxide containing silicon oxide (ITSO) by a sputtering method.

As pretreatment, a surface of the substrate was washed with water, baking was performed at 200° C. for one hour, and then UV ozone treatment was performed for 370 seconds. After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the hole-injection layer 911 was formed over the first electrode 901. For the formation of the hole-injection layer 911, the pressure in the vacuum evaporation apparatus was reduced to $10^{-4}$ Pa, and then 1,3,5-tri(dibenzothiophen-4-yl)benzene (abbreviation: DBT3P-II) and molybdenum oxide were co-evaporated such that DBT3P-II:molybdenum oxide=2:1 (mass ratio) and the thickness was 50 nm.

Then, the hole-transport layer 912 was formed over the hole-injection layer 911. The hole-transport layer 912 was formed to a thickness of 20 nm by evaporation using 4,4'-diphenyl-4''-(9-phenyl-9H-carbazol-3-yl)triphenylamine (abbreviation: PCBBi1BP).

Next, the light-emitting layer 913 was formed over the hole-transport layer 912.

For the light-emitting layer 913 in Light-emitting Element 1, co-evaporation using 4,8mFP2Bfpm (100) as a host material, PCCP as an assist material, and [Ir(ppy)₂(4dppy)] as a guest material (a phosphorescent material) was performed such that the weight ratio was 4,8mFP2Bfpm:PCCP:[Ir(ppy)₂(4dppy)]=0.6:0.4:0.1. The thickness was set to 40 nm.

For the light-emitting layer 913 in Comparative Light-emitting Element 2, co-evaporation using 4,6mFP2Pm (200) as a host material, PCCP as an assist material, and [Ir(ppy)₂(4dppy)] as a guest material (a phosphorescent material) was performed such that the weight ratio was 4,6mFP2Pm:PCCP:[Ir(ppy)₂(4dppy)]=0.6:0.4:0.1. The thickness was set to 40 nm.

Next, the electron-transport layer 914 was formed over the light-emitting layer 913. The electron-transport layer 914 in Light-emitting Element 1 was formed in the following manner: 4,8mFP2Bfpm and bathophenanthroline (abbreviation: Bphen) were sequentially deposited by evaporation to thicknesses of 20 nm and 15 nm, respectively. The electron-transport layer 914 in Comparative Light-emitting Element 2 was formed in the following manner: 4,6mFP2Pm and Bphen were sequentially deposited by evaporation to thicknesses of 20 nm and 15 nm, respectively.

Then, the electron-injection layer 915 was formed over the electron-transport layer 914. The electron-injection layer 915 was formed to a thickness of 1 nm by evaporation using lithium fluoride (LiF).

After that, the second electrode 903 was formed over the electron-injection layer 915. The second electrode 903 was formed using aluminum to a thickness of 200 nm by an evaporation method. In this example, the second electrode 903 functions as a cathode.

Through the above steps, the light-emitting elements in each of which an EL layer was provided between a pair of electrodes over the substrate 900 were fabricated. The hole-injection layer 911, the hole-transport layer 912, the light-emitting layer 913, the electron-transport layer 914, and the electron-injection layer 915 described in the above steps were functional layers forming the EL layer in one embodiment of the present invention. Furthermore, in all the evaporation steps in the above fabrication method, an evaporation method by a resistance-heating method was used.

The light-emitting elements fabricated as described above were sealed using another substrate (not illustrated). At the time of the sealing using the another substrate (not illustrated), the another substrate (not illustrated) on which a sealant that solidifies by ultraviolet light was applied was fixed onto the substrate 900 in a glove box containing a nitrogen atmosphere, and the substrates were bonded to each other such that the sealant attached to the periphery of the light-emitting element formed over the substrate 900. At the time of the sealing, the sealant was irradiated with 365-nm ultraviolet light at 6 J/cm$^2$ to be solidified, and the sealant was subjected to heat treatment at 80° C. for one hour to be stabilized.

<<Operation Characteristics of Light-Emitting Elements>>

Figure 11:
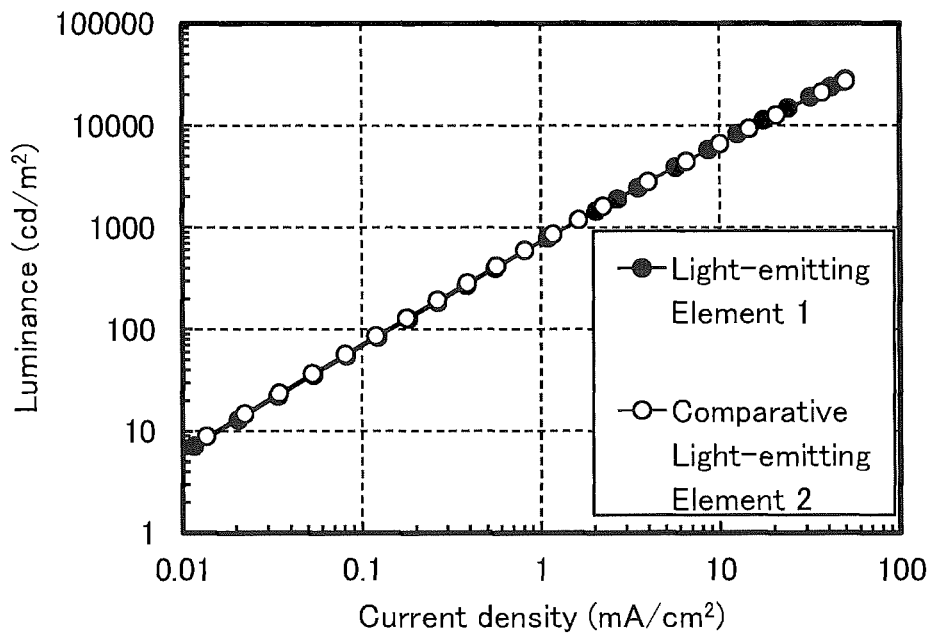
FIG. 11 is a graph showing current density-luminance characteristics of Light-emitting Element 1 and Comparative Light-emitting Element 2.
Figure 12:
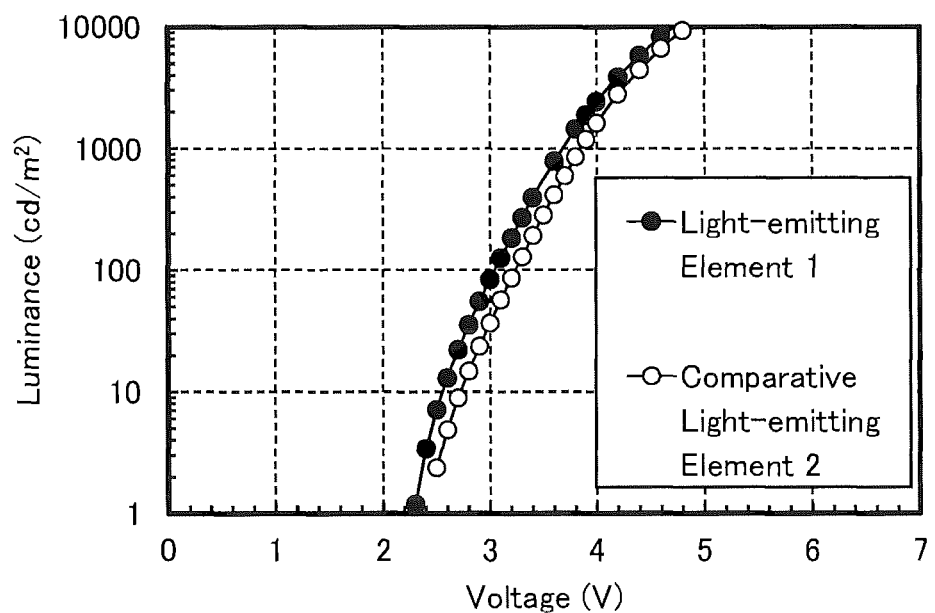
FIG. 12 is a graph showing voltage-luminance characteristics of Light-emitting Element 1 and Comparative Light-emitting Element 2.
Figure 13:
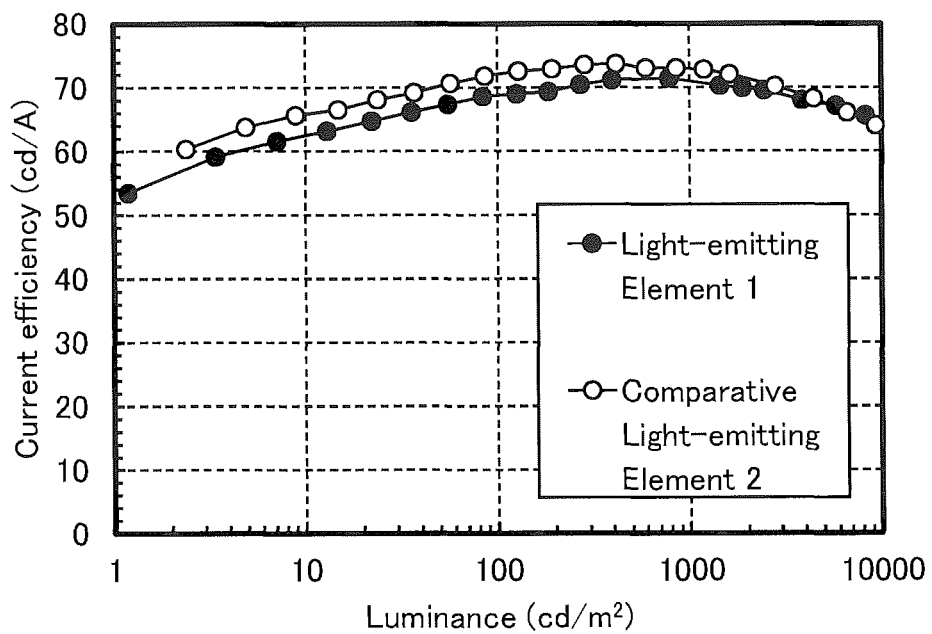
FIG. 13 is a graph showing luminance-current efficiency characteristics of Light-emitting Element 1 and Comparative Light-emitting Element 2.
Figure 14:
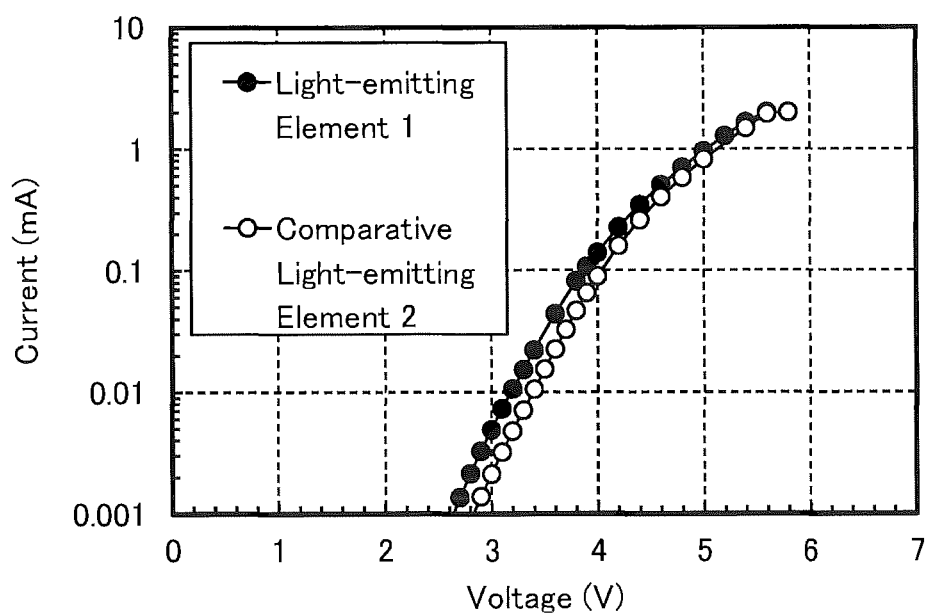
FIG. 14 is a graph showing voltage-current characteristics of Light-emitting Element 1 and Comparative Light-emitting Element 2.

Operation characteristics of each of the fabricated light-emitting elements were measured. Note that the measurement was carried out at room temperature (an atmosphere maintained at 25° C.). As the results of the operation characteristics of the light-emitting elements, the current density-luminance characteristics are shown in FIG. 11, the voltage-luminance characteristics are shown in FIG. 12, the luminance-current efficiency characteristics are shown in FIG. 13, and the voltage-current characteristics are shown in FIG. 14.

Table 2 below shows initial values of main characteristics of each of the light-emitting elements at around 1000 cd/m$^2$.

The results of the reliability tests show that Light-emitting Element 1 has higher reliability than Comparative Light-emitting Element 2 although their efficiencies shown in Table 2 are substantially the same. This is probably because in the comparison between 4,8mFP2Bfpm used in Light-emitting Element 1 and 4,6mFP2Pm used in Comparative Light-emitting Element 2, the benzofuropyrimidine skeleton of 4,8mFP2Bfpm has higher structural stability and rigidity than the pyrimidine skeleton of 4,6mFP2Pm, which is a skeleton portion with an electron-transport property. Thus, it is indicated that the use of 4,8mFP2Bfpm (Structural Formula (100)), which is the organic compound of one embodiment of the present invention, is effective in improving the reliability of the light-emitting element.

TABLE 2

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting Element 1 | 3.6 | 0.044 | 1.1 | (0.46, 0.53) | 780 | 71 | 62 | 22 |
| Comparative Light-emitting Element 2 | 3.8 | 0.047 | 1.2 | (0.46, 0.53) | 850 | 73 | 60 | 23 |

The above results show that the light-emitting elements fabricated in this example exhibit excellent efficiencies.

Figure 15:
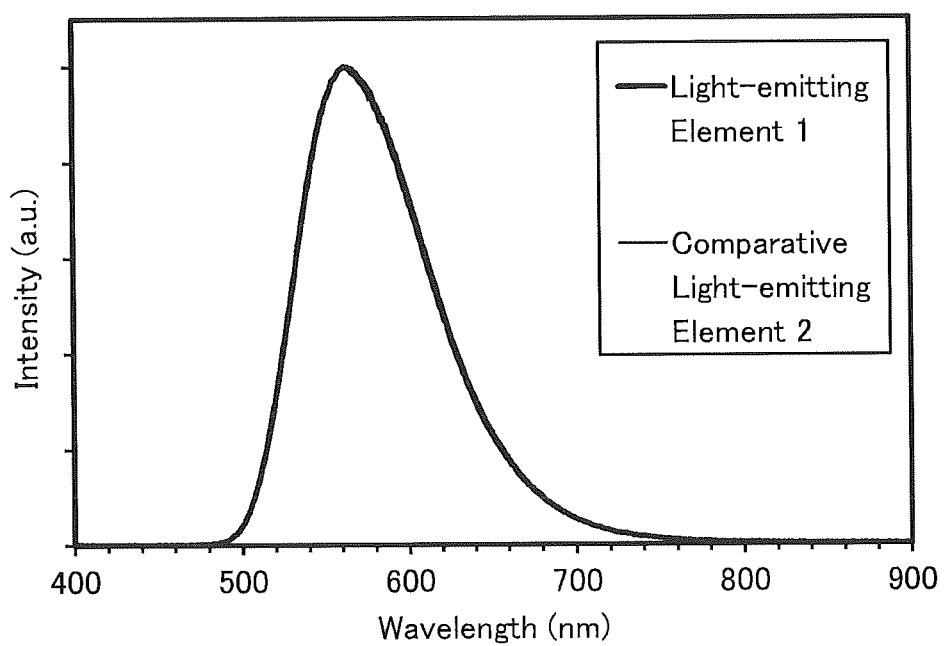
FIG. 15 is a graph showing emission spectra of Light-emitting Element 1 and Comparative Light-emitting Element 2.

FIG. 15 shows emission spectra in the case where current at a current density of 2.5 mA/cm$^2$ was supplied to Light-emitting Element 1 and Comparative Light-emitting Element 2. As shown in FIG. 15, the emission spectra of Light-emitting Element 1 and Comparative Light-emitting Element 2 have peaks at around 563 nm, and it is suggested that each peak was derived from light emission of [Ir(ppy)$_2$(4dppy)] contained in the light-emitting layer 913.

Figure 16:
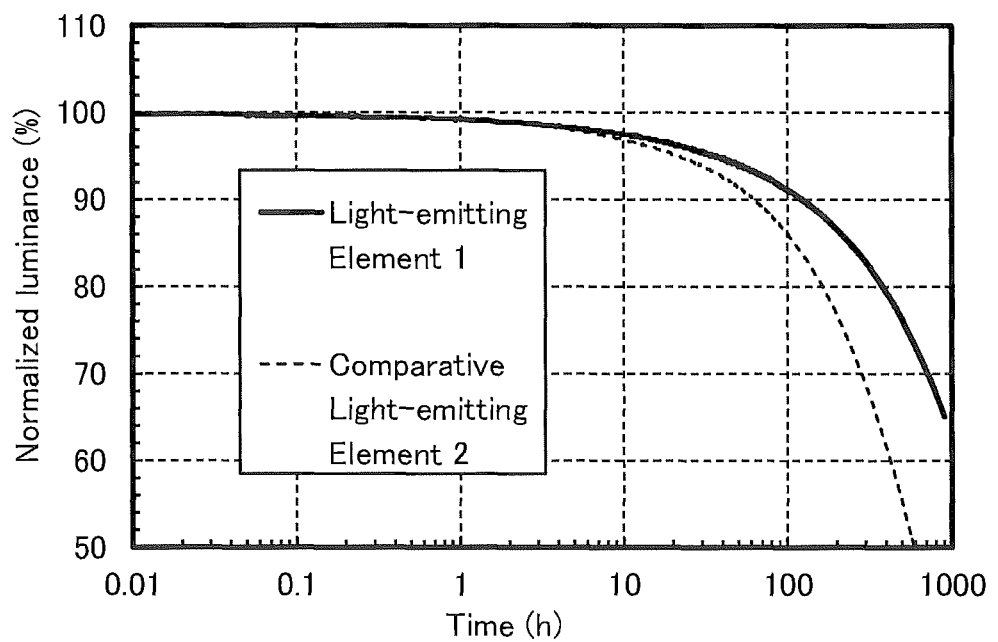
FIG. 16 is a graph showing reliability of Light-emitting Element 1 and Comparative Light-emitting Element 2.

Next, reliability tests were performed on Light-emitting Element 1 and Comparative Light-emitting Element 2. FIG. 16 shows the results of the reliability tests. In FIG. 16, the vertical axis represents normalized luminance (%) with an initial luminance of 100%, and the horizontal axis represents driving time (h) of the elements. As the reliability tests, constant current driving tests where a constant current was supplied at a current density of 50 mA/cm$^2$ were performed.

Example 3

Synthesis Example 2

Described in this synthesis example is a method for synthesizing 4,8-bis[3-(triphenylen-2-yl)phenyl]-[1]benzofuro[3,2-d]pyrimidine (abbreviation: 4,8mTpP2Bfpm), which is the organic compound of one embodiment of the present invention represented by Structural Formula (130) in Embodiment 1. Note that the structure of 4,8mTpP2Bfpm is shown below.

[Chemical 24]

(130)

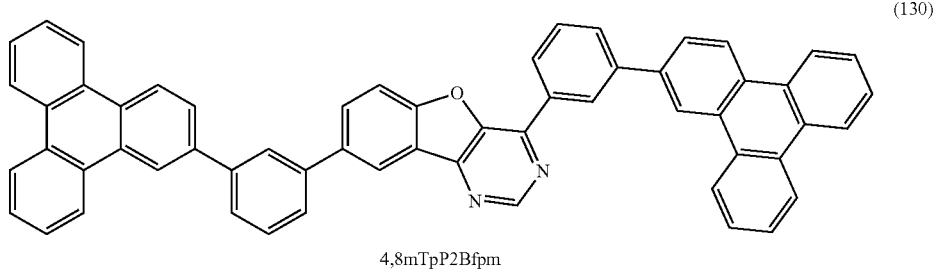

4,8mTpP2Bfpm

<Synthesis of 4,8mTpP2Bfpm>

Into a three-neck flask were put 1.20 g of 4,8-dichloro[1]benzofuro[3,2-d]pyrimidine, 4.52 g of 4,4,5,5-tetramethyl-2-[3-(triphenylen-2-yl)phenyl]-1,3,2-dioxaborolane, 3.19 g of tripotassium phosphate, 1.12 g of t-butanol, and 50 mL of diethylene glycol dimethyl ether (diglyme), degassing was performed by stirring under a reduced pressure, and the air in the flask was replaced with nitrogen.

This mixture was heated at 60° C. and 34.5 mg of palladium(II) acetate and 0.111 g of di(1-adamantyl)-n-butylphosphine were added, followed by stirring at 100° C. for 40.5 hours.

To this mixture, 34.0 mg of palladium(II) acetate and 0.114 g of di(1-adamantyl)-n-butylphosphine were added, followed by stirring at 120° C. for 39.5 hours.

Water was added to the obtained reaction liquid, suction filtration was performed, and the resulting residue was washed with water and ethyl acetate. This residue was dissolved in heated toluene, followed by filtration through a filter aid filled with Celite, alumina, and Celite in this order. The obtained solution was concentrated and dried, and the resulting solid was washed with heated toluene, whereby 1.43 g of a white solid, which was the objective substance, was obtained in a yield of 37%.

By a train sublimation method, 1.43 g of the white solid was sublimated and purified. The conditions of the sublimation purification were such that the solid was heated under a pressure of $1.5 \times 10^{-2}$ Pa at 300° C. After the sublimation purification, 1.03 g of a pale yellow solid, which was the objective substance, was obtained at a collection rate of 72%. The synthesis scheme is shown in the following formula (b-1).

The horizontal axis represents wavelength and the vertical axes represent absorption intensity and emission intensity.

The absorption spectrum was measured using an ultraviolet-visible spectrophotometer (V550, produced by JASCO Corporation). The emission spectrum was measured using a fluorescence spectrophotometer (FS920 manufactured by Hamamatsu Photonics K.K.).

Figure 18A:
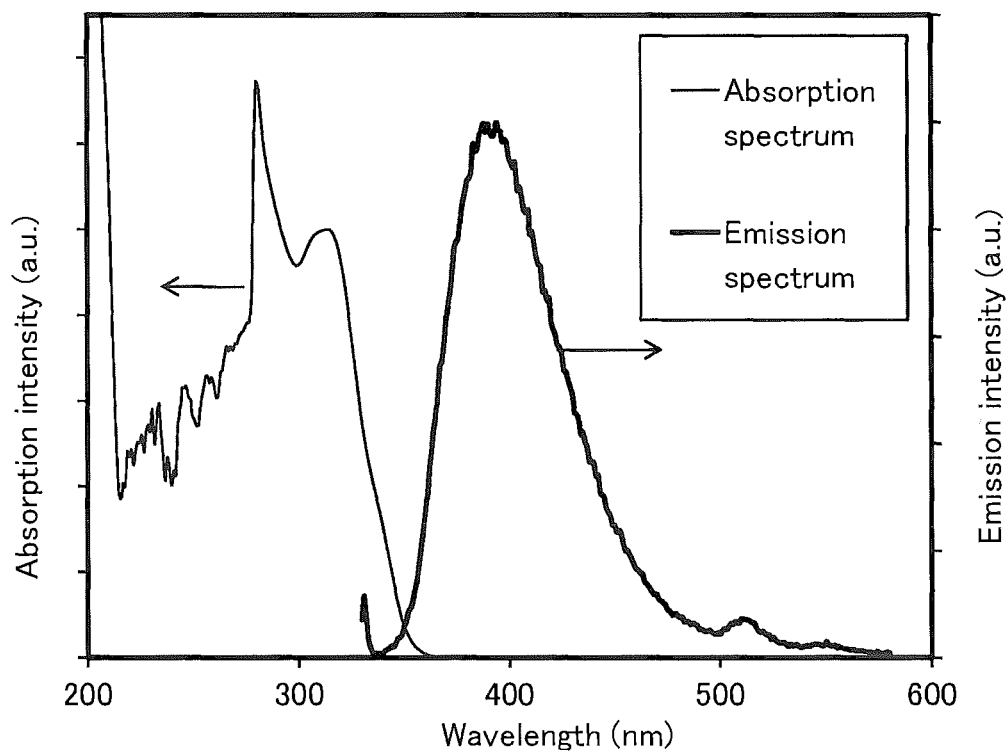
FIGS. 18A-18B are ultraviolet-visible absorption spectra and emission spectra of the organic compound represented by Structural Formula (130).

As shown in FIG. 18(A), the toluene solution of 4,8mTpP2Bfpm exhibited absorption peaks at around 335 nm, 314 nm, and 280 nm and an emission wavelength peak at around 394 nm (excitation wavelength: 300 nm).

Figure 18B:
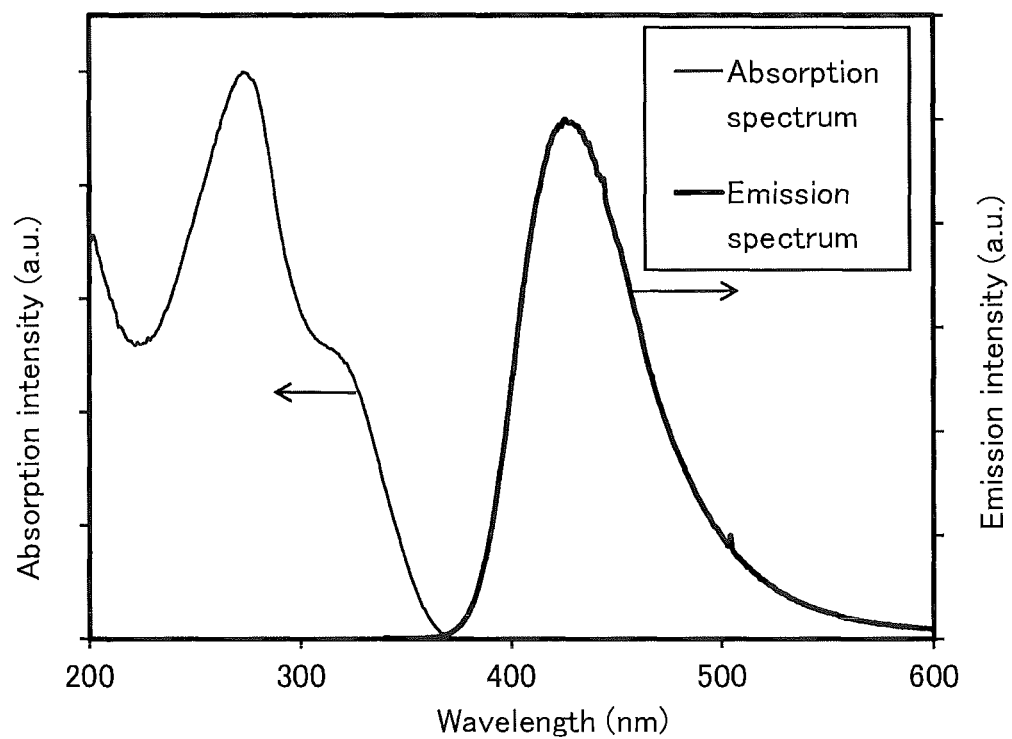

Next, an absorption spectrum and an emission spectrum of a solid thin film of 4,8mTpP2Bfpm were measured. The solid thin film was formed over a quartz substrate by a vacuum evaporation method. The absorption spectrum was measured with an ultraviolet-visible spectrophotometer (U-4100, manufactured by Hitachi High-Technologies Corporation). The emission spectra were measured using a fluorescence spectrophotometer (FS920 manufactured by Hamamatsu Photonics K.K.). FIG. 18(B) shows the measurement results of the obtained absorption spectrum and emission spectrum of the solid thin film. The horizontal axis represents wavelength and the vertical axes represent absorption intensity and emission intensity.

As shown by the results in FIG. 18(B), the solid thin film of 4,8mTpP2Bfpm exhibited absorption peaks at around 315

[Chemical 25]

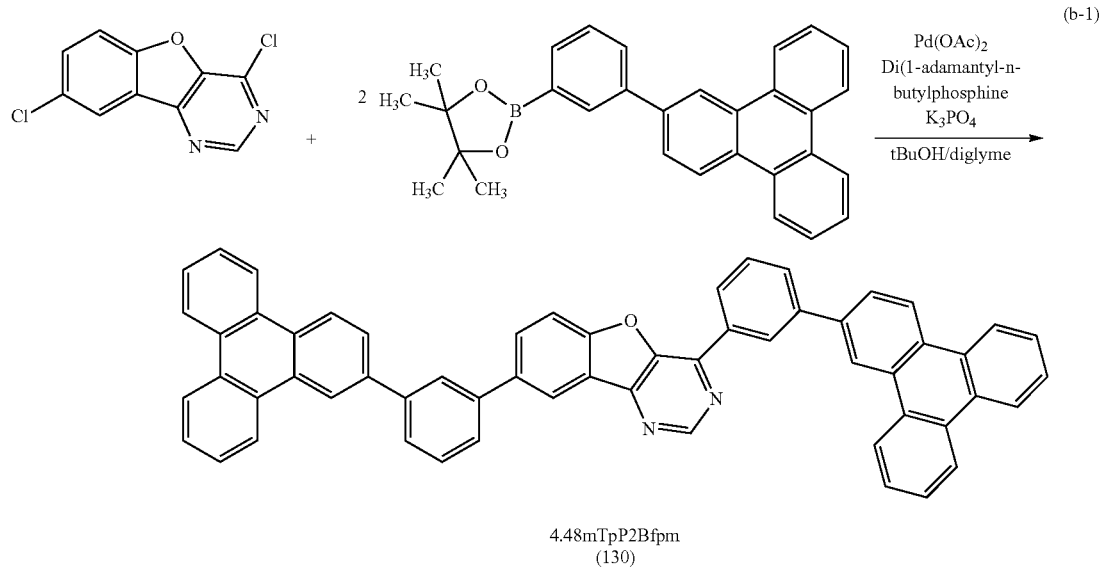

Figure 17:
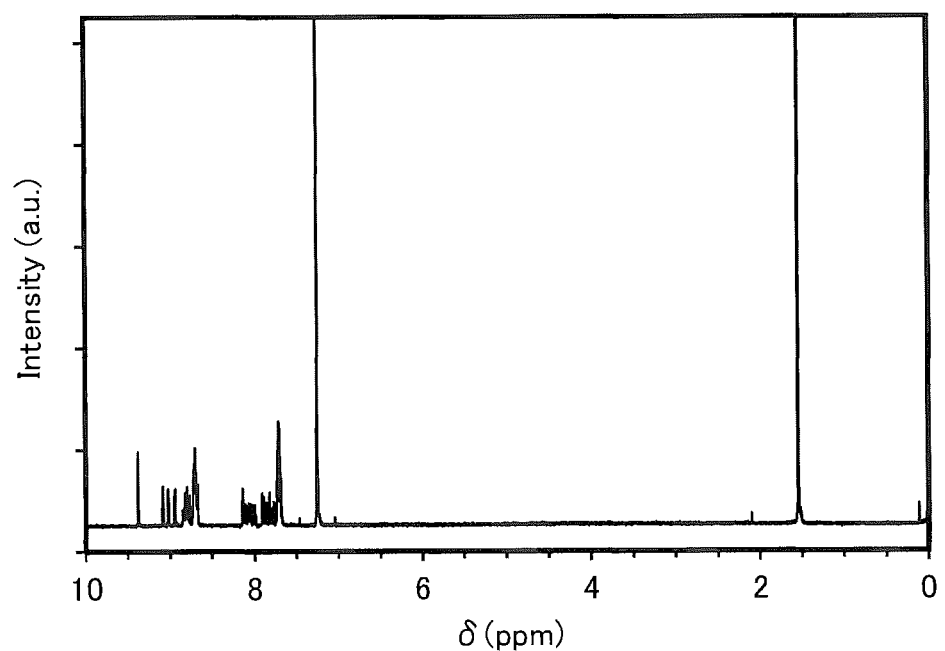
FIG. 17 is a $^1$H-NMR chart of an organic compound represented by Structural Formula (130).

The results of nuclear magnetic resonance ($^1$H-NMR) spectroscopy analysis of the obtained yellow solid are shown below. FIG. 17 shows a $^1$H-NMR chart. The results revealed that 4,8mTpP2Bfpm, the organic compound represented by Structural Formula (130) above, was obtained in this example.

$^1$H-NMR. δ (CDCl$_3$): 7.68-7.75 (m, 9H), 7.78 (d, 1H), 7.82 (t, 1H), 7.87 (d, 1H), 7.90 (d, 1H), 8.00 (d, 1H), 8.05 (d, 1H), 8.08 (d, 1H), 8.12 (d, 1H), 8.14 (s, 1H), 8.68-8.74 (m, 8H), 8.78 (d, 1H), 8.80-8.82 (m, 2H), 8.84-8.86 (m, 1H), 8.95 (s, 1H), 9.03 (s, 1H), 9.09 (s, 1H), 9.38 (s, 1H).

Next, FIG. 18(A) shows an absorption spectrum and an emission spectrum of 4,8mTpP2Bfpm in a toluene solution.

nm and 273 nm and an emission wavelength peak at around 426 nm (excitation wavelength: 330 nm).

Differential scanning calorimetry (DSC measurement) was performed for 4,8mTpP2Bfpm. For the measurement, Pyris 1 DSC manufactured by PerkinElmer, Inc. was used. Note that in the measurement, the operation in which the temperature was raised from −10° C. to 480° C. at a rate of 40° C./min, maintained at 480° C. for one minute, and then lowered from 480° C. to −10° C. at a rate of 100° C./min was regarded as one cycle, and two cycles of this operation were performed; then, the operation in which the temperature was raised from −10° C. to 480° C. at a rate of 10° C./min, maintained at 480° C. for one minute, and then lowered from 480° C. to −10° C. at a rate of 100° C./min was conducted as the third cycle.

In this measurement, the measurement was performed three cycles, and the result at the rising temperature in the third cycle revealed that the glass transition temperature: $T_g$ was 167° C. The results indicated that 4,8mTpP2Bfpm is a highly heat-resistant material.

Example 4

In this example, the light-emitting element that is one embodiment of the present invention, i.e., Light-emitting Element 3 whose light-emitting layer and electron-transport layer used 4,8-bis[3-(triphenylen-2-yl)phenyl]-[1]benzofuro[3,2-d]pyrimidine (abbreviation: 4,8mTpP2Bfpm) (Structural Formula (130)) described in Example 3, was fabricated and the measurement results of its characteristics are described.

The element structure of Light-emitting Element 3 fabricated in this example is similar to that in FIG. 10 mentioned in Example 2, and specific compositions of layers that constitute the element structure are as shown in Table 3. Chemical formulae of materials used in this example are shown below.

TABLE 3

| | First electrode | Hole-injection layer | Hole-transport layer | Light-emitting layer | Electron-transport layer | Electron-injection layer | Second electrode |
|---|---|---|---|---|---|---|---|
| Light-emitting Element 3 | ITSO (70 nm) | DBT3P-II:MoOx (2:1 50 nm) | PCBBi1BP (20 nm) | * | 4,8mTpP2Bfpm (20 nm) | NBphen (15 nm) | LiF (1 nm) | Al (200 nm) |

*4,8mTpP2Bfpm:PCCP:[Ir(ppy)$_2$(4dppy)] (0.6:0.4:0.1 40 nm)

[Chemical 26]

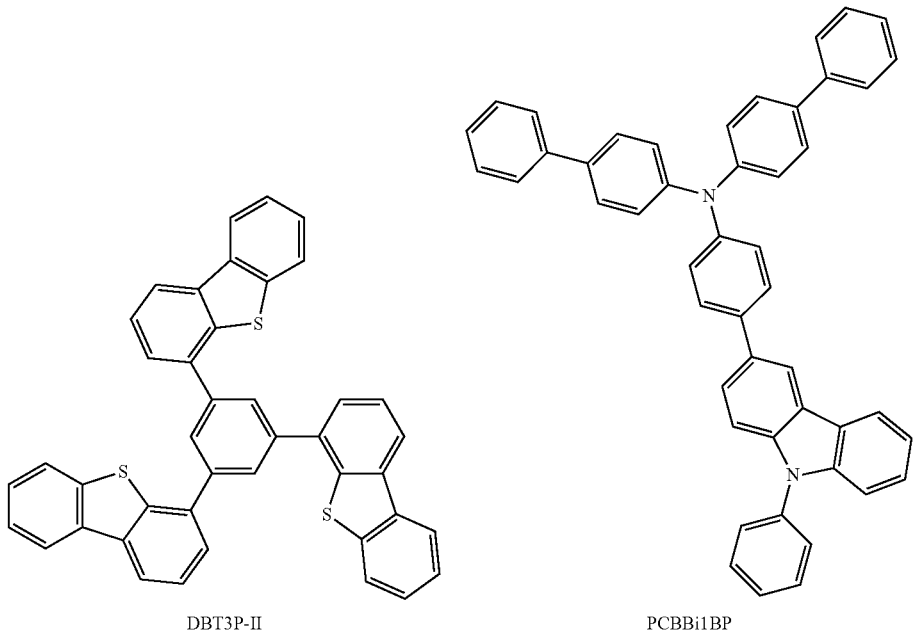

DBT3P-II                              PCBBi1BP

-continued

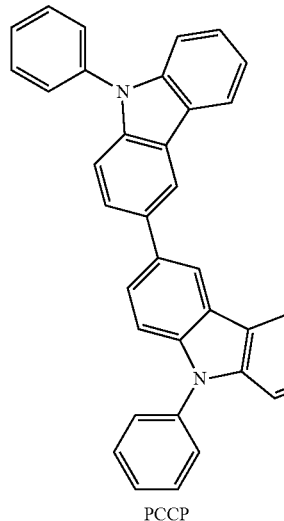
PCCP

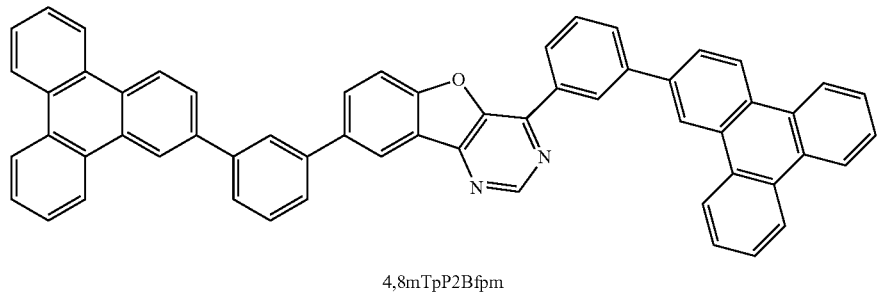
4,8mTpP2Bfpm
(130)

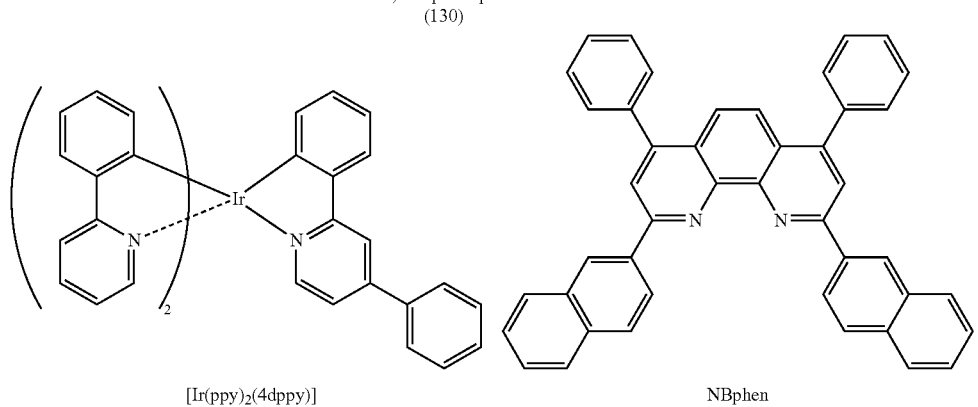

[Ir(ppy)₂(4dppy)]      NBphen

<<Operation Characteristics of Light-Emitting Element 3>>

Operation characteristics of Light-emitting Element 3 fabricated were measured. Note that the measurement was carried out at room temperature (an atmosphere maintained at 25° C.).

Figure 19:
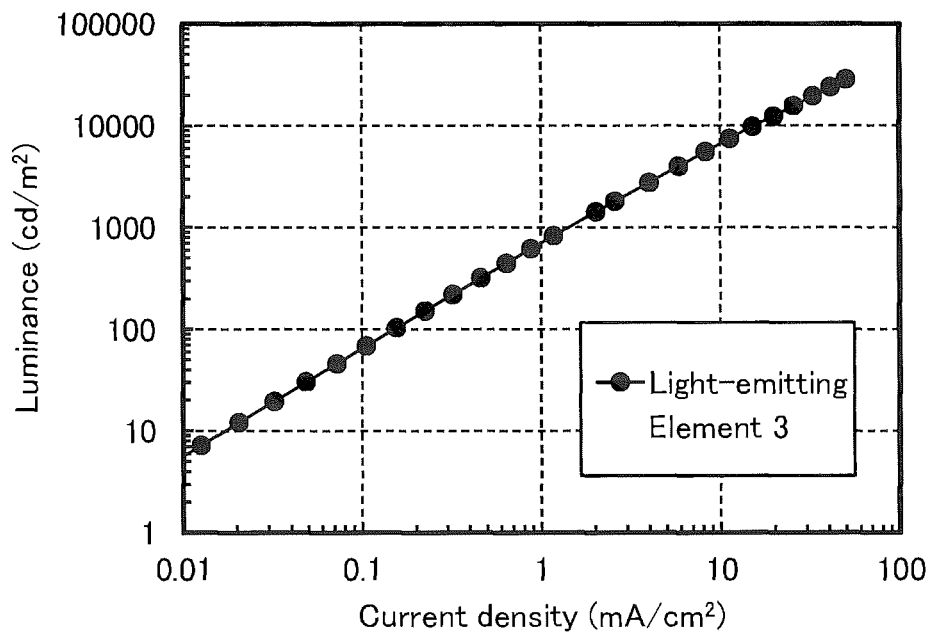
FIG. 19 is a graph showing current density-luminance characteristics of Light-emitting Element 3.
Figure 20:
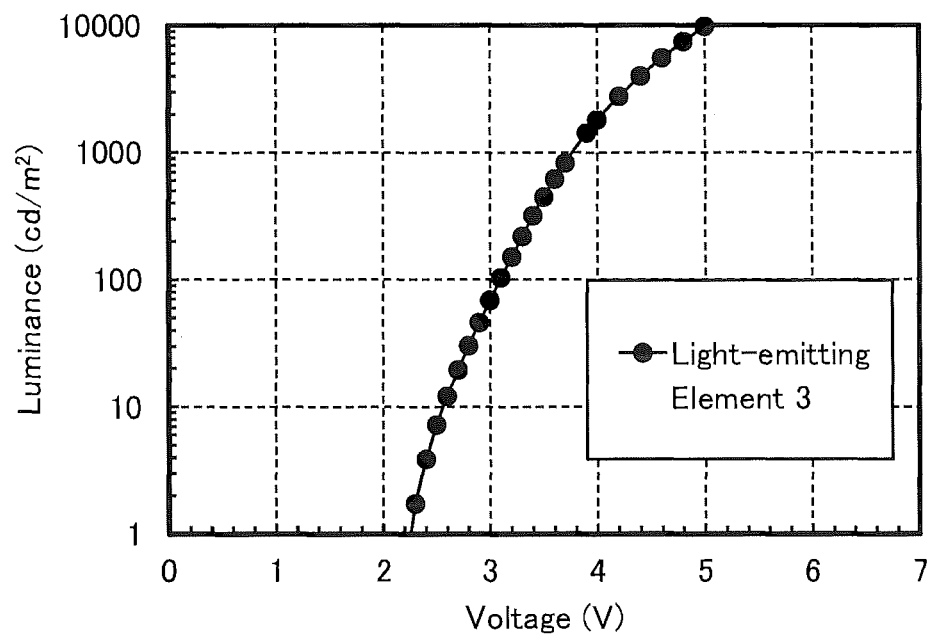
FIG. 20 is a graph showing voltage-luminance characteristics of Light-emitting Element 3.
Figure 21:
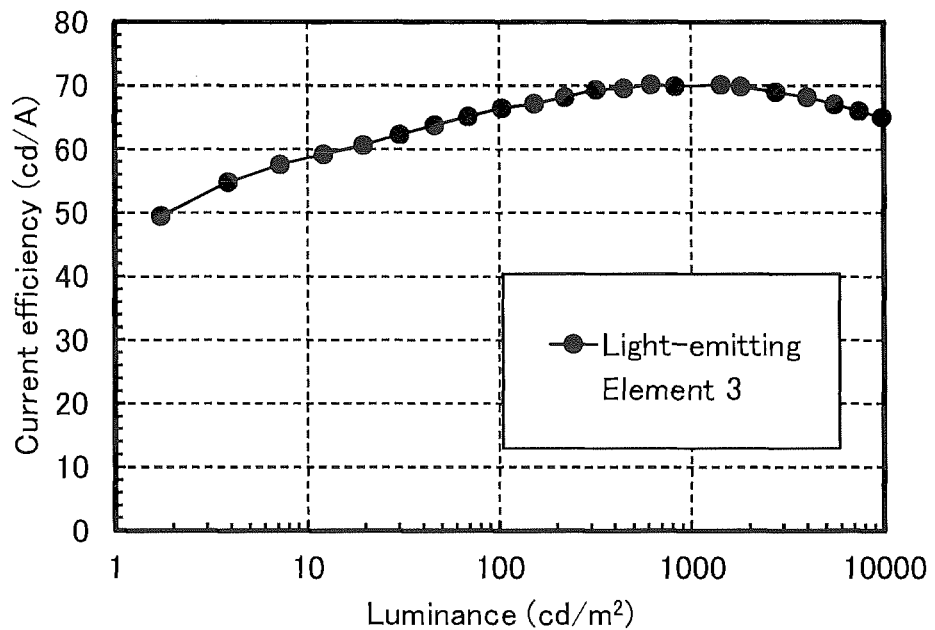
FIG. 21 is a graph showing luminance-current efficiency characteristics of Light-emitting Element 3.
Figure 22:
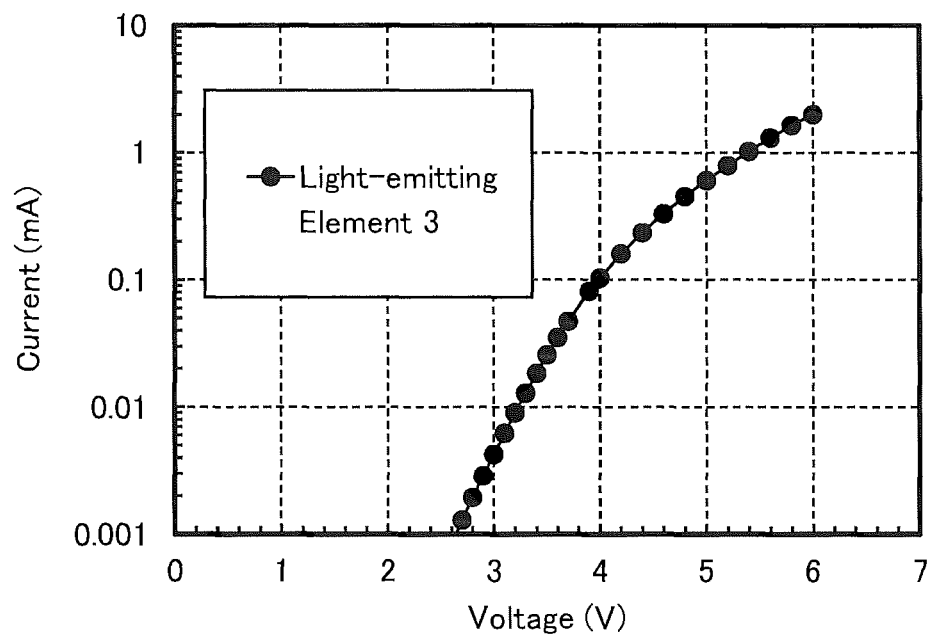
FIG. 22 is a graph showing voltage-current characteristics of Light-emitting Element 3.

The current density-luminance characteristics of Light-emitting Element 3 are shown in FIG. 19, the voltage-luminance characteristics are shown in FIG. 20, the luminance-current efficiency characteristics are shown in FIG. 21, and the voltage-current characteristics are shown in FIG. 22.

Table 4 below shows initial values of main characteristics of Light-emitting Element 3 at around 1000 cd/m².

TABLE 4

| | Voltage (V) | Current (mA) | Current density (mA/cm²) | Chromaticity (x, y) | Luminance (cd/m²) | Current efficiency (cd/A) | Power efficiency (lm/W) | External quantum efficiency (%) |
|---|---|---|---|---|---|---|---|---|
| Light-emitting Element 3 | 3.7 | 0.047 | 1.2 | (0.45, 0.54) | 830 | 70 | 59 | 21 |

The above results show that Light-emitting Element 3 fabricated in this example exhibits excellent efficiency.

Figure 23:
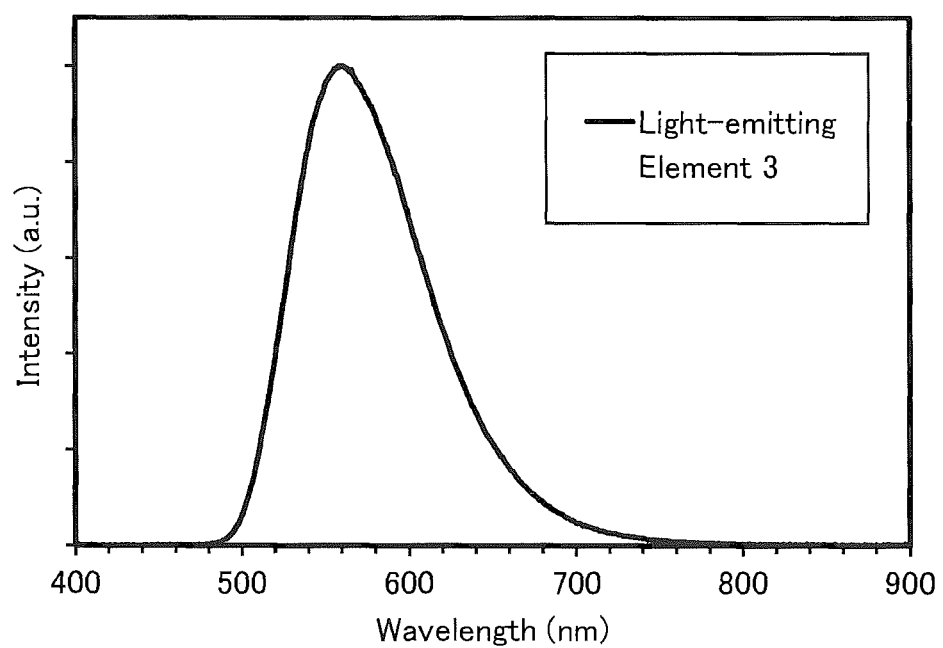
FIG. 23 is a graph showing an emission spectrum of Light-emitting Element 3.

FIG. 23 shows emission spectra in the case where current at a current density of 2.5 mA/cm² was supplied to Light-emitting Element 3. As shown in FIG. 23, the emission spectrum of Light-emitting Element 3 has a peak at around 561 nm, and it is suggested that the peak was derived from light emission of [Ir(ppy)₂(4dppy)] contained in the light-emitting layer 913.

Figure 24:
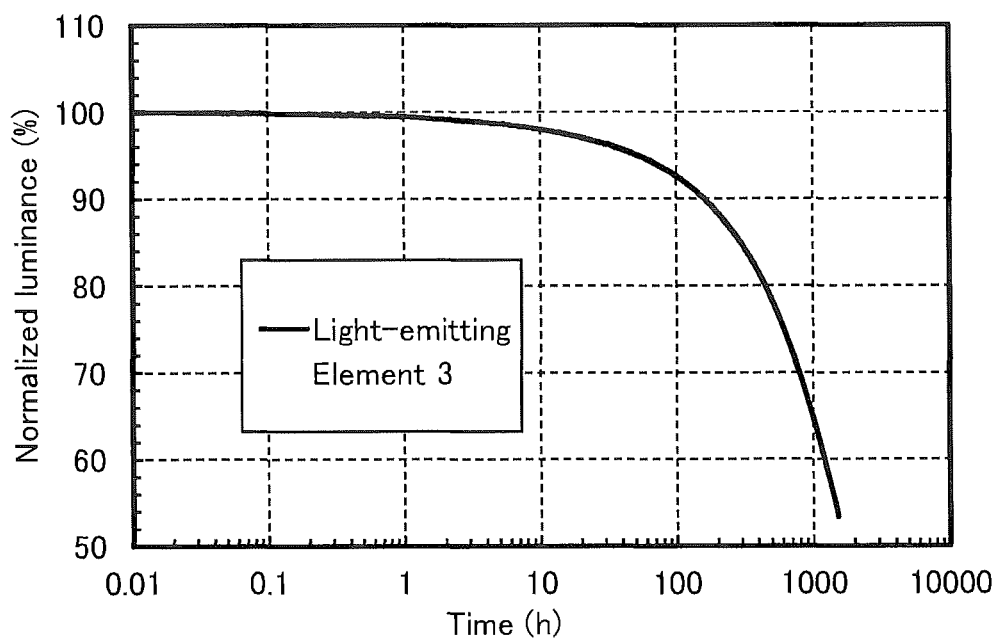
FIG. 24 is a graph showing reliability of Light-emitting Element 3.

Next, a reliability test was performed on Light-emitting Element 3. FIG. 24 shows the results of the reliability test. In FIG. 24, the vertical axis represents normalized luminance (%) with an initial luminance of 100%, and the horizontal axis represents driving time (h) of the element. As the reliability test, a constant current driving test where a constant current was supplied at a current density of 50 mA/cm² was performed.

The results of the reliability test showed that Light-emitting Element 3 has high reliability. This is probably because the benzofuropyrimidine skeleton in 4,8mTpP2Bfpm used in Light-emitting Element 3, which is a skeleton portion with an electron-transport property, has high structural stability and rigidity. Thus, it is indicated that the use of 4,8mTpP2Bfpm (Structural Formula (130)), which is the organic compound of one embodiment of the present invention, is effective in improving the reliability of the light-emitting element.

REFERENCE NUMERALS

101: first electrode, 102: second electrode, 103: EL layer, 103a, 103b: EL layer, 104: charge-generation layer, 111, 111a, 111b: hole-injection layer, 112, 112a, 112b: hole-transport layer, 113, 113a, 113b: light-emitting layer, 114, 114a, 114b: electron-transport layer, 115, 115a, 115b: electron-injection layer, 200R, 200G, 200B: optical path length, 201: first substrate, 202: transistor (FET), 203R, 203G, 203B, 203W: light-emitting element, 204: EL layer, 205: second substrate, 206R, 206G, 206B: color filter, 206R', 206G', 206B': color filter, 207: first electrode, 208: second electrode, 209: black layer (black matrix), 210R, 210G: conductive layer, 301: first substrate, 302: pixel portion, 303: driver circuit portion (source line driver circuit), 304a, 304b: driver circuit portion (gate line driver circuit), 305: sealant, 306: second substrate, 307: lead wiring, 308: FPC, 309: FET, 310: FET, 311: FET, 312: FET, 313: first electrode, 314: insulator, 315: EL layer, 316: second electrode, 317: light-emitting element, 318: space, 900: substrate, 901: first electrode, 903: second electrode, 911: hole-injection layer, 912: hole-transport layer, 913: light-emitting layer, 914: electron-transport layer, 915: electron-injection layer, 4000: lighting device, 4001: substrate, 4002: light-emitting element, 4003: substrate, 4004: first electrode, 4005: EL layer, 4006: second electrode, 4007: electrode, 4008: electrode, 4009: auxiliary wiring, 4010: insulating layer, 4011: sealing substrate, 4012: sealant, 4013: desiccant, 4200: lighting device, 4201: substrate, 4202: light-emitting element, 4204: first electrode, 4205: EL layer, 4206: second electrode, 4207: electrode, 4208: electrode, 4209: auxiliary wiring, 4210: insulating layer, 4211: sealing substrate, 4212: sealant, 4213: barrier film, 4214: planarization film, 5101: light, 5102: wheel, 5103: door, 5104: display portion, 5105: steering wheel, 5106: shifter, 5107: seat, 5108: inner rearview mirror, 7000: housing, 7001: display portion, 7002: second display portion, 7003: speaker, 7004: LED lamp, 7005: operation key, 7006: connection terminal, 7007: sensor, 7008: microphone, 7009: switch, 7010: infrared port, 7011: recording medium reading portion, 7012: support portion, 7013: earphone, 7014: antenna, 7015: shutter button, 7016: image receiving portion, 7018: stand, 7019: microphone, 7020: camera, 7021: external connection portion, 7022, 7023: operation button, 7024: connection terminal, 7025: band, 7026: clasp, 7027: icon indicating time, 7028: another icon, 9310: portable information terminal, 9311: display portion, 9312: display region, 9313: hinge, 9315: housing This application is based on Japanese Patent Application Serial No. 2017-180537 filed with Japan Patent Office on Sep. 20, 2017, the entire contents of which are hereby incorporated herein by reference.

The invention claimed is:

1. An organic compound represented by General Formula (G1),

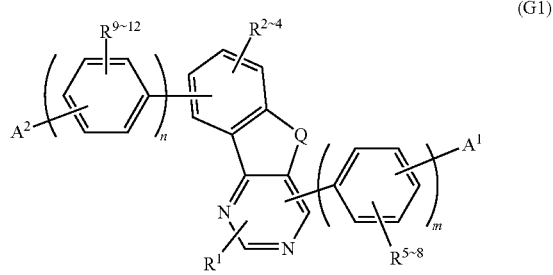

wherein:
Q represents oxygen or sulfur;
each of $A^1$ and $A^2$ independently represents a substituted or unsubstituted polycyclic aromatic hydrocarbon;
m represents any one of integers from 0 to 4;
n represents any one of integers from 1 to 4; and
each of $R^1$ to $R^{12}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

2. The organic compound according to claim 1, wherein each of $A^1$ and $A^2$ is independently any one of a substituted or unsubstituted fluorenyl group, a substituted or unsubstituted spirofluorenyl group, a substituted or unsubstituted phenanthrenyl group, and a substituted or unsubstituted triphenylenyl group.

3. The organic compound according to claim 2, wherein each of $A^1$ and $A^2$ is independently any one of General Formula (A-1) to General Formula (A-14):

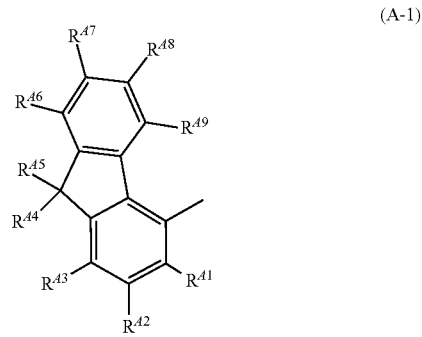

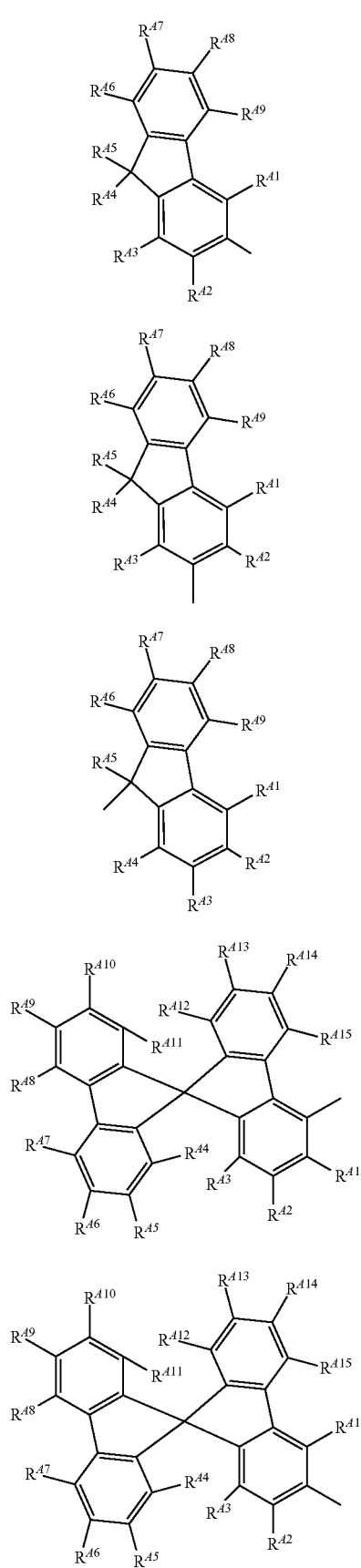
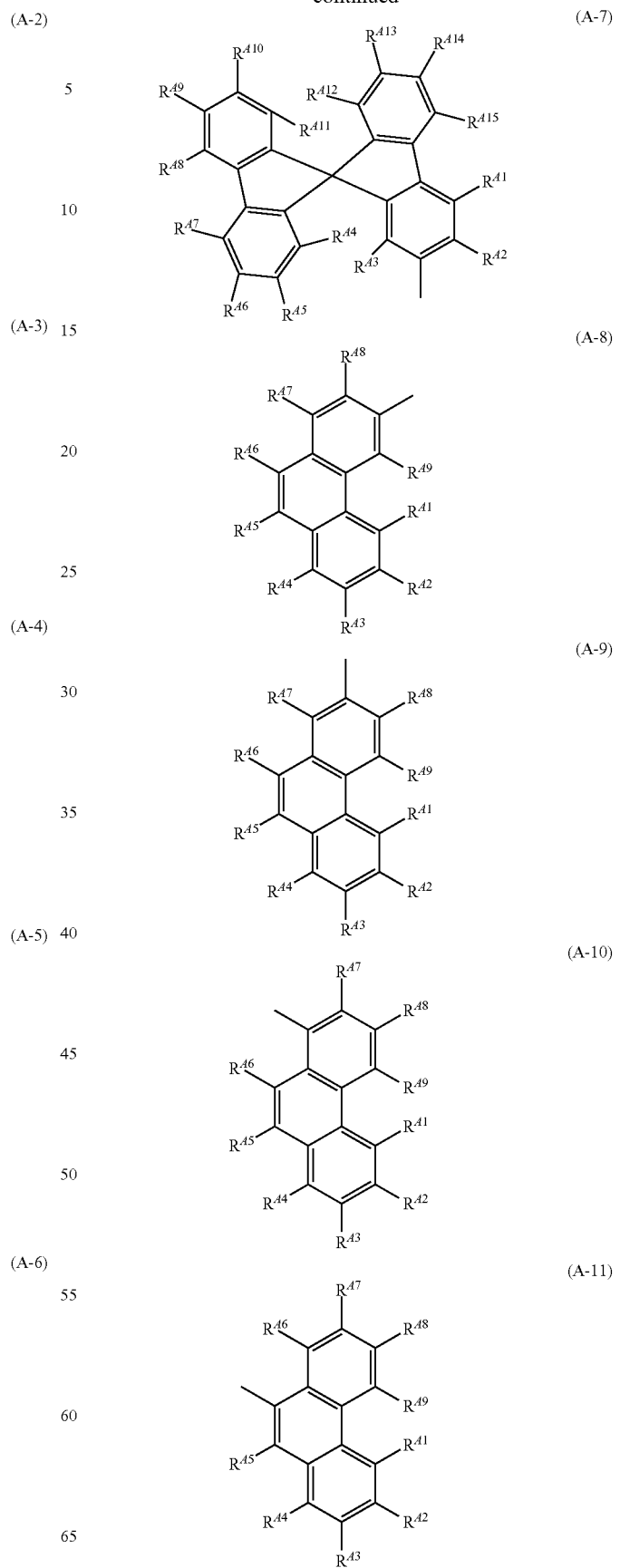

-continued

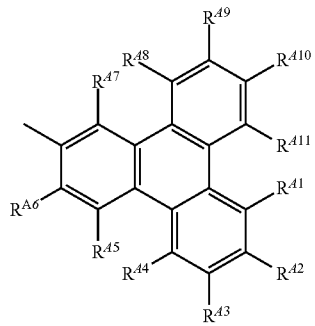
(A-12)

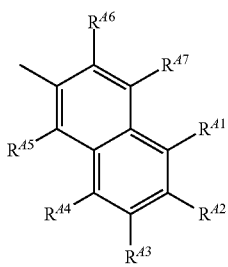
(A-13)

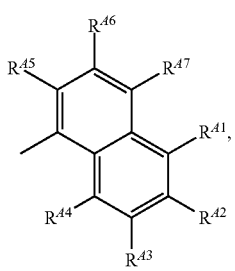
(A-14)

and
wherein each of $R^{A1}$ to $R^{A15}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

4. A light-emitting element comprising an EL layer between a pair of electrodes,
wherein the EL layer comprises the organic compound according to claim 1.

5. A light-emitting device comprising the light-emitting element according to claim 4.

6. An organic compound represented by General Formula (G2),

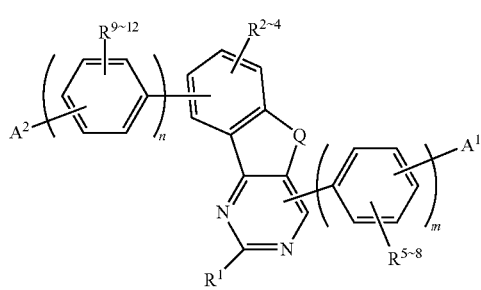
(G2)

wherein:
Q represents oxygen or sulfur;
each of $A^1$ and $A^2$ independently represents a substituted or unsubstituted polycyclic aromatic hydrocarbon;
m represents any one of integers from 0 to 4;
n represents any one of integers from 1 to 4; and
each of $R^1$ to $R^{12}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

7. The organic compound according to claim 6,
wherein each of $A^1$ and $A^2$ is independently any one of a substituted or unsubstituted fluorenyl group, a substituted or unsubstituted spirofluorenyl group, a substituted or unsubstituted phenanthrenyl group, and a substituted or unsubstituted triphenylenyl group.

8. The organic compound according to claim 7,
wherein each of $A^1$ and $A^2$ is independently any one of General Formula (A-1) to General Formula (A-14):

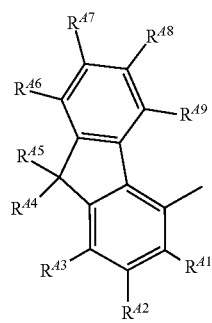
(A-1)

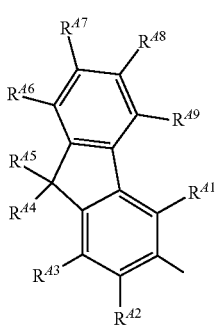
(A-2)

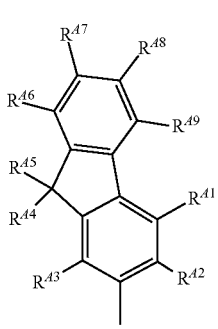
(A-3)

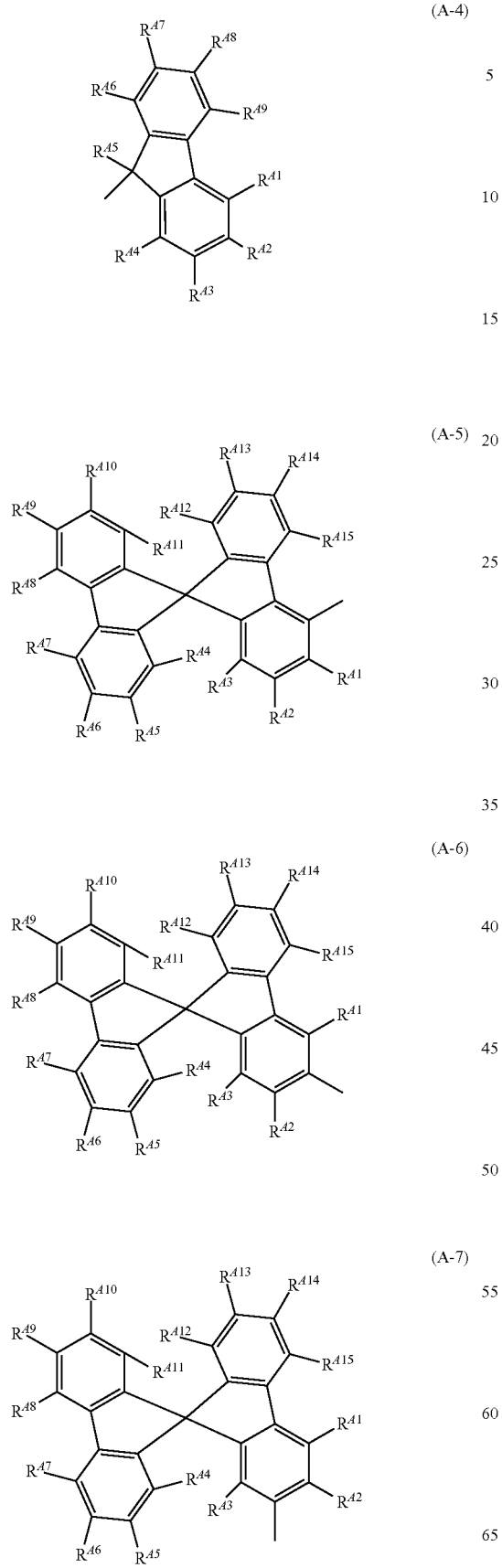
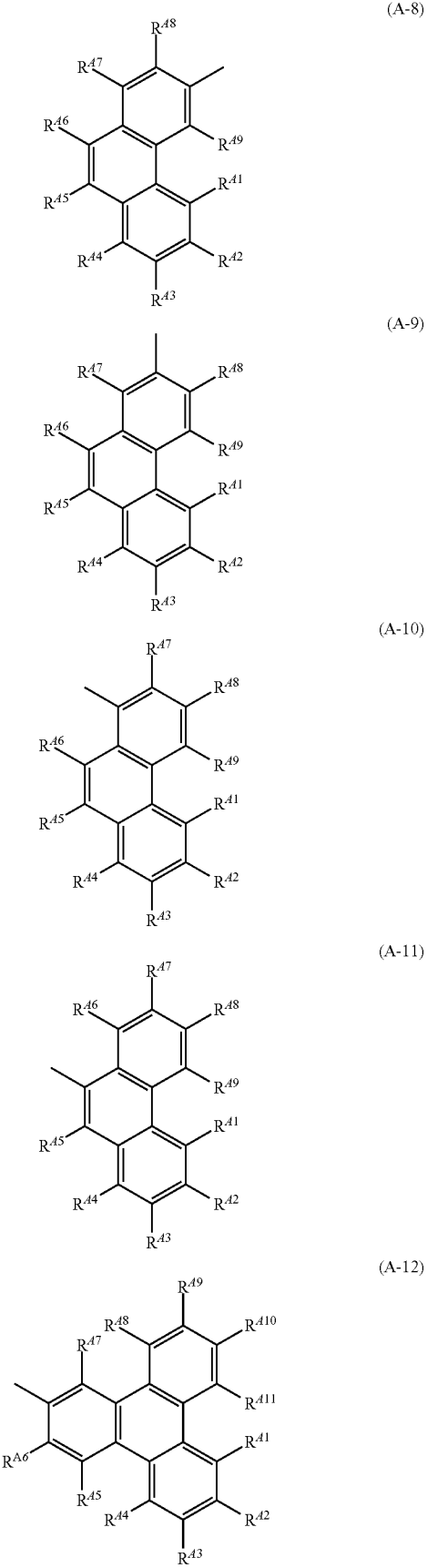

-continued

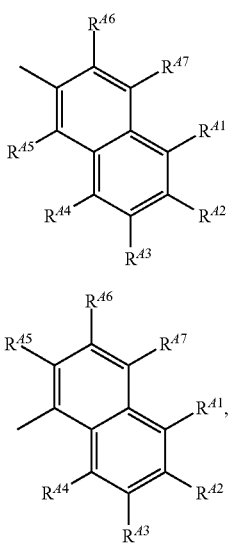

(A-13)

(A-14)

and
wherein each of $R^{A1}$ to $R^{A15}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

9. A light-emitting element comprising an EL layer between a pair of electrodes, wherein the EL layer comprises the organic compound according to claim 6.

10. A light-emitting device comprising the light-emitting element according to claim 9.

11. An organic compound represented by General Formula (G3),

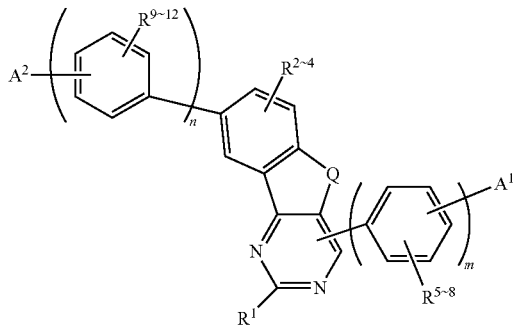

(G3)

wherein:
Q represents oxygen or sulfur;
each of $A^1$ and $A^2$ independently represents a substituted or unsubstituted polycyclic aromatic hydrocarbon;
m represents any one of integers from 0 to 4;
n represents any one of integers from 1 to 4; and
each of $R^1$ to $R^{12}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

12. The organic compound according to claim 11, wherein each of $A^1$ and $A^2$ is independently any one of a substituted or unsubstituted fluorenyl group, a substituted or unsubstituted spirofluorenyl group, a substituted or unsubstituted phenanthrenyl group, and a substituted or unsubstituted triphenylenyl group.

13. The organic compound according to claim 12, wherein each of $A^1$ and $A^2$ is independently any one of General Formula (A-1) to General Formula (A-14):

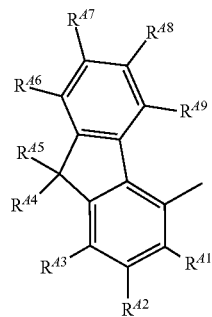

(A-1)

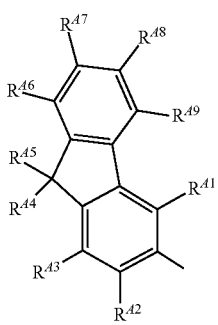

(A-2)

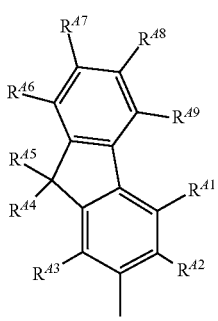

(A-3)

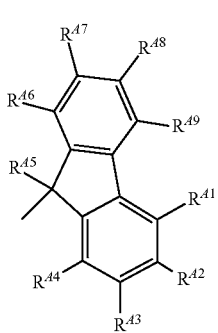

(A-4)

(A-5)
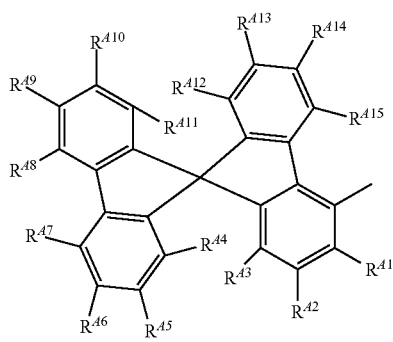
(A-6)
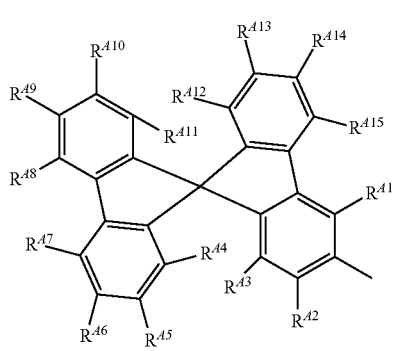
(A-7)
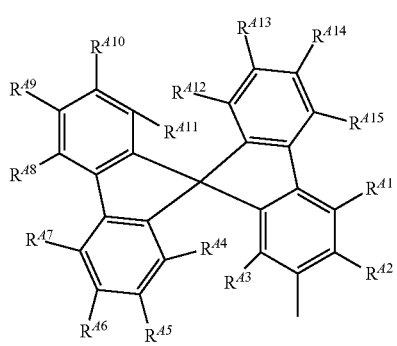
(A-8)
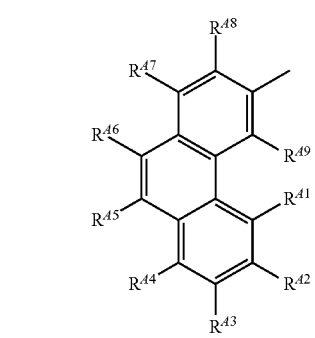
(A-9)
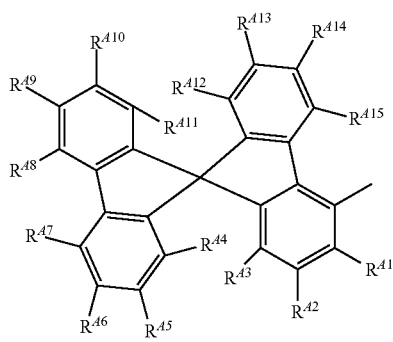
(A-10)
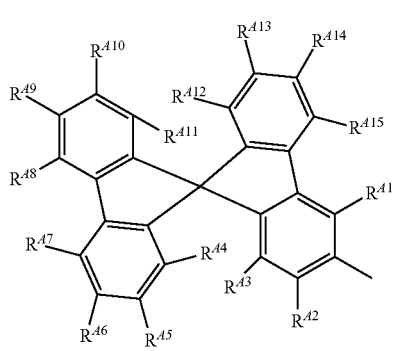
(A-11)
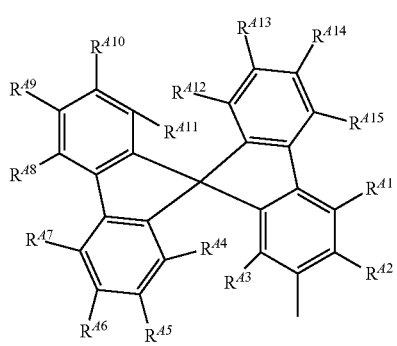
(A-12)
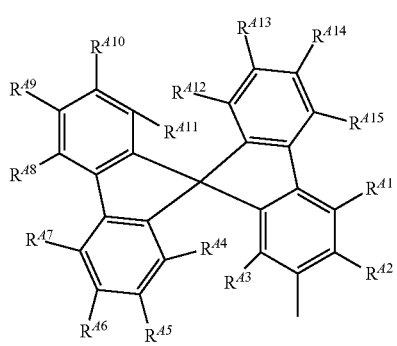
(A-13)
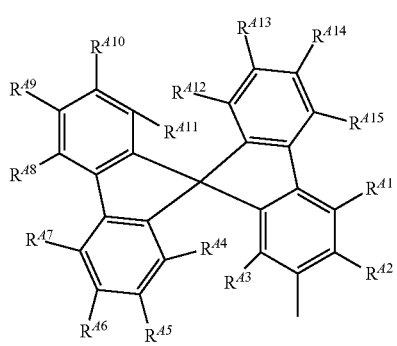

-continued

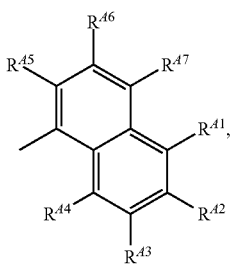
(A-14)

and
wherein each of $R^{A1}$ to $R^{A15}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

14. A light-emitting element comprising an EL layer between a pair of electrodes, wherein the EL layer comprises the organic compound according to claim 11.

15. A light-emitting device comprising the light-emitting element according to claim 14.

16. An organic compound represented by General Formula (G4),

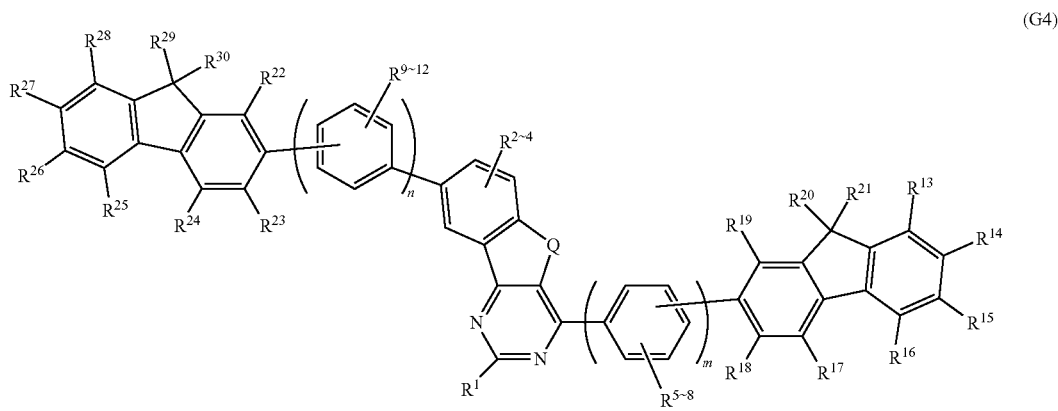
(G4)

wherein:

Q represents oxygen or sulfur;

m represents any one of integers from 0 to 4;

n represents any one of integers from 1 to 4; and each of $R^1$ to $R^{30}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

17. A light-emitting element comprising an EL layer between a pair of electrodes,
  wherein the EL layer comprises the organic compound according to claim 16.

18. A light-emitting device comprising the light-emitting element according to claim 17.

19. An organic compound represented by General Formula (G5),

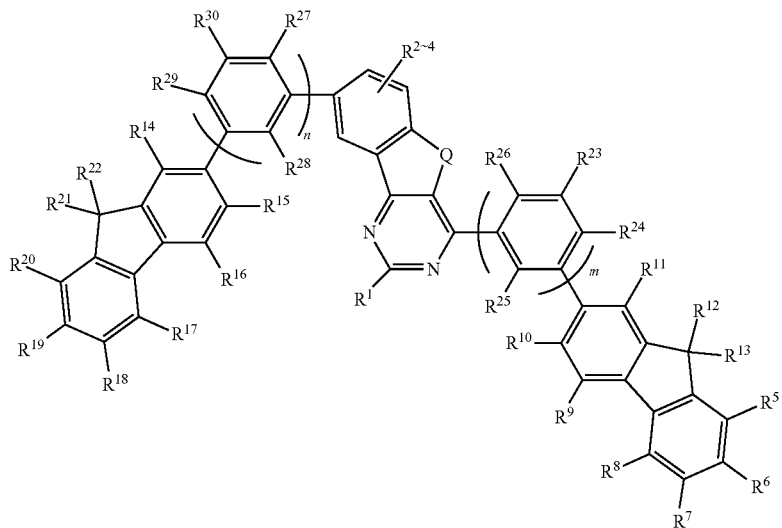

(G5)

wherein:
Q represents oxygen or sulfur;
m represents any one of integers from 0 to 4;
n represents any one of integers from 1 to 4; and
each of $R^1$ to $R^{30}$ independently represents any one of hydrogen, an alkyl group having 1 to 6 carbon atoms, a substituted or unsubstituted cycloalkyl group having 3 to 7 carbon atoms, and a substituted or unsubstituted aryl group having 6 to 13 carbon atoms.

20. The organic compound according to claim 19, wherein the organic compound is represented by Structural Formula (100).

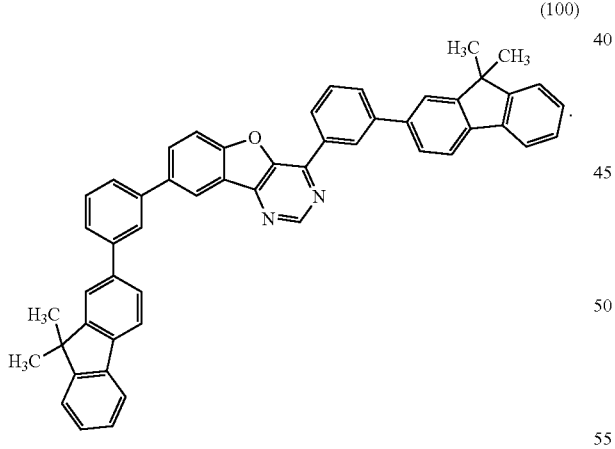

(100)

21. A light-emitting element comprising an EL layer between a pair of electrodes,
wherein the EL layer comprises the organic compound according to claim 19.

22. A light-emitting device comprising the light-emitting element according to claim 21.

* * * * *